(12) United States Patent
Nisnevich et al.

(10) Patent No.: US 9,637,462 B2
(45) Date of Patent: May 2, 2017

(54) PROCESS FOR THE PREPARATION OF N-IODOAMIDES

(71) Applicant: TECHNION RESEARCH & DEVELOPMENT FOUNDATION LIMITED, Haifa (IL)

(72) Inventors: Gennady Nisnevich, Haifa (IL); Kseniya Kulbitski, Haifa (IL); Mark Gandelman, Kfar Saba (IL); Alexander Artaryan, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 15/034,751

(22) PCT Filed: Nov. 5, 2014

(86) PCT No.: PCT/IL2014/050962
§ 371 (c)(1),
(2) Date: May 5, 2016

(87) PCT Pub. No.: WO2015/068159
PCT Pub. Date: May 14, 2015

(65) Prior Publication Data
US 2016/0272598 A1    Sep. 22, 2016

(30) Foreign Application Priority Data
Nov. 7, 2013 (IL) .......................................... 229326

(51) Int. Cl.
| | | |
|---|---|---|
| *C07D 263/26* | (2006.01) | |
| *C07D 275/06* | (2006.01) | |
| *C07D 233/82* | (2006.01) | |
| *C07C 41/22* | (2006.01) | |
| *C07D 233/74* | (2006.01) | |
| *C07D 263/22* | (2006.01) | |
| *C07D 209/48* | (2006.01) | |
| *C07C 17/093* | (2006.01) | |
| *C07C 29/64* | (2006.01) | |
| *C07C 41/05* | (2006.01) | |
| *C07C 67/05* | (2006.01) | |
| *C07C 201/12* | (2006.01) | |
| *C07D 211/38* | (2006.01) | |
| *C07C 17/10* | (2006.01) | |
| *C07C 17/12* | (2006.01) | |
| *C07C 17/14* | (2006.01) | |
| *C07C 17/363* | (2006.01) | |
| *C07B 39/00* | (2006.01) | |
| *C07D 207/46* | (2006.01) | |

(52) U.S. Cl.
CPC ............ *C07D 263/26* (2013.01); *C07B 39/00* (2013.01); *C07C 17/093* (2013.01); *C07C 17/10* (2013.01); *C07C 17/12* (2013.01); *C07C 17/14* (2013.01); *C07C 17/363* (2013.01); *C07C 29/64* (2013.01); *C07C 41/05* (2013.01); *C07C 41/22* (2013.01); *C07C 67/05* (2013.01); *C07C 201/12* (2013.01); *C07D 207/46* (2013.01); *C07D 209/48* (2013.01); *C07D 211/38* (2013.01); *C07D 233/74* (2013.01); *C07D 233/82* (2013.01); *C07D 263/22* (2013.01); *C07D 275/06* (2013.01); *C07C 2101/08* (2013.01); *C07C 2101/14* (2013.01); *C07C 2101/16* (2013.01); *C07C 2101/18* (2013.01); *C07C 2102/42* (2013.01)

(58) Field of Classification Search
CPC ... C07D 263/26; C07D 275/06; C07D 233/82
See application file for complete search history.

(56) References Cited

FOREIGN PATENT DOCUMENTS

WO    2011/154953    12/2011

OTHER PUBLICATIONS

Yang et al. Tetrahedron Letters 2013, 54, 6799-6803.*
Veitch et al. Angew. Chem. Int. Ed. 2010, 49, 7332-7335 and its supporting information.*
Darko Dolenc "N-Iodosaccharin—a New Reagent for Iodination of Alkenes and Activated Aromatics1" Synlett (2000), vol. 4, pp. 544-546.
The International Search Report (ISR) for PCT/IL2014/050962, dated Jan. 23, 2015.
The Written Opinion of the International Searching Authority for PCT/IL2014/050962, dated Jan. 23, 2015.

* cited by examiner

*Primary Examiner* — Matthew Coughlin
(74) *Attorney, Agent, or Firm* — McDonnell Boehnen Hulbert & Berghoff LLP

(57) ABSTRACT

The present invention provides new stable crystalline N-iodoamides-1-iodo-3,5,5-trimethylhydantoin (1-ITMH) and 3-iodo-4,4-dimethyl-2-oxazolidinone (IDMO). The present invention further provides a process for the preparation of organic iodides using N-iodoamides of this invention and recovery of the amide co-products from waste water.

24 Claims, 10 Drawing Sheets

PROCESS FOR THE PREPARATION OF N-IODOAMIDES

CROSS-REFERENCE TO RELATED APPLICATIONS

This application is a U.S. national phase of International Application No. PCT/IL2014/050962, filed on Nov. 5, 2014, which claims priority to Israeli Patent No. 229326, filed Nov. 7, 2013.

FIELD OF THE INVENTION

The present invention provides new stable crystalline N-iodoamides and preparation thereof. The present invention further provides a process for the preparation of organic iodides using N-iodoamides of this invention and recovery of the amide co-products from waste water.

BACKGROUND OF THE INVENTION

Commercially available N-iodoamides, such as 1,3-diiodo-5,5-dimethylhydantoin (DIH, TCIMAIL No. 144, 2011) and N-iodosuccinimide (NIS e-EROS) are highly reactive iodination agents and are widely used in laboratory practice as efficient reagents for addition of iodine atom to alkene, substitution of hydrogen in aromatic compound with iodine, or substitution of carboxylic group in organic acid with iodine atom (WO2011154953A1; Adv. Synth. Catal. 2011, v. 353, 1438). The iodination with N-iodoamide gives a mixture of desired organic iodide and equimolar quantity of amide as co-product. The water soluble amide is separated from the lipophilic organic iodide by water treatment. Ease of separation of reaction products from side products determines the success and popularity of the stable N-iodoamides as iodination agents in laboratory practice. However, the lack of 5,5-dimethylhydantoin and succinimide recovery processes limit the use of 1,3-diiodo-5,5-dimethylhydantoin and N-iodosuccinimide in the industry. In ideal case, the amide co-products must be soluble in water and at the same time can be easily recovered from aqueous solutions. It would seem that N-iodosaccharin (NISac) is suitable on the role of the ideal iodination agent as saccharin is soluble in aqueous alkali and precipitated after acidification. However, the scope of use of NISac is limited by the reactions of electrophilic iodination (Synlett 2000, 544). Thus search for a new generation of stable N-iodoamides suitable for radical and electrophilic iodination is an actual problem.

N-iodoamide for industrial use should possess high stability in pure state and high reactivity in radical and electrophilic reactions. Method of preparation of the N-iodoamide should be simple and effective. Corresponding amide must be soluble in water and, at the same time, can be easily recovered from aqueous solutions.

SUMMARY OF THE INVENTION

In one embodiment, this invention provides a process for the preparation of organic iodide comprising the steps of:
(a) reacting an amide with iodine and [bis(acyloxy)iodo] arene in aprotic solvent to yield N-iodoamide and iodoarene as co-product;
(b) reacting an organic compound with said N-iodoamide of step (a) to yield desired organic iodide and amide as co-product; and
(c) recovering said amide co-product from the reaction mixture of step (b);

wherein said amide is 4,4-dimethyloxazolidin-2-one, saccharin or 3,5,5-trimethylhydantoin and said N-iodoamide is 3-iodo-4,4-dimethyloxazolidin-2-one (IDMO), N-iodosaccharin (NISac) or 1-iodo-3,5,5-trimethylhydantoin (1-ITMH), respectively.

In another embodiment, the organic compound is a carboxylic acid, an alkene, an alkane, an alkyne, ketone, a cycloalkane, methylarene, aromatic compound or combination thereof.

In another embodiment, the carboxylic acid compound is R—COOH, R—CH=CH—COOH, R—(CH$_2$)$_o$—COOH or R—C≡C—COOH wherein o is an integer between 1 and 6, and R is substituted or unsubstituted linear or branched alkyl, substituted or unsubstituted linear or branched alkylene, substituted or unsubstituted linear or branched alkyne, substituted or unsubstituted aryl, substituted or unsubstituted Ph(CH$_2$)$_p$— wherein p is an integer between 1 and 6, substituted or unsubstituted, saturated or unsaturated cycloalkyl, substituted or unsubstituted saturated or unsaturated heterocycloalkyl or any combination thereof.

In one embodiment, this invention provides a process for the preparation of N-iodoamide comprising reacting a primary or a secondary amide with iodine and [bis(acyloxy) iodo]arene in an aprotic solvent to yield desired N-iodoamide and iodoarene as co-product.

In another embodiment, this invention provides a process for the preparation of N-iodoamide comprising reacting a primary or a secondary amide with iodine and [bis(acyloxy) iodo]arene in an aprotic solvent; wherein said amide is

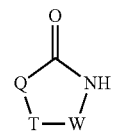

(2B)

and said N-iodoamide is

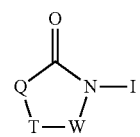

(1B)

wherein
W is C=O, SO$_2$, or C(CH$_3$)$_2$;
T is CH$_2$, C=O, C(CH$_3$)$_2$;
Q is O, NCH$_3$, CH$_2$; or T and Q are carbons and are fused together with a substituted or unsubstituted benzene; wherein said substituents are NO$_2$, CN, CF$_3$, halogen, or combination thereof.

In one embodiment, the N-iodoamide prepared according to the process of this invention is: 3-iodo-4,4-dimethyloxazolidin-2-one, 1-iodo-3,5,5-trimethylhydantoin, 3-iodo-1,5,5-trimethylhydantoin, N-iodosaccharin, N-iodosuccinimide, N-iodophthalimide, or N-iodo-4-nitrophthalimide.

In one embodiment, this invention provides a crystalline form of 3-iodo-4,4-dimethyloxazolidin-2-one (IDMO).

In one embodiment, this invention provides a crystalline form of 3-iodo-4,4-dimethyloxazolidin-2-one (IDMO) characterized by molecular packing arrangement defined by space group P 21/n and unit cell dimensions a=5.7963(3) Å, b=10.9989(5) Å, c=11.9849(6) Å, α=γ=90°, β=98.580(2)° at 200(1) K.

In one embodiment, this invention provides a compound, wherein said compound is N-iodo substituted N',5,5-trimethylhydantoin. In another embodiment, the compound is 1-iodo-3,5,5-trimethylhydantoin or 3-iodo-1,5,5-trimethylhydantoin.

In one embodiment, this invention provides a crystalline 1-iodo-3,5,5-trimethylhydantoin. In one embodiment, this invention provides a crystalline 1-iodo-3,5,5-trimethylhydantoin characterized by an x-ray powder diffraction pattern having characteristic peaks, expressed in degrees 2θ at about 13.0±0.2, 17.0±0.2, 22.6±0.2, 22.9±0.2, 25.2±0.2, 26.4±0.2, 28.3±0.2, 29.5±0.2, and 34.7±0.2 at 293(2) K.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 10A and 10B present oxidation of iodoarene (ArI) in the presence of oxidizing agent ("O") and carboxylic acid to give [bis(acyloxy)iodo]arene. R' is substituted or unsubstituted alkyl or aryl radical. FIG. 10C is a schematic presentation of specific example for the preparation of (diacetoxyiodo)benzene [PhI(OAc)$_2$] and [bis(trifluoroacetoxy)iodo]benzene [PhI(OAc$_F$)$_2$] from iodobenzene.

Figure 1:
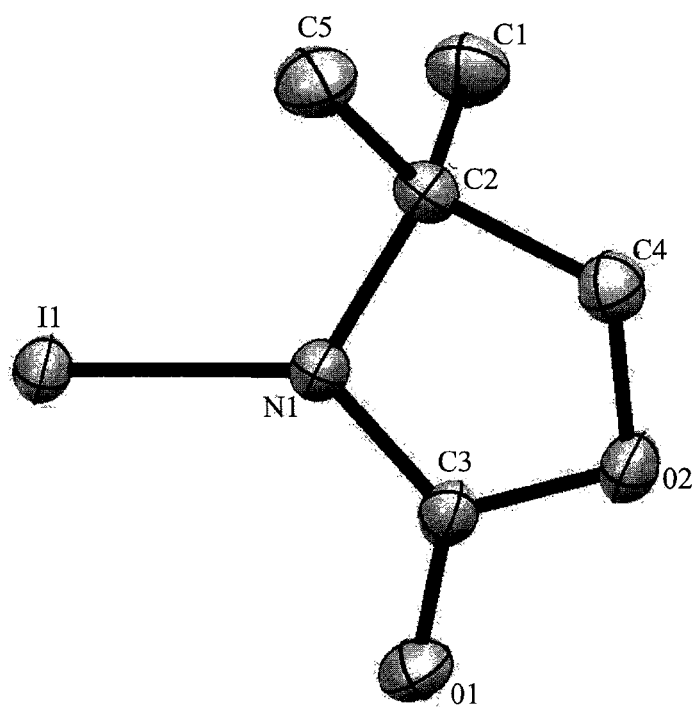
FIG. 1 depicts Oak Ridge Thermal-Ellipsoid Plot Program (ORTEP) view of 3-iodo-4,4-dimethyloxazolidin-2-one molecule and the atomic numbering of non-hydrogen atoms as derived from single crystal x-ray analysis of the crystalline 3-iodo-4,4-dimethyloxazolidin-2-one.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention is directed to a process for the preparation of N-iodoamide comprising reacting an amide with iodine and bis(acyloxy)iodoarene. In one embodiment, this invention is directed to a process for the preparation of N-iodoamide comprising reacting a primary or a secondary amide with iodine and [bis(acyloxy)iodo]arene. In another embodiment, the process for the preparation of N-iodoamide is presented in Scheme A:

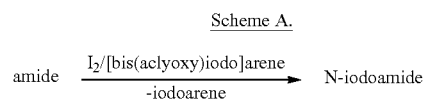

Scheme A.

In one embodiment, this invention is directed to a process for the preparation of N-iodoamide represented by formula (1):

comprising reacting an amide of formula (2):

with iodine and [bis(acyloxy)iodo]arene in an aprotic solvent;

wherein

X is —C(=O)CH$_3$, —C(=O)OCH$_3$, —C(=O)NH$_2$, —S(=O)$_2$CH$_3$ or —S(=O)$_2$NH$_2$; wherein said CH$_3$ or said NH$_2$ of said C(=O)CH$_3$, —C(=O)OCH$_3$, —C(=O)NH$_2$, —S(=O)$_2$CH$_3$ and —S(=O)$_2$NH$_2$ is optionally substituted;

Y is —C(CH$_3$)$_3$, —C(=O)CH$_3$; wherein said CH$_3$ of said —C(CH$_3$)$_3$ and —C(=O)CH$_3$ is optionally substituted; and X and Y optionally form a ring.

In one embodiment, the N-iodoamide of formula (1) and the corresponding amide of formula (2) are cyclic. In another embodiment, X and Y of the N-iodoamide of formula (1) and the corresponding amide of formula (2) form a ring.

In another embodiment, X of formula (1) and of formula (2) is —C(=O)CH$_3$, —C(=O)OCH$_3$, —C(=O)NH$_2$, —S(=O)$_2$CH$_3$ or —S(=O)$_2$NH$_2$; wherein said CH$_3$ or said NH$_2$ of said C(=O)CH$_3$, —C(=O)OCH$_3$, —C(=O)NH$_2$, —S(=O)$_2$CH$_3$ and —S(=O)$_2$NH$_2$ is optionally substituted. In another embodiment, the CH$_3$ or said NH$_2$ are substituted by alkyl, nitro, halogen, hydroxyl, —CN, -amine, COOH or alkoxy.

In another embodiment, Y of formula (1) and of formula (2) is —C(CH$_3$)$_3$, —C(=O)CH$_3$; wherein said CH$_3$ of said —C(CH$_3$)$_3$ and —C(=O)CH$_3$ is optionally substituted. In another embodiment, the CH$_3$ is substituted by alkyl, halogen, hydroxyl, —CN, -amine, COOH or alkoxy.

In one embodiment, this invention is directed to a process for the preparation of N-iodoamide represented by formula (1A):

L-C(=O)—N(-M)-I (1A)

comprising reacting an amide of formula (2A):

L-C(=O)—N(-M)-H (2A)

with iodine and [bis(acyloxy)iodo]arene in an aprotic solvent;
wherein L is a carbon, a nitrogen or an oxygen atom; and M is a carbon or a sulfur atom.

In one embodiment, the amide of formula (2A) and the N-iodoamide of formula (1A) are amides which are part of a linear, branched or a cyclic compound. In another embodiment, the amide (formula (2A)) used for the preparation of N-amide is a lactam, carboxamide, sulfonamide, carbamate, hydantoin, imide, or ureide or combination thereof.

In one embodiment, this invention is directed to a process for the preparation of N-iodoamide represented by formula (1A):

L-C(=O)—N(M)-I (1A)

comprising reacting an amide of formula (2A):

L-C(=O)—N(M)-H (2A)

with iodine and [bis(acyloxy)iodo]arene in an aprotic solvent;
wherein L is a $O(CH_2)_nZ$; $N(CH_3)Z$, $N(CH_3)C(CH_3)_2Z$, $-(CH_2)_nZ$; wherein n is an integer between 0-4; and Z is $CH_3$ or $COCH_3$;
M is a $C(CH_3)_2Z'$, $C(=O)C(CH_3)_2Z'$, $SO_2(CH_2)_mZ'$, $C(=O)(CH_2)_mZ'$;
wherein m is an integer between 0-4; and Z' is $CH_3$; and wherein if L and M form a cyclic ring then Z is a bond or —C(O)—, and Z' is a bond;
wherein said cyclic ring is optionally fused with a substituted or unsubstituted phenyl.

In one embodiment, this invention is directed to a process for the preparation of N-iodoamide represented by formula (1B):

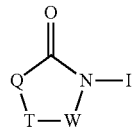
 (1B)

comprising reacting an amide of formula (2B):

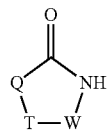
 (2B)

with iodine and [bis(acyloxy)iodo]arene in an aprotic solvent;
wherein
W is C=O, $SO_2$, or $C(CH_3)_2$;
T is $CH_2$, C=O, $C(CH_3)_2$;
Q is O, $NCH_3$, $CH_2$; or T and Q are carbons and are fused together with a substituted or unsubstituted benzene; wherein said substituents are $NO_2$, CN, $CF_3$, halogen, or combination thereof.

Non limiting examples of N-iodoamides prepared according to the process of this invention include:

3-iodo-4,4-dimethyloxazolidin-2-one of formula IDMO:

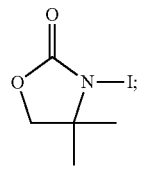
IDMO 1-iodo-3,5,5-trimethylhydantoin of formula 1-ITMH:

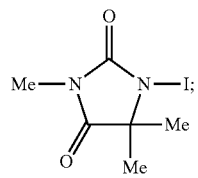
1-ITMH 3-iodo-1,5,5-trimethylhydantoin of formula 3-ITMH:

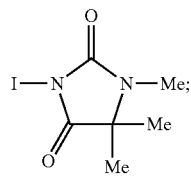
3-ITMH

N-iodosaccharin of formula NISac:

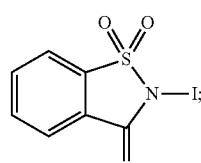
NISac

N-iodosuccinimide of formula NIS:

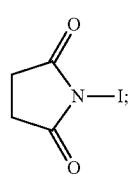
NIS

N-iodophthalimide of formula IPT:

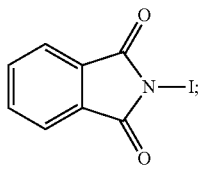

or N-iodo-4-nitrophthalimide of formula INPT:

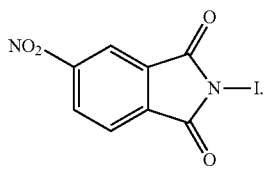

In one embodiment, this invention provides a process for the preparation of N-iodoamide comprising reacting an amide with iodine and [bis(acyloxy)iodo]arene in non-aqueous media. In one embodiment, this invention provides a process for the preparation of N-iodoamide comprising reacting a primary or a secondary amide with iodine and [bis(acyloxy)iodo]arene in non-aqueous media. In another embodiment, the process for the preparation of N-iodoamide is in an aprotic solvent. In another embodiment, "aprotic solvent" or "non-aqueous" solvent is referred to the following solvents: aromatic (benzene, toluene), aliphatic (hexane, heptane, cyclohexane) hydrocarbon, a halogenated aromatic (chlorobenzene, iodobenzene, benzotrifluoride), a halogenated aliphatic hydrocarbon (dichloromethane, chloroform, carbon tetrachloride, 1,2-dichloroethane), nitrile (acetonitrile), nitro compounds (nitromethane, nitrobenzene), ester (methyl acetate, ethyl acetate, isopropyl acetate), ether (ethyl ether, 1,4-dioxane, dioxolane, methyl tert-butyl ether), substituted amide (DMF, DMA, NMP), or any combination thereof.

In one embodiment the process for the preparation of N-iodoamide of this invention includes reacting a primary or a secondary amide with iodine and [bis(acyloxy)iodo]arene in an aprotic solvent to yield desired N-iodoamide and iodoarene as co-product. In another embodiment, the reaction is conducted for 1 to 12 hours at a temperature of between −10° C. to +50° C. In another embodiment, the temperature is between −10° C. to +10° C. In another embodiment, the temperature is between 0° C. to +20° C. In another embodiment, the temperature is between 0° C. to +5° C. In another embodiment, the temperature is a room temperature. In another embodiment, the temperature is between +20° C. to +40° C. In another embodiment, the reaction for the preparation of N-iodoamide is conducted for 1 to 12 hours. In another embodiment, the reaction for the preparation of N-iodoamide is conducted for 1 to 5 hours. In another embodiment, the reaction for the preparation of N-iodoamide is conducted for 1 to 3 hours. In another embodiment, the reaction for the preparation of N-iodoamide is conducted for 3 to 8 hours.

In one embodiment, this invention provides a process for the preparation of N-iodoamide comprising reacting an amide with iodine and [bis(acyloxy)iodo]arene. In another embodiment, 0.5 to 1.5 mole equivalents of [bis(acyloxy)iodo]arene per 1 equivalent an amide starting material is used. In another embodiment, 1 mole equivalent of bis(acyloxy)iodoarene per 1 equivalent an amide starting material is used. In another embodiment, 0.8 to 1.2 mole equivalent of [bis(acyloxy)iodo]arene per 1 equivalent of an amide starting material is used.

In another embodiment, N-iodoamide is prepared according to process described in Example 4.

In one embodiment, [bis(acyloxy)iodo]arene is used for the preparation of N-iodoamide and iodoarene is formed as a co-product together with the N-iodoamide. (as presented in Scheme 1 above).

In another embodiment, the "arene" of [bis(acyloxy)iodo]arene or of iodoarene include non limiting examples such as benzene, toluene, (triflumethyl)benzene, pyridine, naphthalene, biphenyl, pyrrol, pyrazine, pyrimidine, pyrazole, furan, thiophene, thiazole, imidazole, isoxazole, and the like. In another embodiment, the arene is benzene. In another embodiment, the arene is toluene. In another embodiment, the arene is (trifluoromethyl)benzene. In another embodiment, the arene is pyridine. In another embodiment, the arene is naphthalene. In another embodiment, the arene is biphenyl. In another embodiment, the arene is pyrrole. In another embodiment, the arene is pyrazine. In another embodiment, the arene is pyrimidine. In another embodiment, the arene is pyrazole. In another embodiment, the arene is furane. In another embodiment, the arene is thiophene. In another embodiment, the arene is thiazole. In another embodiment, the arene is imidazole. In another embodiment, the arene is isoxazole, and the like. In another embodiment, the arene is optionally substituted by halogen, nitro, alkoxycarbonyl (methoxycarbonyl, ethoxycarbonyl), nitrile, $CF_3$, alkyl, substituted alkyl or alkoxy (methoxy, ethoxy) groups.

In another embodiment, the "acyl" of bis(acyloxy)iodoarene is substituted or unsubstituted acetyl or benzoyl. In another embodiment, the acetyl is substituted by an alkyl, halogen, aryl. In another embodiment, the acyl is trifluoroacetyl group.

In one embodiment, this invention is directed to a process for the preparation of N-iodoamide comprising reacting an amide with iodine and [bis(acyloxy)iodo]arene to yield N-iodoamide and iodoarene as a co-product, wherein the iodoarene is isolated and recovered from the reaction mixture and optionally oxidized to yield [bis(acyloxy)iodo]arene.

Figure 10A:
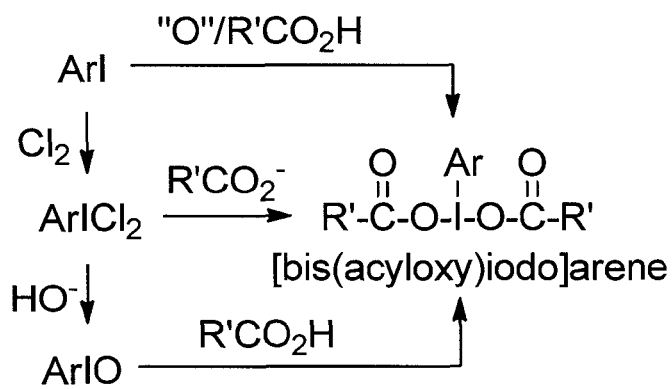
FIGS. 10A-10C depict schematic presentation of recovery of iodoarene coproduct to [bis(acyloxy)iodo]arene.
Figure 10B:
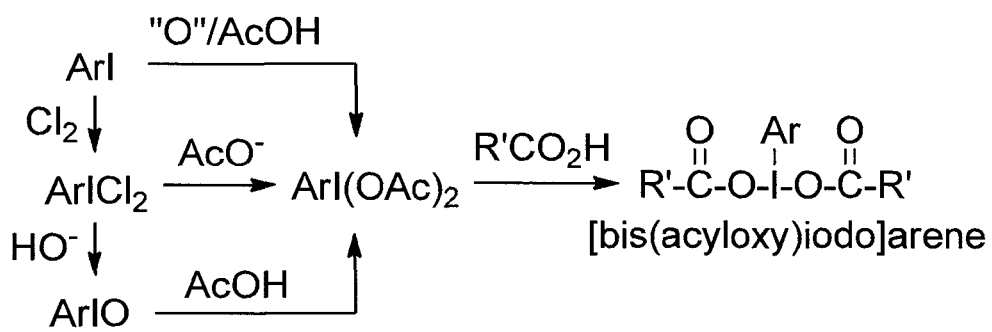
Figure 10C:
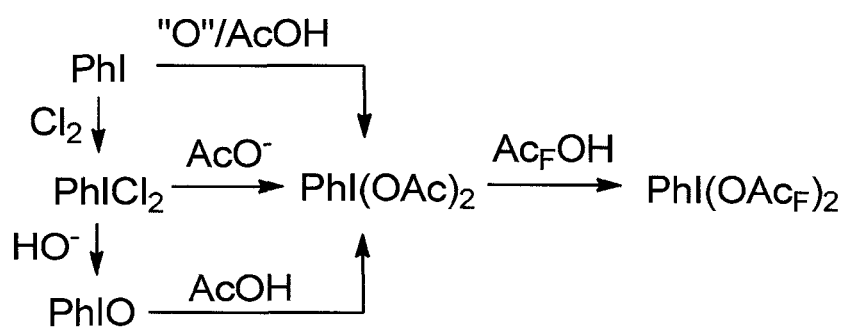

In another embodiment, the iodoarene co-product is oxidized in the presence of carboxylic acid and an oxidizing agent to yield bis(acyloxy)iodo]arene as presented in FIGS. 10A-10C. Non limiting examples of oxidizing agents include aq $H_2O_2$, $AcO_2H$, $NaBO_4.H_2O$, $Na_2CO_3.1.5H_2O_2$, $K_2S_2O_8$ and $H_2O_2.urea$. The carboxylic acid used is R'COOH, wherein R' is substituted or nonsubstituted alkyl or aryl. Non limiting examples of carboxylic acid include: acetic acid, trifluoroacetic acid, propionic acid, benzoic acid.

In one embodiment, this invention is directed to 1-iodo-3,5,5-trimethylhydantoin. In one embodiment, this invention is directed to 3-iodo-1,5,5-trimethylhydantoin. In one embodiment, this invention is directed to N-iodoamide, wherein said N-iodoamide is 1-iodo-3,5,5-trimethylhydantoin or 3-iodo-1,5,5-trimethylhydantoin. In another embodiment, 1-iodo-3,5,5-trimethylhydantoin and 3-iodo-1,5,5-trimethylhydantoin are prepared as described in Example 4.

In one embodiment, this invention is directed to a solid form of 3-iodo-4,4-dimethyloxazolidin-2-one, 3-iodo-1,5,5-trimethylhydantoin, and 1-iodo-3,5,5-trimethylhydantoin and to methods of preparation thereof.

N-Haloamide stability is important factor for the conditions of its preparation, storage and use. Physical form of the N-haloamide largely determines its stability. N-haloamide in the solid state is more stable than the liquid state. A crystalline form is more stable than an amorphous form.

In one embodiment, this invention is directed to crystalline 3-iodo-4,4-dimethyloxazolidin-2-one. In one embodiment, this invention is directed to crystalline 3-iodo-4,4-dimethyloxazolidin-2-one having a molecular packing arrangement defined by space group P 21/n and unit cell dimensions a=5.7963(3) Å, b=10.9989(5) Å, c=11.9849(6) Å, $\alpha=\gamma=90°$, $\beta=98.580(2)°$ at 200(1) K. In another embodiment, the crystalline form of 3-iodo-4,4-dimethyloxazolidin-2-one is obtained according to Example 5. In another embodiment the ORTEP view of 3-iodo-4,4-dimethyloxazolidin-2-one is as presented in FIG. 1.

In one embodiment, this invention is directed to crystalline 1-iodo-3,5,5-trimethylhydantoin. In one embodiment, this invention is directed to crystalline 1-iodo-3,5,5-trimethylhydantoin characterized by x-ray powder diffraction pattern having characteristic peaks, expressed in degrees 2θ at about 13.0±0.2, 17.0±0.2, 22.6±0.2, 22.9±0.2, 25.2±0.2, 26.4±0.2, 28.3±0.2, 29.5±0.2, and 34.7±0.2 at 293(2) K. In another embodiment, the crystalline 1-iodo-3,5,5-trimethylhydantoin exhibits an x-ray powder diffraction pattern at 293(2) K substantially as presented in FIG. 3.

In one embodiment, this invention is directed to crystalline form of 3-iodo-1,5,5-trimethylhydantoin. In another embodiment, this invention is directed to crystalline form of 3-iodo-1,5,5-trimethylhydantoin having a molecular packing arrangement defined by space group Pnma and unit cell dimensions a=11.217(3) Å, b=7.423(2)Å, c=10.454(2) Å, $\alpha=\beta=\gamma=90°$, at 293(2) K. In another embodiment, the crystalline form of 3-iodo-1,5,5-trimethylhydantoin is obtained according to Example 6. In another embodiment the ORTEP view of 3-iodo-1,5,5-trimethylhydantoin is as presented in FIG. 5.

In one embodiment, this invention provides a process for the preparation of organic iodide comprising reacting an organic compound with N-iodoamide to yield desired organic iodide and amide as co-product; wherein said N-iodoamide is 3-iodo-4,4-dimethyloxazolidin-2-one (IDMO) or 1-iodo-3,5,5-trimethylhydantoin (1-ITMH); said amide is 4,4-dimethyloxazolidin-2-one or 3,5,5-trimethylhydantoin, respectively.

In another embodiment, this invention provides a process for the preparation of organic iodide comprising reacting an organic compound with N-iodoamide to yield desired organic iodide and amide as co-product; wherein said organic compound is a carboxylic acid, an alkene, an alkyne, an alkane, a cycloalkane, methylarene, ketone, aromatic compound or combination thereof; said N-iodoamide is 3-iodo-4,4-dimethyloxazolidin-2-one (IDMO) or 1-iodo-3,5,5-trimethylhydantoin (1-ITMH); said amide is 4,4-dimethyloxazolidin-2-one or 3,5,5-trimethylhydantoin, respectively.

In one embodiment, this invention is directed to a process for the preparation of organic iodide comprising the steps of:
 (a) reacting an amide with iodine and [bis(acyloxy)iodo]arene to yield N-iodoamide;
 (b) reacting an organic compound with said N-iodoamide of step (a) to yield desired organic iodide;
wherein said organic compound of step (b) is a carboxylic acid compound, an alkene, an alkane, an alkyne, ketone, a cycloalkane, an alkylarene, an aromatic compound or any combination thereof. In another embodiment, the alkylarene is methylarene.

In one embodiment, this invention provides a process for the preparation of organic iodide comprising the steps of:

(a) reacting an amide with iodine and [bis(acyloxy)iodo]arene in aprotic solvent to yield N-iodoamide and iodoarene as co-product;
(b) reacting an organic compound with said N-iodoamide of step (a) to yield desired organic iodide and amide as co-product; and
(c) recovering said amide co-product from the reaction mixture of step (b); wherein said amide is 4,4-dimethyloxazolidin-2-one, saccharin or 3,5,5-trimethylhydantoin and said N-iodoamide is 3-iodo-4,4-dimethyloxazolidin-2-one (IDMO), N-iodosaccharin (NIS ac) or 1-iodo-3,5,5-trimethylhydantoin (1-ITMH), respectively.

In another embodiment, the carboxylic acid compound is R—COOH, R—(CH$_2$)$_o$—COOH, R—CH═CH—COOH or R—C≡C—COOH wherein o is an integer between 1 and 6 and R is substituted or unsubstituted linear or branched alkyl, substituted or unsubstituted linear or branched alkylene, substituted or unsubstituted linear or branched alkyne, substituted or unsubstituted aryl, substituted or unsubstituted Ph(CH$_2$)$_p$— wherein p is an integer between 1 and 6, substituted or unsubstituted, saturated or unsaturated cycloalkyl, substituted or unsubstituted saturated or unsaturated heterocycloalkyl or any combination thereof In one embodiment, this invention is directed to iodination of an organic compound using the N-iodoamide prepared according to the process of this invention. The iodination of organic compound refers to iododecarboxylation of carboxylic acid; to substitution of hydrogen in ketone, aliphatic, or aromatic compound with iodine; to substitution of hydrogen in the alkyl group of the alkylarene (i.e. methylarene); to substitution of hydrogen in alkane or cycloalkane or to addition of iodine atom to alkene or alkyne. The N-iodoamide prepared according to the process of this invention is used as iodination agent in radical and electrophilic reactions.

In one embodiment, an "organic compound" refers to a carboxylic acid compound, R—COOH, R—(CH$_2$)$_o$—COOH, R—CH═CH—COOH, R—C≡C—COOH, alkene, alkane, alkyne, ketone, cycloalkane, alkylarene, an aromatic compound or combination thereof; wherein o is an integer between 1 and 6 and R is substituted or unsubstituted linear or branched alkyl, substituted or unsubstituted linear or branched alkylene, substituted or unsubstituted linear or branched alkyne, substituted or unsubstituted aryl, substituted or unsubstituted, saturated or unsaturated cycloalkyl, substituted or unsubstituted saturated or unsaturated heterocycloalkyl or any combination thereof. In another embodiment, the organic compound is an alkene. In another embodiment, the organic compound is an alkane or cycloalkane. In another embodiment, the organic compound is alkylarene. In another embodiment, the organic compound is methylarene. In another embodiment, the organic compound is an aromatic compound. In another embodiment, the organic compound is a toluene. In another embodiment, the organic compound is a carboxylic acid. In another embodiment the organic compound is carboxylic acid of formula R—COOH. In another embodiment the organic compound is carboxylic acid of formula R—CH═CH—COOH. In another embodiment the organic compound is carboxylic acid of formula R—(CH$_2$)$_o$—COOH wherein o is an integer between 1 and 6. In another embodiment the organic compound is carboxylic acid of formula R—C≡C—COOH; In another embodiment, R of R—COOH, R—(CH$_2$)$_o$—COOH, R—CH═CH—COOH, R—C≡C—COOH is substituted or unsubstituted linear or branched alkyl, substituted or unsubstituted linear or branched alkylene, substituted or unsubstituted linear or branched alkyne, substituted or unsubstituted aryl, substituted or unsubstituted, saturated or unsaturated cycloalkyl, substituted or unsubstituted saturated or unsaturated heterocycloalkyl or any combination thereof. In another embodiment the organic compound is R—COOH, R—$(CH_2)_o$—COOH, R—CH=CH—COOH or R—C≡C—COOH wherein o is an integer between 1 and 6 and R is substituted or unsubstituted aryl or substituted or unsubstituted unsaturated cycloalkyl.

In one embodiment, 3-iodo-4,4-dimethyloxazolidin-2-one, and 1-iodo-3,5,5-trimethylhydantoin possess high activity as iodination agents in radical and electrophilic reactions. An important feature of the reactions is that the resulting co-products, 4,4-dimethyloxazolidin-2-one and 3,5,5-trimethylhydantoin, are soluble in water, but also can be easily recovered from aqueous solutions by extraction with organic solvents (dichloromethane, chloroform or 1,2-dichloroethane). Consequently waste water formed in the iodination reactions may be largely freed of organic impurities and the recovered amides may be used for the N-iodoamide regeneration.

In many cases, N-haloamides have tendency to isomerize under radical reaction conditions. So, N-iodosuccinimide which is useful iodinating agent is unstable under radical reaction conditions and rearrange to 3-iodopropionyl isocyanate (JACS 1985, v. 107, 6584). 1-Bromo-3,5,5-trimethylhydantoin under radical reaction conditions underwent bromine transposition from nitrogen to the 3-N-methyl group to give 3-(bromomethyl)-5,5-dimethylhydantoin (J. Heterocyclic Chem. 1982, v. 19, 1531).
Instability of N-iodoamide under the reaction conditions is serious complicating factor for amide recovery from the reaction mixture contaminated with N-iodoamide isomerization products.
Unexpectedly 1-iodo-3,5,5-trimethylhydantoin (1-ITMH), 3-iodo-4,4-dimethyloxazolidin-2-one (IDMO), and N-iodosaccharin (NISac) were not subjected to isomerization under heterolytic and radical reactions conditions that allows isolating 3,5,5-trimethylhydantoin, 4,4-dimethyloxazolidin-2-one, and saccharin from reaction mixtures in a sufficiently pure form, without the need for further purification.

In one embodiment, this invention is directed to a process for the preparation of organic iodide comprising the steps of:
(a) reacting 4,4-dimethyloxazolidin-2-one with iodine and [bis(acyloxy)iodo]arene in an aprotic solvent to yield 3-iodo-4,4-dimethyloxazolidin-2-one according to the following scheme:

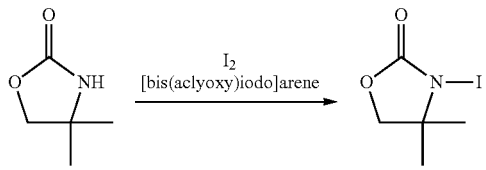

(b) reacting an organic compound with 3-iodo-4,4-dimethyloxazolidin-2-one of the step (a) to yield desired organic iodide; and
(c) recovering of 4,4-dimethyloxazolidin-2-one co-product from the reaction mixture of step (b);
wherein said organic compound of step (b) is a carboxylic acid compound, an alkane, cycloalkane, an alkylarene, an alkene, an alkyne, ketone, an aromatic compound or combination thereof. In another embodiment, the alkylarene is methylarene.

In one embodiment, this invention is directed to a process for the preparation of organic iodide comprising the steps of:
(a) reacting 3,5,5-trimethylhydantoin with iodine and [bis(acyloxy)iodo]arene in an aprotic solvent to yield 1-iodo-3,5,5-trimethylhydantoin according to the following scheme:

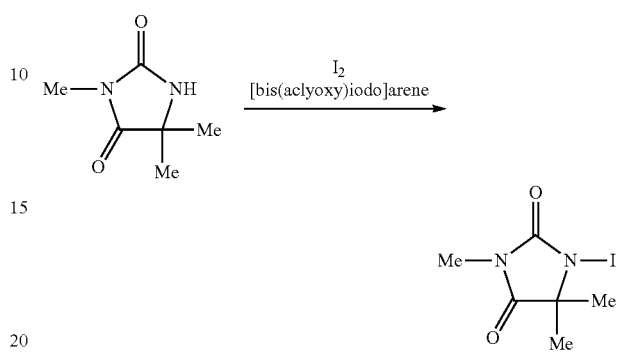

(b) reacting an organic compound with 1-iodo-3,5,5-trimethylhydantoin of the step (a) to yield desired organic iodide; and
(c) recovering 3,5,5-trimethylhydantoin co-product from the reaction mixture of step (b)
wherein said organic compound of step (b) is a carboxylic acid compound, an alkane, cycloalkane, an alkyne, ketone, an alkylarene, an alkene, an aromatic compound or combination thereof. In another embodiment, the alkylarene is methylarene.

In one embodiment, this invention is directed to a process for the preparation of organic iodide comprising the steps of:
(a) reacting saccharin with iodine and [bis(acyloxy)iodo] arene in an aprotic solvent to yield N-iodosaccharin according to the following scheme:

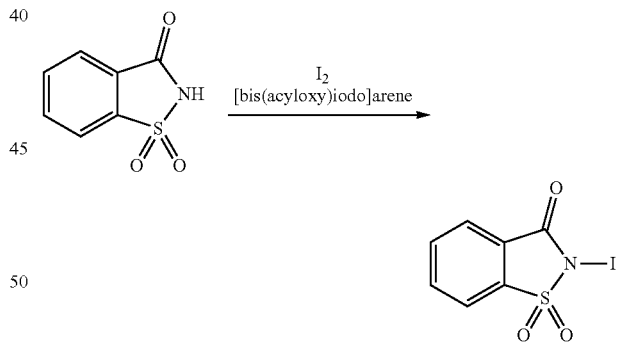

(b) reacting an organic compound with N-iodosaccharin of the step (a) to yield desired organic iodide; and
(c) recovering saccharin co-product from the reaction mixture of step (b);
wherein said organic compound of step (b) is a carboxylic acid compound, an alkane, cycloalkane, an alkyne, ketone, an alkene, an aromatic compound or combination thereof.

In one embodiment, this invention is directed to a process for the preparation of organic iodide comprising the steps of:
(a) reacting an amide with iodine and [bis(acyloxy)iodo] arene to yield N-iodoamide;
(b) reacting an organic compound with said N-iodoamide of step (a) to yield desired organic iodide; and (c) recovering said amide co-product from the reaction mixture of step (b);
wherein said amide is 4,4-dimethyloxazolidin-2-one, saccharin or 3,5,5-trimethylhydantoin and said N-iodoamide is 3-iodo-4,4-dimethyloxazolidin-2-one, N-iodosaccharin or 1-iodo-3,5,5-trimethylhydantoin;
wherein said organic compound of step (b) is a carboxylic acid compound, an alkane, cycloalkane, an alkylarene, an alkene, an alkyne, ketone, an aromatic compound or combination thereof. In another embodiment, the alkylarene is methylarene.

In one embodiment, this invention is directed to a process for the preparation of organic iodide comprising the steps of:
(a) reacting an amide with iodine and [bis(acyloxy)iodo] arene in aprotic solvent to yield N-iodoamide and iodoarene as co-product;
(b) reacting an organic compound with said N-iodoamide of step (a) to yield desired organic iodide; and
(c) recovering said amide co-product from the reaction mixture of step (b);
wherein said amide is 4,4-dimethyloxazolidin-2-one, saccharin, or 3,5,5-trimethylhydantoin and said N-iodoamide is 3-iodo-4,4-dimethyloxazolidin-2-one (IDMO), N-iodosaccharin (NIS ac), or 1-iodo-3,5,5-trimethylhydantoin (1-ITMH).

In one embodiment, the iodination reaction for the preparation of organic iodides of this invention is optionally conducted under radiation and/or heat. In another embodiment, the iodination reaction of this invention is a radical or a heterolytic/ionic reaction. In another embodiment, the iodination reaction of this invention is a radical reaction. In another embodiment, the iodination reaction of this invention is a heterolytic/ionic reaction.

A radical reaction involves radiation of the reaction mixture and/or heat. In one embodiment, the iodination reaction is optionally conducted under electromagnetic radiation. In one embodiment, the iodination reaction is optionally conducted under actinic radiation. In another embodiment, the radiation may be infrared (IR) radiation, visible radiation (light), microwave radiation, or ultraviolet (UV) radiation. In another embodiment, the electromagnetic radiation is visible light. In another embodiment, the iodination reaction is optionally conducted in the presence of electromagnetic radiation for about 1 h to about 5 h. In another embodiment, the iodination reaction is optionally conducted in the presence of electromagnetic radiation for about 1 h to about 5 h. In another embodiment, the iodination reaction is optionally conducted in the presence of electromagnetic radiation for about 1 h to about 10 h. In another embodiment, the process for the preparation of organic iodide is optionally conducted in the presence of electromagnetic radiation for about 1 h to about 15 h. In another embodiment, the radiation is tungsten or fluorescent lamp lighting.

In another embodiment, the process for the preparation of organic iodide is conducted under reflux conditions in aprotic solvent.

In one embodiment, this invention is directed to iodination of organic compound to yield organic iodide by reacting an organic compound with N-iodoamide, wherein the organic compound is a carboxylic acid compound, R—COOH, R—(CH$_2$)$_o$—COOH, R—CH═CH—COOH or R—C≡C—COOH and the iodination is substitution of carboxylic group with an iodine atom, wherein o is an integer between 1 and 6 and R is substituted or unsubstituted linear or branched alkyl, substituted or unsubstituted linear or branched alkylene, substituted or unsubstituted linear or branched alkyne, substituted or unsubstituted aryl, substituted or unsubstituted, saturated or unsaturated cycloalkyl, substituted or unsubstituted saturated or unsaturated heterocycloalkyl or any combination thereof.

In another embodiment, iododecarboxylation of organic carboxylic acid is performed according to Examples 7-13.

In another embodiment, this invention is directed to iodination of organic compound to yield organic iodide by reacting an organic compound with N-iodoamide, wherein the organic compound is alkene and the iodination is addition of iodine atom to alkene. In another embodiment, iodination of alkene is performed according to Examples 14, 15 and 16.

In another embodiment, this invention is directed to iodination of organic compound to yield organic iodide by reacting an organic compound with N-iodoamide, wherein the organic compound is an aromatic compound and the iodination is substitution of hydrogen in aromatic compound. In another embodiment, iodination of an aromatic compound is performed according to Examples 17.

In another embodiment, this invention is directed to iodination of organic compound to yield organic iodide by reacting an organic compound with N-iodoamide, wherein the organic compound is an alkylarene and iodination by substitution of the hydrogen of the aryl group is conducted by heterolytic pathway (ionic reaction which can be conducted in the dark). In another embodiment, iodination of the alkyl side chain is conducted by a radical pathway (heat, visual light irradiation). In another embodiment, iodination of an alkylarene compound is performed according to Examples 18.

In another embodiment, this invention is directed to iodination of organic compound to yield organic iodide by reacting an organic compound with N-iodoamide, wherein the organic compound is an alkane or cycloalkane and the iodination is substitution of hydrogen in the alkane or cycloalkane. In another embodiment, iodination of alkane or cycloalkane is performed according to Examples 19.

In another embodiment, this invention provides a process for the preparation of organic iodide of formula R—I comprising reacting a carboxylic acid of formula R—CO$_2$H with N-iodoamide to yield desired organic iodide and amide as co-product;
wherein said N-iodoamide is 3-iodo-4,4-dimethyloxazolidin-2-one (IDMO) or 1-iodo-3,5,5-trimethylhydantoin (1-ITMH); said amide is 4,4-dimethyloxazolidin-2-one or 3,5,5-trimethylhydantoin, respectively; wherein R is saturated, linear or branched, substituted or unsubstituted alkyl; substituted or unsubstituted aryl; substituted or unsubstituted Ph(CH$_2$)$_p$— wherein p is an integer between 1 and 6, saturated substituted or unsubstituted cycloalkyl, heterocycloalkyl or combination thereof;
wherein said reaction is radical iododecarboxylation represented by scheme (1):

$$R-CO_2H + N\text{-iodoamide} \rightarrow R-I + amide \qquad (1)$$

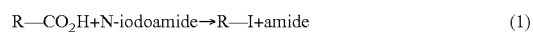

wherein said reaction is provided under visual light irradiation of the reaction mixture.

In one embodiment, this invention is directed to a process for the preparation of organic iodide comprising the steps of:
(a) reacting an amide with iodine and [bis(acyloxy)iodo] arene in aprotic solvent to yield N-iodoamide and iodoarene as co-product;
(b) reacting an organic compound with said N-iodoamide of step (a) to yield desired organic iodide and amide as co-product; and (c) recovering said amide co-product from the reaction mixture of step (b); wherein said reaction of step (b) is represented by scheme (1):

$$R-CO_2H + \text{N-iodoamide} \rightarrow R-I + \text{amide} \quad (1)$$

and said reaction is provided under visual light irradiation of the reaction mixture, wherein said organic compound is R—CO$_2$H and said N-iodoamide is 1-iodo-3,5,5-trimethylhydantoin (1-ITMH) or 3-iodo-4,4-dimethyl-2-oxazolidinone (IDMO); wherein R is saturated, linear or branched, substituted or unsubstituted alkyl; substituted or unsubstituted aryl; substituted or unsubstituted Ph(CH$_2$)$_n$— wherein o is an integer between 1 and 6, saturated, substituted or unsubstituted cycloalkyl or heterocycloalkyl or combination thereof.

In one embodiment, this invention provides a process for the preparation of iodoalkene of formula R—CH=CH—I comprising reacting an acrylic acid derivative of formula R—CH=CH—CO$_2$H with N-iodoamide to yield desired iodoalkene and amide as co-product; wherein said N-iodoamide is 3-iodo-4,4-dimethyloxazolidin-2-one (IDMO) or 1-iodo-3,5,5-trimethylhydantoin (1-ITMH); said amide is 4,4-dimethyloxazolidin-2-one or 3,5,5-trimethylhydantoin, respectively; wherein R is saturated, linear or branched, substituted or unsubstituted alkyl; substituted or unsubstituted aryl; substituted or unsubstituted Ph(CH$_2$)$_p$— wherein p is an integer between 1 and 6; saturated or unsaturated, substituted or unsubstituted cycloalkyl or heterocycloalkyl or combination thereof; wherein said reaction is electrophylic iododecarboxylation of acrylic acid derivative represented by scheme (2):

$$R-CH=CH-CO_2H + \text{N-iodoamide} \rightarrow R-CH=CH-I + \text{amide} \quad (2)$$

wherein said reaction is provided under heterolytic reaction conditions; wherein said reaction further comprises a catalyst, wherein said catalyst is an organic base, LiOAc, Bu$_4$N$^+$CF$_3$CO$_2^-$.

In one embodiment, this invention is directed to a process for the preparation of organic iodide comprising the steps of:
(a) reacting an amide with iodine and [bis(acyloxy)iodo]arene in aprotic solvent to yield N-iodoamide and iodoarene as co-product;
(b) reacting an organic compound with said N-iodoamide of step (a) to yield desired organic iodide and amide as co-product; and
(c) recovering said amide co-product from the reaction mixture of step (b);
wherein said reaction of step (b) is electrophylic iododecarboxylation of acrylic acid derivative represented by scheme (2):

$$R-CH=CH-CO_2H + \text{N-iodoamide} \rightarrow R-CH=CH-I + \text{amide} \quad (2)$$

wherein said reaction is provided under a heterolytic reaction conditions; wherein said organic compound is R—CH=CH—CO$_2$H, said N-iodoamide is 1-iodo-3,5,5-trimethylhydantoin (1-ITMH), 3-iodo-4,4-dimethyl-2-oxazolidinone (IDMO), or N-iodosaccharin (NISac); wherein said process further comprises a catalyst wherein the catalyst is organic base, LiOAc, Bu$_4$N$^+$ CF$_3$CO$_2^-$; wherein R is saturated, linear or branched, substituted or unsubstituted alkyl; substituted or unsubstituted Ph(CH$_2$)$_p$— wherein p is an integer between 1 and 6; substituted or unsubstituted aryl; saturated or unsaturated, substituted or unsubstituted cycloalkyl or heterocycloalkyl, or combination thereof.

In another embodiment, this invention provides a process for the preparation of iodoalkyne of formula R—C≡C—I comprising reacting a propiolic acid derivative of formula R—C≡C—CO$_2$H with N-iodoamide to yield desired iodoalkyne and amide as co-product; wherein said N-iodoamide is 3-iodo-4,4-dimethyloxazolidin-2-one (IDMO) or 1-iodo-3,5,5-trimethylhydantoin (1-ITMH); said amide is 4,4-dimethyloxazolidin-2-one or 3,5,5-trimethylhydantoin, respectively; wherein R is saturated, linear or branched, substituted or unsubstituted alkyl; substituted or unsubstituted aryl; substituted or unsubstituted Ph(CH$_2$)$_p$— wherein p is an integer between 1 and 6; saturated or unsaturated, substituted or unsubstituted cycloalkyl or heterocycloalkyl or combination thereof;
wherein said reaction is electrophylic iododecarboxylation of propiolic acid derivative represented by scheme (3):

$$R-C\equiv C-CO_2H + \text{N-iodoamide} \rightarrow R-C\equiv C-I + \text{amide} \quad (3)$$

wherein said reaction is provided under heterolytic reaction conditions; wherein said reaction further comprises a catalyst, wherein said catalyst is an organic base, LiOAc, Bu$_4$N$^+$CF$_3$CO$_2^-$.

In one embodiment, this invention is directed to a process for the preparation of organic iodide comprising the steps of:
(a) reacting an amide with iodine and [bis(acyloxy)iodo]arene in aprotic solvent to yield N-iodoamide and iodoarene as co-product;
(b) reacting an organic compound with said N-iodoamide of step (a) to yield desired organic iodide and amide as co-product; and
(c) recovering said amide co-product from the reaction mixture of step (b); wherein said reaction of step (b) is electrophylic iododecarboxylation of propiolic acid derivative represented by scheme (3):

$$R-C\equiv C-CO_2H + \text{N-iodoamide} \rightarrow R-CH=CH-I + \text{amide} \quad (3)$$

wherein said reaction is provided under heterolytic reaction conditions; wherein said organic compound is R—CH≡CH—CO$_2$H; said N-iodoamide is 1-iodo-3,5,5-trimethylhydantoin (1-ITMH), 3-iodo-4,4-dimethyl-2-oxazolidinone (IDMO), or N-iodosaccharin (NISac); wherein said process further comprises a catalyst wherein the catalyst is organic base, LiOAc, Bu$_4$N$^+$, CF$_3$CO$_2^-$; wherein R is saturated, linear or branched, substituted or unsubstituted alkyl; substituted or unsubstituted Ph(CH$_2$)p- wherein p is an integer between 1-6; substituted or unsubstituted aryl; saturated or unsaturated, substituted or unsubstituted cycloalkyl or heterocycloalkyl ring or combination thereof.

In another embodiment, this invention provides a process for the preparation of iodoarene of formula Ar—I comprising reacting an aromatic compound of formula Ar—H with N-iodoamide to yield desired iodoarene and amide as co-product;
wherein said N-iodoamide is 3-iodo-4,4-dimethyloxazolidin-2-one (IDMO) or 1-iodo-3,5,5-trimethylhydantoin (1-ITMH); said amide is 4,4-dimethyloxazolidin-2-one or 3,5,5-trimethylhydantoin, respectively; wherein said Ar is substituted or unsubstituted aryl group;
wherein said reaction is electrophilic aromatic iodination represented by scheme (4):

$$Ar-H + \text{N-iodoamide} \rightarrow Ar-I + \text{amide} \quad (4)$$

wherein said reaction is provided under heterolytic reaction conditions.

In one embodiment, this invention is directed to a process for the preparation of organic iodide comprising the steps of:
(a) reacting an amide with iodine and [bis(acyloxy)iodo]arene in aprotic solvent to yield N-iodoamide and iodoarene as co-product;
(b) reacting an organic compound with said N-iodoamide of step (a) to yield desired organic iodide and amide as co-product; and
(c) recovering said amide co-product from the reaction mixture of step (b);
wherein said reaction of step (b) is electrophilic aromatic iodination represented by scheme (4):

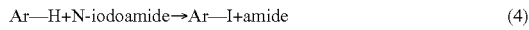

Ar—H+N-iodoamide→Ar—I+amide (4)

wherein said reaction is provided inder heterolytic reaction conditions;
wherein the organic compound is Ar—H and the N-iodoamide is 1-iodo-3,5,5-trimethylhydantoin (1-ITMH), 3-iodo-4,4-dimethyl-2-oxazolidinone (IDMO), or N-iodosaccharin (NISac); wherein said Ar is substituted or unsubstituted aryl group.

In one embodiment, this invention provides a process for the preparation of (iodomethyl)arene of formula $ArCH_2I$ comprising reacting methylarene of formula $ArCH_3$ with N-iodoamide to yield desired (iodomethyl)arene and amide as co-product;
wherein said N-iodoamide is 3-iodo-4,4-dimethyloxazolidin-2-one (IDMO) or 1-iodo-3,5,5-trimethylhydantoin (1-ITMH); said amide is 4,4-dimethyloxazolidin-2-one or 3,5,5-trimethylhydantoin, respectively; wherein said Ar is substituted or unsubstituted aryl group;
wherein said reaction is a radical iodination of methyl group of methylarene represented by scheme (5):

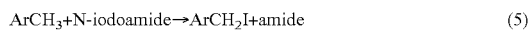

$ArCH_3$+N-iodoamide→$ArCH_2I$+amide (5)

wherein said reaction is provided under visual light irradiation of the reaction mixture.

In one embodiment, this invention is directed to a process for the preparation of organic iodide comprising the steps of:
(a) reacting an amide with iodine and [bis(acyloxy)iodo]arene in aprotic solvent to yield N-iodoamide and iodoarene as co-product;
(b) reacting an organic compound with said N-iodoamide of step (a) to yield desired organic iodide and amide as co-product; and
(c) recovering said amide co-product from the reaction mixture of step (b);
wherein said reaction of step (b) is a radical iodination of methyl group of methylarene represented by scheme (5):

$ArCH_3$+N-iodoamide→$ArCH_2I$+amide (5)

wherein said process is a radical reaction is provided under visual light irradiation of the reaction mixture, wherein said organic compound is $ArCH_3$; said N-iodoamide is 1-iodo-3,5,5-trimethylhydantoin (1-ITMH) or 3-iodo-4,4-dimethyl-2-oxazolidinone (IDMO), wherein said Ar is substituted or unsubstituted aryl group.

In one embodiment, this invention provides a process for the preparation of organic iodide of formula $R^3$—I comprising reacting $R^3$—H with N-iodoamide to yield desired organic iodide and amide as co-product;
wherein said N-iodoamide is 3-iodo-4,4-dimethyloxazolidin-2-one (IDMO) or 1-iodo-3,5,5-trimethylhydantoin (1-ITMH); said amide is 4,4-dimethyloxazolidin-2-one or 3,5,5-trimethylhydantoin, respectively; wherein said R3 is saturated, linear or branched, substituted or unsubstituted alkyl, cycloalkyl or heterocycloalkyl;

wherein said reaction is a radical iodination of alkane or cycloalkane represented by scheme (6):

$R^3$—H+N-iodoamide→$R^3$—I+amide (6)

wherein said reaction is provided under visual light irradiation of the reaction mixture.

In one embodiment, this invention is directed to a process for the preparation of organic iodide comprising the steps of:
(a) reacting an amide with iodine and [bis(acyloxy)iodo]arene in aprotic solvent to yield N-iodoamide and iodoarene as co-product;
(b) reacting an organic compound with said N-iodoamide of step (a) to yield desired organic iodide and amide as co-product; and
(c) recovering said amide co-product from the reaction mixture of step (b);
wherein the reaction of step (b) is a radical iodination of alkane or cycloalkane represented by scheme (6):

$R^3$—H+N-iodoamide→$R^3$—I+amide (6)

wherein said reaction is provided under visual light irradiation of the reaction mixture; wherein said organic compound is $R^3$—H; said N-iodoamide is 1-iodo-3,5,5-trimethylhydantoin (1-ITMH) or 3-iodo-4,4-dimethyl-2-oxazolidinone (IDMO), and said $R^3$ is saturated, linear or branched, substituted or unsubstituted alkyl cycloalkyl or heterocycloalkyl.

In one embodiment, this invention provides a process for the preparation of organic iodide of formula $RCHXCHIR^1$ comprising reacting an alkene of formula $RCH=CHR^1$ and compound of formula HX with N-iodoamide to yield desired organic iodide and amide as co-product;
wherein said N-iodoamide is 3-iodo-4,4-dimethyloxazolidin-2-one (IDMO) or 1-iodo-3,5,5-trimethylhydantoin (1-ITMH); said amide is 4,4-dimethyloxazolidin-2-one or 3,5,5-trimethylhydantoin, respectively; wherein R is saturated, linear or branched, substituted or unsubstituted alkyl; substituted or unsubstituted $Ph(CH_2)_p$— wherein said p is an integer between 1 and 6; substituted or unsubstituted aryl; saturated or unsaturated, substituted or unsubstituted cycloalkyl or heterocycloalkyl; $R^1$ is hydrogen, saturated, linear or branched, substituted or unsubstituted alkyl; substituted or unsubstituted aryl; substituted or unsubstituted $Ph(CH_2)_t$— wherein t is an integer between 1 and 6; saturated or unsaturated, substituted or unsubstituted cycloalkyl or heterocycloalkyl; and R and $R^1$ optionally form a ring; wherein X is OH, halogen, alkoxy or acyloxy group;
wherein said reaction is electrophilic iodination of alkene represented by scheme (7):

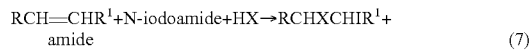

$RCH=CHR^1$+N-iodoamide+HX→$RCHXCHIR^1$+amide (7)

wherein said reaction is provided under heterolytic reaction conditions.

In one embodiment, this invention is directed to a process for the preparation of organic iodide comprising the steps of:
(a) reacting an amide with iodine and [bis(acyloxy)iodo]arene in aprotic solvent to yield N-iodoamide and iodoarene as co-product;
(b) reacting an organic compound with said N-iodoamide of step (a) to yield desired organic iodide and amide as co-product; and
(c) recovering said amide co-product from the reaction mixture of step (b);

wherein said reaction of step (b) is electrophilic iodination of alkene represented by scheme (7):

$$RCH{=}CHR^1 + \text{N-iodoamide} + HX \rightarrow RCHXCHIR^1 + \text{amide} \quad (7)$$

wherein said reaction is provided under heterolytic reaction conditions; and wherein said organic compound is $RCH{=}CHR^1$; said N-iodoamide is 1-iodo-3,5,5-trimethylhydantoin (1-ITMH), 3-iodo-4,4-dimethyl-2-oxazolidinone (IDMO), or N-iodosaccharin (NISac); wherein X is OH, halogen, alkoxy or acyloxy group; and R is saturated, linear or branched, substituted or unsubstituted alkyl; substituted or unsubstituted aryl; substituted or unsubstituted $Ph(CH_2)o$- wherein o is an integer between 1-6; saturated or unsaturated, substituted or unsubstituted cycloalkyl or heterocycloalkyl; $R^1$ is hydrogen, saturated, linear or branched, substituted or unsubstituted alkyl; substituted or unsubstituted aryl; substituted or unsubstituted $Ph(CH_2)t$- wherein t is an integer between 1-6; saturated or unsaturated, substituted or unsubstituted cycloalkyl or heterocycloalkyl, and R and $R^1$ optionally form a ring.

In another embodiment, this invention provides a process for the preparation of iodoalkene of formula $RCX{=}CIR^1$ or its tautomer (when X is OH) comprising reacting an alkyne of formula $RC{\equiv}CR^1$ with N-iodoamide and compound of formula HX to yield desired iodoalkene and amide as co-product; wherein said N-iodoamide is 3-iodo-4,4-dimethyloxazolidin-2-one (IDMO) or 1-iodo-3,5,5-trimethylhydantoin (1-ITMH); said amide is 4,4-dimethyloxazolidin-2-one or 3,5,5-trimethylhydantoin, respectively; wherein R is saturated, linear or branched, substituted or unsubstituted alkyl; substituted or unsubstituted $Ph(CH_2)_o$— wherein said o is an integer between 1 and 6; substituted or unsubstituted aryl; saturated or unsaturated, substituted or unsubstituted cycloalkyl or heterocycloalkyl; $R^1$ is hydrogen, saturated, linear or branched, substituted or unsubstituted alkyl; substituted or unsubstituted aryl; substituted or unsubstituted $Ph(CH_2)_t$— wherein t is an integer between 1 and 6; saturated or unsaturated, substituted or unsubstituted cycloalkyl or heterocycloalkyl; wherein X is halogen, OH alkoxy or acyloxy group;

wherein said reaction is electrophilic iodination of alkyne represented by scheme (8):

$$RC{\equiv}CR^1 + \text{N-iodoamide} + HX \rightarrow RCX{=}CIR^1 + \text{amide} \quad (8)$$

wherein said reaction is provided under heterolytic reaction conditions.

In one embodiment, this invention is directed to a process for the preparation of organic iodide comprising the steps of:
(a) reacting an amide with iodine and [bis(acyloxy)iodo] arene in aprotic solvent to yield N-iodoamide and iodoarene as co-product;
(b) reacting an organic compound with said N-iodoamide of step (a) to yield desired organic iodide and amide as co-product; and
(c) recovering said amide co-product from the reaction mixture of step (b); wherein said reaction of step (b) is electrophilic iodination of alkyne represented by scheme (8):

$$RC{\equiv}CR^1 + \text{N-iodoamide} + HX \rightarrow RCX{=}CIR^1 + \text{amide} \quad (8)$$

wherein said reaction is provided under heterolytic reaction conditions; and wherein said organic compound is $RC{\equiv}CR^1$; said N-iodoamide is 1-iodo-3,5,5-trimethylhydantoin (1-ITMH), 3-iodo-4,4-dimethyl-2-oxazolidinone (IDMO), or N-iodosaccharin (NISac); wherein X is OH, halogen, alkoxy or acyloxy group; and R is saturated, linear or branched, substituted or unsubstituted alkyl; substituted or unsubstituted aryl; substituted or unsubstituted $Ph(CH_2)$ o- wherein o is an integer between 1-6; saturated or unsaturated, substituted or unsubstituted cycloalkyl or heterocycloalkyl; $R^1$ is hydrogen, saturated, linear or branched, substituted or unsubstituted alkyl; substituted or unsubstituted aryl; substituted or unsubstituted $Ph(CH_2)t$- wherein t is an integer between 1-6; saturated or unsaturated, substituted or unsubstituted cycloalkyl or heterocycloalkyl, and R and $R^1$ optionally form a ring.

In another embodiment, this invention provides a process for the preparation of α-iodoketone of formula $RCOCHIR^1$ comprising reacting an ketone of formula $RCOCH_2R^1$ with N-iodoamide to yield desired α-iodoketone and amide as co-product;

wherein said N-iodoamide is 3-iodo-4,4-dimethyloxazolidin-2-one (IDMO) or 1-iodo-3,5,5-trimethylhydantoin (1-ITMH); said amide is 4,4-dimethyloxazolidin-2-one or 3,5,5-trimethylhydantoin, respectively; wherein R is saturated, linear or branched, substituted or unsubstituted alkyl; substituted or unsubstituted $Ph(CH_2)_p$— wherein said p is an integer between 1 and 6; substituted or unsubstituted aryl; saturated or unsaturated, substituted or unsubstituted cycloalkyl or heterocycloalkyl; $R^1$ is hydrogen, saturated, linear or branched, substituted or unsubstituted alkyl; substituted or unsubstituted aryl; substituted or unsubstituted $Ph(CH_2)_t$— wherein t is an integer between 1 and 6; saturated or unsaturated, substituted or unsubstituted cycloalkyl or heterocycloalkyl; and R and $R^1$ optionally form a ring;

wherein said reaction is electrophilic iodination of ketone represented by scheme (9):

$$RCOCH_2R^1 + \text{N-iodoamide} \rightarrow RCOCHIR^1 + \text{amide} \quad (9)$$

wherein said reaction is provided under heterolytic reaction conditions.

In one embodiment, this invention is directed to a process for the preparation of organic iodide comprising the steps of:
(a) reacting an amide with iodine and [bis(acyloxy)iodo] arene in aprotic solvent to yield N-iodoamide and iodoarene as co-product;
(b) reacting an organic compound with said N-iodoamide of step (a) to yield desired organic iodide and amide as co-product; and
(c) recovering said amide co-product from the reaction mixture of step (b); wherein said reaction of step (b) is electrophilic iodination of ketone represented by scheme (9):

$$RCOCH_2R^1 + \text{N-iodoamide} \rightarrow RCOCHIR^1 + \text{amide} \quad (9)$$

wherein said reaction is provided under heterolytic reaction conditions; and wherein said organic compound is $RCOCH_2R^1$; said N-iodoamide is 1-iodo-3,5,5-trimethylhydantoin (1-ITMH), 3-iodo-4,4-dimethyl-2-oxazolidinone (IDMO), or N-iodosaccharin (NISac); wherein X is OH, halogen, alkoxy or acyloxy group; and R is saturated, linear or branched, substituted or unsubstituted alkyl; substituted or unsubstituted aryl; substituted or unsubstituted $Ph(CH_2)$ o- wherein o is an integer between 1-6; saturated or unsaturated, substituted or unsubstituted cycloalkyl or heterocycloalkyl; $R^1$ is hydrogen, saturated, linear or branched, substituted or unsubstituted alkyl; substituted or unsubstituted aryl; substituted or unsubstituted $Ph(CH_2)t$- wherein t is an integer between 1-6; saturated or unsaturated, substituted or unsubstituted cycloalkyl or heterocycloalkyl, and R and $R^1$ optionally form a ring.

In one embodiment, this invention is directed to iodination of an organic compound comprising reacting an organic compound with N-iodoamide prepared according to the process of this invention and recovering the amide co-product from the reaction mixture. In another embodiment, the N-iodoamide is 3-iodo-4,4-dimethyloxazolidin-2-one (IDMO) and the recovered amide is 4,4-dimethyloxazolidin-2-one (DMO). In another embodiment, the N-iodoamide is 3-iodo-1,5,5-trimethylhydantoin or 1-iodo-3,5,5-trimethylhydantoin (1-ITMH) and the recovered amide is 1,5,5-trimethylhydantoin and 3,5,5-trimethylhydantoin (TMH), respectively. In another embodiment, the recovered amide is further used for the preparation of N-iodoamide according to the process of this invention.

In one embodiment, the process for the preparation of organic iodide comprising a recovery step of the amide. In another embodiment, the amide is recovered from aqueous solutions by extraction with dichloromethane, chloroform or 1,2-dichloroethane.

In another embodiment, the recovery of DMO from iododecarboxylation process of organic acid using IDMO as an N-iodoamide is according to Example 8.

In another embodiment, the recovery of DMO from iodination of alkene using IDMO as an N-iodoamide is according to Example 14.

In another embodiment, the recovery of DMO from iodination of an aromatic compound using IDMO as an N-iodoamide is according to Example 17.

In another embodiment, the recovery of 3,5,5-TMH from iododecarboxylation process of organic acid using 1-ITMH as an N-iodoamide is according to Example 9.

In another embodiment, the recovery of 3,5,5-TMH from iodination of alkene using 1-ITMH as an N-iodoamide is according to Example 15.

In another embodiment, the recovery of 3,5,5-TMH from iodination of aromatic compound using 1-ITMH as an N-iodoamide is according to Example 17.

The term "about" as used herein means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to about 5%, up to about 10% or up to about 20% of a given value.

The term "organic iodide" refers to a compound in which one or more carbon atoms are linked by covalent bonds with one or more iodine atoms.

An "alkyl" refers, in one embodiment, to saturated aliphatic groups including straight-chain, branched-chain or cyclic. The groups derived by removal of a hydrogen atom from a terminal carbon atom of unbranched alkanes form a subclass of normal alkyl (n-alkyl) groups: The groups $RCH_2$—, $R_2CH$— (R≠H), and $R_3C$— (R≠H) are primary, secondary and tertiary alkyl groups respectively. In one embodiment, the alkyl group has 1-20 carbons. In another embodiment, the alkyl group has 10-20 carbons. In another embodiment, the alkyl group has 1-6 carbons. In another embodiment, the alkyl group has 2-7 carbons. In another embodiment, the cyclic alkyl group has 3-8 carbons. In another embodiment, the cyclic alkyl group has 3-12 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or unsubstituted by one or more groups selected from halogen, phenyl, aryl, haloalkyl, protected hydroxyl, cyano, azide, carboxylic acid, aldehyde, alkoxy, carbonyl, amido, alkylamido, nitro, protected amino, alkylamino, protected thio and/or thioalkyl.

The term "alkenyl" refer to an unsaturated aliphatic group (as defined above for "alkyl) having at least one double bond.

The term "akynyl" refer to an unsaturated aliphatic group (as defined above for "alkyl/alkane) having at least one triple bond.

An "aryl" refer, in one embodiment, to conjugated planner ring. In another embodiment, the "aryl", may be unsubstituted or substituted by one or more groups selected from halogen, aryl, haloalkyl, protected hydroxyl, cyano, azide, carboxylic acid, aldehyde, alkoxy, carbonyl, amido, alkylamido, nitro, protected amino, alkylamino, protected thio and/or thioalkyl. Nonlimiting examples of "aryl", groups are phenyl, tolyl, pyridyl, naphthyl, biphenyl, pyrrolyl, pyrazinyl, pyrimidinyl, pyrazolyl, pyridinyl, furanyl, thiophenyl, thiazolyl, imidazolyl, isoxazolyl, and the like.

A "cycloalkyl" refers to a saturated carbocyclic one or more rings consisting of the carbon and hydrogen elements. Non limiting examples of cycloalkyl include: cyclobutyl, norbornyl, cyclopentyl and cyclohexyl. In one embodiment, they may be unsubstituted or substituted by one or more groups selected from halogen, alkyl, aryl, haloalkyl, protected hydroxyl, cyano, azide, carboxylic acid, aldehyde, alkoxy, carbonyl, amido, alkylamido, nitro, protected amino, alkylamino, protected thio- and/or thioalkyl.

A "heterocycloalkyl" refers to cycloalakyl as described above wherein one of the carbon atoms is replaced by at least one of nitrogen, sulfur, oxygen, phosphorous or combination thereof.

The term "alkylarene" refer to an arene substituted with an alkyl group. The term "methylarene" refer to an arene substituted with a methyl group. Suitable methylarene include toluene, o-, m- or p-xylene, mesitylene, durene, o-, m- or p-chlorotoluene, o-, m- or p-nitrotoluene, and the like, all of which may be optionally substituted.

The term "organic base" refers to a tertiary amine (trialkylamine), and N-heterocyclic compound (N-alkylpiperidine, N-alkylpyrrolidine, N-alkylmorpholine), non limiting examples of an organic base includes triethylamine ($Et_3N$), N,N-diisopropylethylamine, N-methylpiperidine, N-ethylpiperidine, N-methylpyrrolidine, N-ethylpyrrolidine, N-methylmorpholine, N-ethylmorpholine, 1,8-diazabicyclo[5.4.0]undec-7-ene (DBU), 1,5-diazabicyclo[4.3.0]non-5-ene (DBN), 1,4-diazabicyclo[2.2.2]octane. In another embodiment, the organic base is triethylamine ($Et_3N$). In another embodiment, the organic base is N,N-diisopropylethylamine.

In one embodiment, the term "a" or "one" or "an" refers to at least one. In one embodiment the phrase "two or more" may be of any denomination, which will suit a particular purpose. In one embodiment, "about" or "approximately" may comprise a deviance from the indicated term of +1%, or in some embodiments, −1%, or in some embodiments, ±2.5%, or in some embodiments, ±5%, or in some embodiments, ±7.5%, or in some embodiments, ±10%, or in some embodiments, ±15%, or in some embodiments, ±20%, or in some embodiments, ±25%.

The following examples are presented in order to more fully illustrate the preferred embodiments of the invention. They should in no way, however, be construed as limiting the broad scope of the invention.

EXAMPLES

Experimental Details

Reagents:

All reagents and solvents were purchased from Aldrich Chemical Company unless specified otherwise and used without further purification.

Techniques:

All reactions were performed under nitrogen atmosphere in non-flame dried glassware. Conversions were determined by $^1$H NMR, and yields of isolated product refer to products with more than 95% purity by $^1$H NMR. Flash column chromatography was performed employing 63-200 μm silica gel 60 according to standard techniques (*J. Org. Chem.* 1978, v. 43, 2923).

Analytical Methods:

GC analyses were performed on Shimadzu GC-2010 gas chromatograph with flame ionization detector (FID) using a 30 m×0.25 mm Quadrex capillary column with methyl 5% phenyl silicone stationary phase, 0.25 μm film thickness. For TLC analysis, Merck precoated TLC plates (silica gel 60 F-254 on glass plates, 0.25 mm) were used. NMR spectra were recorded on a Bruker AM-400 ($^1$H at 400 MHz, $^{13}$C at 100 MHz) instruments using CDCl$_3$ (unless otherwise stated) as a solvent. Data are reported as follows: chemical shift in ppm relative to internal TMS, multiplicity, coupling constant in Hz and integration. Compounds described in the literature were characterized by comparing their $^1$H and/or $^{13}$C NMR spectra to the previously reported data. New compounds were further characterized by high-resolution mass spectra.

Powder x-ray diffraction patterns (XRPD) were obtained using RikaguSmartLab x-ray diffractometer.

Melting points were determined in open capillary tubes with Stuart SMP1 melting point apparatus and are uncorrected. The melting points generally depend on the purity level of the samples.

Measurements of difference between the temperature of a sample and a reference pan that are subject to the same temperature program (differential scanning calorimetry, DSC) were obtained on a TA Instruments Q10 Differential Scanning calorimeter.

The following abbreviations are used:
Alk=alkyl
Ar=aryl
d=doublet
DCE=1,2-dichloroethane
DCM=dichloromethane
DIH=1,3-diiodo-5,5-dimethylhydantoin
DMO=4,4-dimethyl-2-oxazolidinone or 4,4-dimethyloxazolidin-2-one
DSC=differential scanning calorimetry
FL=fluorescent lighting
IDMO=3-iodo-4,4-dimethyl-2-oxazolidinone or 3-iodo-4,4-dimethyloxazolidin-2-one
INPT=N-iodo-4-nitrophthalimide
IPT=N-iodophthalimide
1-ITMH=1-iodo-3,5,5-trimethylhydantoin
3-ITMH=3-iodo-1,5,5-trimethylhydantoin
m=multiplet
"N—I"=N-iodo reagent
N-iodoamide=iodoamide, wherein iodine atom is attached directly to nitrogen atom
NIS=N-iodosuccinimide
NISac=N-iodosaccharine
NL=dark
ORTEP=Oak Ridge Thermal-Ellipsoid Plot Program for crystal structure illustrations
PhI(OAc$_F$)$_2$=[bis(trifluoroacetoxy)iodo]benzene
rt=room temperature
s=singlet
t=triplet
TL=tungsten lamp irradiation
1,5,5-TMH=1,5,5-trimethylhydantoin
3,5,5-TMH=3,5,5-trimethylhydantoin
XRPD=x-ray powder diffraction
hv=visual light irradiation
Δ=heating

Example 1

Preparation of DMO and 3,5,5-TMH

Preparation of 4,4-dimethyloxazolidin-2-one (DMO)

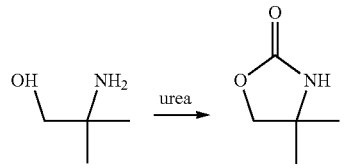

A mixture of 2-amino-2-methyl-1-propanol (10.0 g, 112 mmole) and urea (13.5 g, 224 mmole) was heated for 1 h at 170-180° C., for 1 h at 210-220° C., cold to rt and dissolved in water (50 mL). The solution was extracted with DCM (5×50 mL). The combined extracts were dried over Na$_2$SO$_4$, filtered and concentrated in vacuo to afford 10.3 g (80%) of 4,4-dimethyloxazolidin-2-one. $^1$H NMR (CDCl$_3$): δ 6.13 (br s, 1H, NH), 4.07 (s, 2H, CH$_2$), 1.32 (s, 6H, 2 CH$_3$) ppm. $^{13}$C NMR (CDCl$_3$) δ 159.4, 77.1, 55.4, 27.7 ppm.

Preparation of 3,5,5-trimethylhydantoin (3,5,5-TMH)

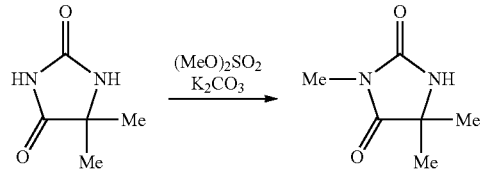 [SMILES: CC1(C)NC(=O)NC1=O ; CN1C(=O)NC(C)(C)C1=O]

A mixture of 5,5-dimethylhydantoin (12.8 g, 100 mmol), (MeO)$_2$SO$_2$ (12.0 g, 95 mmol), K$_2$CO$_3$ (20.7 g, 150 mmol) and acetone (200 mL) was stirred for 16 h at rt and concentrated in vacuo. Aqueous solution of the residue was extracted with DCM (3×50 mL). Combine organic extracts were washed with water (50 mL), dried over Na$_2$SO$_4$, filtered and concentrated in vacuo to give 11.8 g (83%) of 3,5,5-trimethylhydantoin. $^1$H NMR δ: 6.49 (br s, 1H), 3.00 (s, 3H, CH$_3$), 1.43 (s, 6H, 2 CH$_3$) ppm. $^{13}$C NMR δ: 177.6, 157.0, 59.0, 25.1, 24.7 ppm.

Preparation of 3,5,5-trimethylhydantoin (3,5,5-TMH)

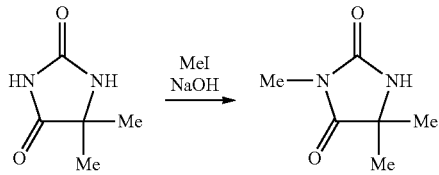 [SMILES: CC1(C)NC(=O)NC1=O ; CN1C(=O)NC(C)(C)C1=O]

MeI (7.5 mL, 0.12 mol) was added dropwise to the stirred mixture of 5,5-dimethylhydantoin (12.8 g, 0.10 mol), 50% aq NaOH (8.0 g, 0.10 mol), and EtOH (70 mL) at rt. The obtained mixture was stirred for 2 h at rt, for 3 h at 60° C. and concentrated in vacuo. A solution of the residue in water (50 mL) was extracted with $CHCl_3$ (2×50 mL). The combined organic extracts were washed with water (50 mL), dried over $Na_2SO_4$, filtered and concentrated in vacuo. The residue was recrystallized from water, giving 12.4 g (87%) of 3,5,5-trimethylhydantoin.

Example 2

Crystal of 3,5,5-trimethylhydantoin (3,5,5-TMH)

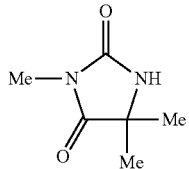

3,5,5-Trimethylhydantoin (0.2 g) was dissolved in acetone (2 mL). The solvents were slowly evaporated from the mixture at rt on the air to give 0.60×0.114×0.093 mm crystal of 3,5,5-trimethylhydantoin. The crystalline 3,5,5-trimethylhydantoin is characterized by a single x-ray crystallographic analysis at 200(2) K, which yields crystal parameters (Table 2.1), atomic positions of all atoms relative to the origin of the unit cell (Table 2.2), bond lengths (Table 2.3), and bond angles (Table 2.4).

TABLE 2.1

Crystal parameters of 3,5,5-trimethylhydantoin

| | |
|---|---|
| Formula | $C_6H_{10}N_2O_2$ |
| Formula weight (amu) | 142.16 |
| Crystal system | Monoclinic |
| Space group | P 21/n |
| Cell dimensions | |
| a (Å) | 9.3210(3) |
| b (Å) | 8.2470(3) |
| c (Å) | 9.5290(3) |
| α = γ (°) | 90 |
| β (°) | 96.993(2) |
| V (Å³) | 727.05(4) |
| Z (molecules/units cell) | 4 |
| Density (g/cm3) | 1.299 |

The unit cell dimension is defined by three parameters: length of the sides of the cell, relative angles of sides to each other and the volume of the cell. The lengths of the sides of the unit cell are defined by a, b and c. The relative angles of the cell sides are defined by α, β and γ. The volume of the cell is defined as V.

Figure 9:
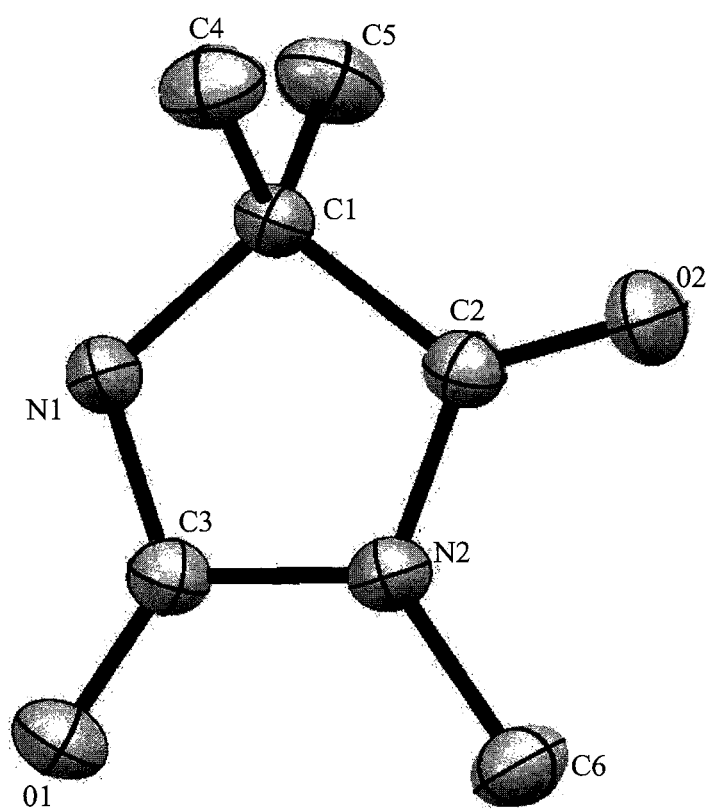
FIG. 9 depicts an Oak Ridge Thermal-Ellipsoid Plot Program (ORTEP) view of 3,5,5-trimethylhydantoin molecule and the atomic numbering of non-hydrogen atoms as derived from single crystal x-ray analysis of the crystalline 3,5,5-trimethylhydantoin.

FIG. 9 depict the ORTEP view of 3,5,5-trimethylhydantoin molecule and the atomic numbering of non-hydrogen atoms as derived from single crystal x-ray analysis of the crystalline 3,5,5-trimethylhydantoin.

TABLE 2.2

Atomic coordinates (×10⁴) and equivalent isotropic displacement parameters (Å² × 10³) for the crystalline 3,5,5-trimethylhydantoin. U(eq) is defined as one third of the trace of the orthogonalized Uij tensor.

| | X | Y | Z | U(eq) |
|---|---|---|---|---|
| O(1) | 5111(2) | 3090(2) | 2343(2) | 42(1) |
| O(2) | 9150(2) | 2411(2) | 126(2) | 42(1) |
| N(1) | 6468(2) | 829(2) | 1981(2) | 31(1) |
| N(2) | 7171(2) | 3180(2) | 1188(2) | 29(1) |
| C(1) | 7722(2) | 420(2) | 1268(2) | 26(1) |
| C(2) | 8146(2) | 2090(2) | 772(2) | 27(1) |
| C(3) | 6132(2) | 2402(2) | 1896(2) | 28(1) |
| C(4) | 7302(2) | −680(2) | −1(2) | 37(1) |
| C(5) | 8932(2) | −315(3) | 2290(2) | 37(1) |
| C(6) | 7174(2) | 4916(2) | 891(2) | 36(1) |

TABLE 2.3

Bond lengths (Å) for 3,5,5-trimethylhydantoin molecule

| | |
|---|---|
| O(1)—C(3) | 1.228(2) |
| O(2)—C(2) | 1.211(2) |
| N(1)—C(3) | 1.334(2) |
| N(1)—C(1) | 1.462(2) |
| N(1)—H(1) | 1.00(3) |
| N(2)—C(2) | 1.370(2) |
| N(2)—C(3) | 1.401(2) |
| N(2)—C(6) | 1.459(2) |
| C(1)—C(5) | 1.523(2) |
| C(1)—C(2) | 1.524(2) |
| C(1)—C(4) | 1.524(2) |

TABLE 2.4

Angles (°) for 3,5,5-trimethylhydantoin molecule

| | |
|---|---|
| C(3)—N(1)—C(1) | 113.02(15) |
| C(3)—N(1)—H(1) | 122.1(15) |
| C(1)—N(1)—H(1) | 123.5(15) |
| C(2)—N(2)—C(3) | 111.10(15) |
| C(2)—N(2)—C(6) | 124.78(15) |
| C(3)—N(2)—C(6) | 124.09(15) |
| N(1)—C(1)—C(5) | 111.52(15) |
| N(1)—C(1)—C(2) | 100.79(13) |
| C(5)—C(1)—C(2) | 111.02(15) |
| N(1)—C(1)—C(4) | 111.30(15) |
| C(5)—C(1)—C(4) | 111.66(15) |
| C(2)—C(1)—C(4) | 110.07(15) |
| O(2)—C(2)—N(2) | 125.76(17) |
| O(2)—C(2)—C(1) | 126.93(16) |
| N(2)—C(2)—C(1) | 107.31(14) |
| O(1)—C(3)—N(1) | 127.85(17) |
| O(1)—C(3)—N(2) | 124.45(17) |
| N(1)—C(3)—N(2) | 107.71(15) |

Example 3

Recovery of Amides from Aqueous Solution

A mixture of amide (weight of amide (W): 0.2-0.5 g), water (20-100 mL) and water immiscible organic solvent (the same volume as water) was stirred at 25° C. for 0.5 h. The organic layer was thoroughly separated, dried over $Na_2SO_4$, filtered and concentrated in vacuo to recover the amide. Distribution coefficient K was calculated according to the formula $K=W_o/W-W_o$, where $W_o$ is weight of the recovered amide in g. Distribution coefficients of 3,5,5-trimethylhydantoin (3,5,5-TMH), 4,4-dimethyloxazolidin-2-one (DMO), 5,5-dimethylhydantoin (DMH) and succinimide in hexane, benzene, $CCl_4$ and DCM are shown in Table 3.1.

TABLE 3.1

Distribution coefficients (K) of amides in organic solvents at 25° C.

| solvent | succinimide | DMH | 3,5,5-TMH | DMO |
|---|---|---|---|---|
| hexane | 0.1≤ | 0.1≤ | 0.1≤ | 0.1≤ |
| PhH | 0.1≤ | 0.1≤ | 0.1≤ | 0.1≤ |
| $CCl_4$ | 0.1≤ | 0.1≤ | 0.1≤ | 0.1≤ |
| DCM | 0.1≤ | 0.1≤ | 1.6 | 0.5 |

The larger the value of distribution coefficient, the more amide will be transferred to the solvent with each extraction, and the fewer portions of the solvent will be required for essentially complete removal of the amide from aqueous solution. 3,5,5-Trimethylhydantoin (3,5,5-TMH) and, in a less degree, 4,4-dimethyloxazolidin-2-one (DMO) can be extracted from the aqueous solutions with dichloromethane.

Example 4

Preparation of N-Iodoamides

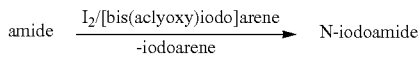

Note: All the reactions were provided in the dark

Preparation of 3-iodo-4,4-dimethyloxazolidin-2-one Using PhI(OAc)$_2$ and Recovery of Iodobenzene

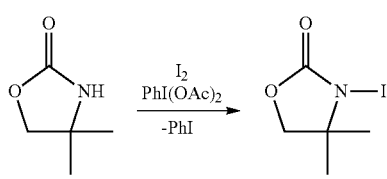

$I_2$ (9.4 g, 36.9 mmol) was added to the stirred mixture of 4,4-dimethyloxazolidin-2-one (6.5 g, 56.7 mmol), PhI (OAc)$_2$ (11.0 g, 34.0 mmol), and MeCN (120 mL). The mixture was stirred for 3 h at rt. MeCN was evaporated under reduced pressure from the mixture. CCl$_4$ (120 mL) was added to the residue and the obtained mixture was stirred for 15 min at rt and for 1 h at 0 to 5° C. The precipitated solid was filtered, washed on the filter with cold CCl$_4$* and dried in vacuo to give 11.0 g (80%) of 3-iodo-4,4-dimethyloxazolidin-2-one as off-white crystalline powder. Mp 148-9° C. (dec); $^1$H NMR: δ 4.24 (s, 2H, CH$_2$), 1.14 (s, 6H, 2 CH$_3$) ppm; $^{13}$C NMR: δ 158.3, 74.6, 62.0, 26.0 ppm; HRMS-ESI: (M+H)$^+$241.9678, C$_5$H$_9$NO$_2$I calc mass 241.9678.

*The filtrates were washed with 1 M aq Na$_2$SO$_3$ (2×50 mL), dried (Na$_2$SO$_4$) and filtered. CCl$_4$ was evaporated under reduced pressure from the filtrates to give PhI in the residue.

Figure 2:
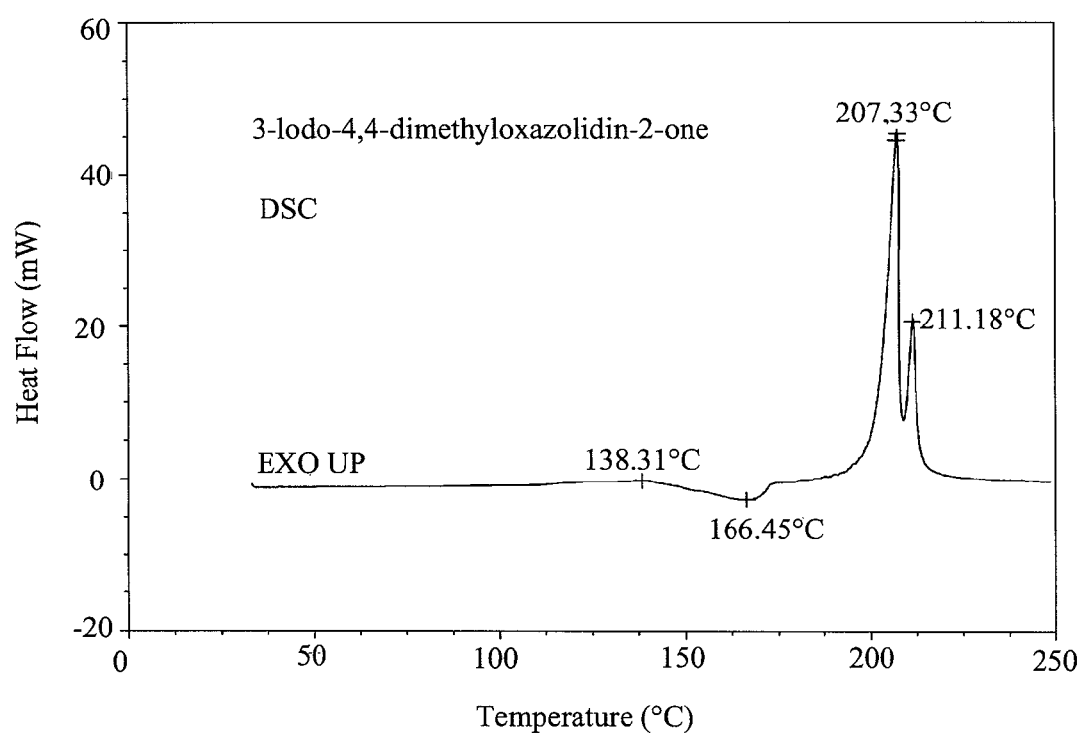
FIG. 2 depicts differential scanning calorimetry (DSC) curve of 3-iodo-4,4-dimethyloxazolidin-2-one. Heat flow 5°/min.
Figure 7:
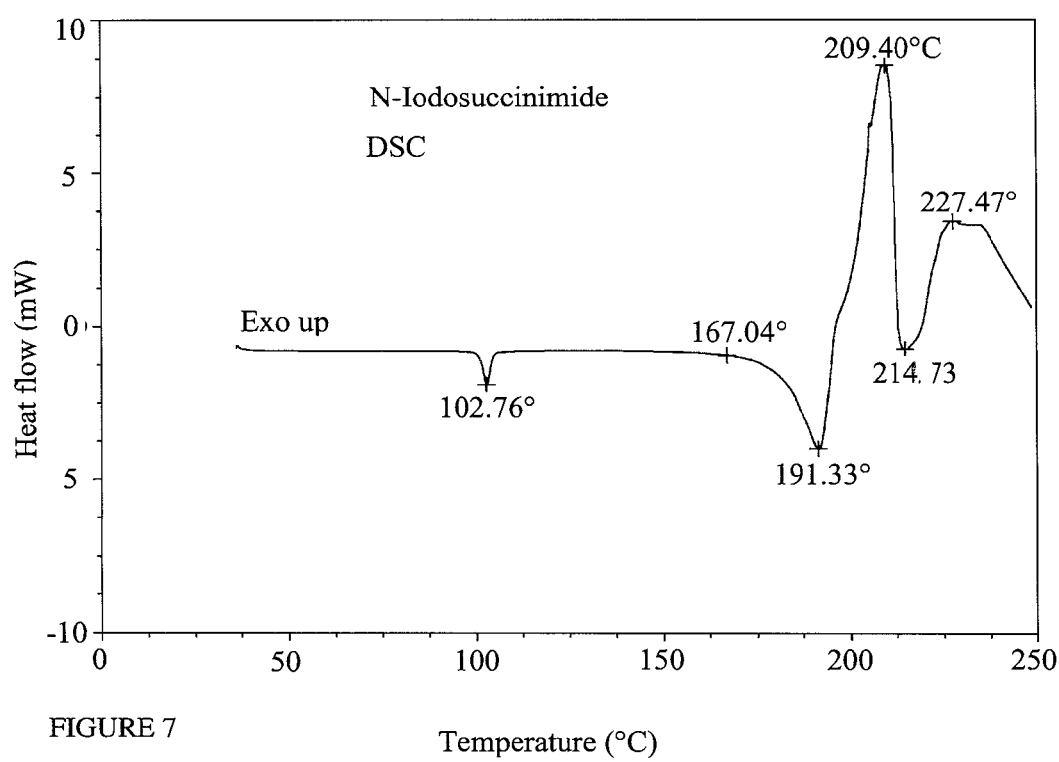
FIG. 7 depicts differential scanning calorimetry (DSC) curve of N-iodosuccinimide. Heat flow 5°/min.

FIG. 2 depicts differential scanning calorimetry (DSC) curve of the crystalline 3-iodo-4,4-dimethyloxazolidin-2-one. For comparison see differential scanning calorimetry curve of N-iodosuccinimide (FIG. 7).

Preparation of 3-iodo-4,4-dimethyloxazolidin-2-one Using Benzene as Solvent

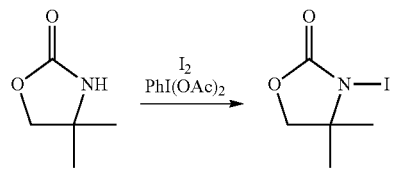

$I_2$ (1.53 g, 6.02 mmol) was added to the stirred mixture of 4,4-dimethyloxazolidin-2-one (1.07 g, 9.25 mmol), PhI (OAc)$_2$ (1.79 g, 5.55 mmol), and benzene (20 mL). The mixture was stirred for 60 h at rt and 1 h at 0 to 5° C. The precipitated solid was filtered, washed on the filter with cold benzene and dried in vacuo to give 1.64 g (75%) of 3-iodo-4,4-dimethyloxazolidin-2-one as off-white crystalline powder.

Preparation of 3-iodo-4,4-dimethyloxazolidin-2-one Using bis(trifluoroacetoxy)iodo]benzene

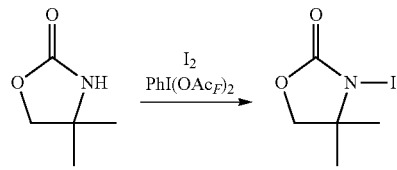

A mixture of 4,4-dimethyloxazolidin-2-one (0.50 g, 4.3 mmol), [bis(trifluoroacetoxy)iodo]benzene (1.12 g, 2.6 mmol), I$_2$ (0.72 g, 2.8 mmol) and MeCN (10 mL) was stirred at rt for 3 h and concentrated in vacuo. CCl$_4$ (10 mL) was added to the residue and the obtained mixture was stirred for 15 min at rt and 1 h at 0 to 5° C. The precipitated solid was filtered, washed on the filter with cold CCl$_4$ and dried in vacuo to give 0.62 g (60%) of 3-iodo-4,4-dimethyloxazolidin-2-one as off-white powder.

Preparation of 1-iodo-3,5,5-trimethylhydantoin in MeCN

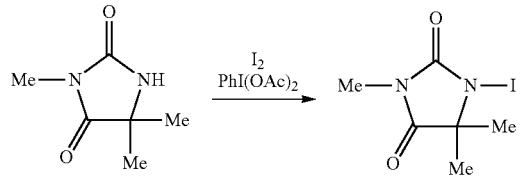 [SMILES: CN1C(=O)NC(C)(C)C1=O ; CN1C(=O)N(I)C(C)(C)C1=O]

A mixture of 3,5,5-trimethylhydantoin (10.0 g, 70.4 mmol), PhI(OAc)$_2$ (13.6 g, 42.2 mmol), I$_2$ (11.6 g, 45.7 mmol), and MeCN (100 mL) was stirred at rt in the dark for 6 h and then concentrated in vacuo. CCl$_4$ (100 mL) was added to the residue and the obtained mixture was stirred for 15 min at rt and 1 h at 0 to 5° C. The precipitated solid was filtered, washed on the filter with cold CCl$_4$ and dried in vacuo to give 17.9 g (95%) of crystalline 1-iodo-3,5,5-trimethylhydantoin. Mp 198-9° C. (dec); $^1$H NMR: δ 3.07 (s, 3H, CH$_3$), 1.24 (s, 6H, 2 CH$_3$) ppm; $^{13}$C NMR: δ 175.1, 156.1, 65.5, 26.4, 24.6 ppm; HRMS-ESI: (M+H)$^+$268.9773, C$_6$H$_{10}$N$_2$O$_2$I calc mass 268.9787.

Figure 3:
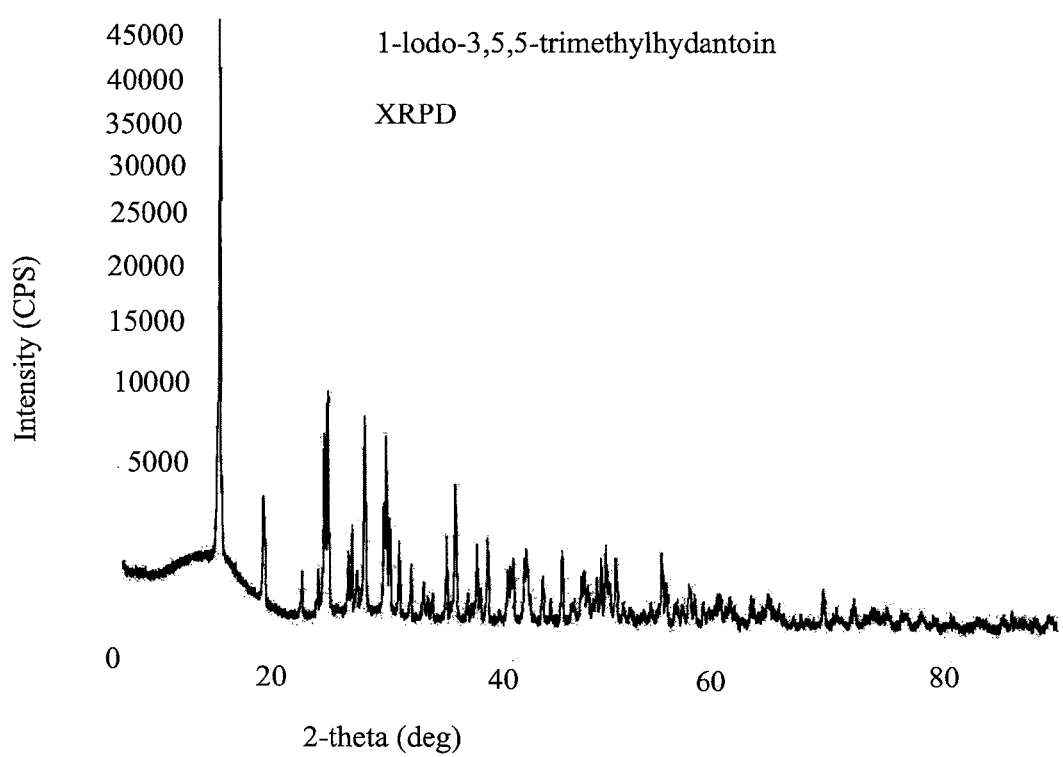
FIG. 3 depicts X-ray powder diffraction pattern (XRPD) of crystalline 1-iodo-3,5,5-trimethylhydantoin at 293(2) K.

FIG. 3 presents experimental x-ray powder diffraction pattern of the crystalline 1-iodo-3,5,5-trimethylhydantoin at 293(2) K. The crystalline 1-iodo-3,5,5-trimethylhydantoin exhibits an x-ray powder diffraction pattern having characteristic peaks, expressed in degrees 2θ at about 13.0±0.2, 17.0±0.2, 22.6±0.2, 22.9±0.2, 25.2±0.2, 26.4±0.2, 28.3±0.2, 29.5±0.2, and 34.7±0.2 at 293(2) K.

Figure 4:
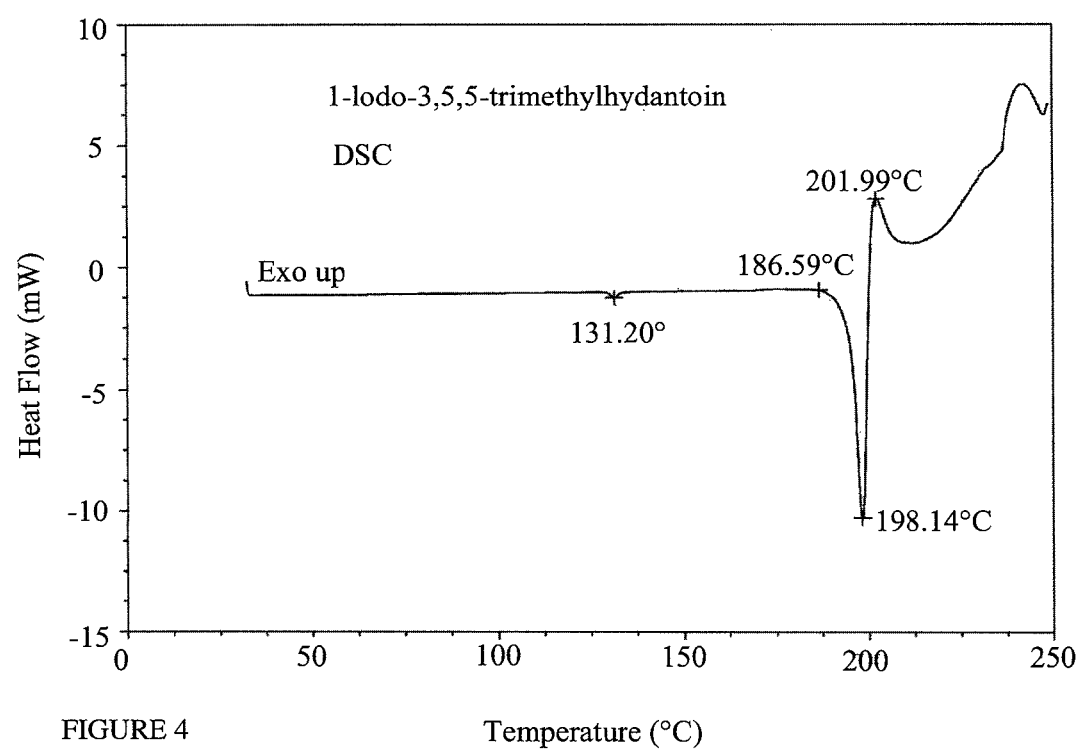
FIG. 4 depicts differential scanning calorimetry (DSC) curve of 1-iodo-3,5,5-trimethylhydantoin. Heat flow 5°/min.
Figure 8:
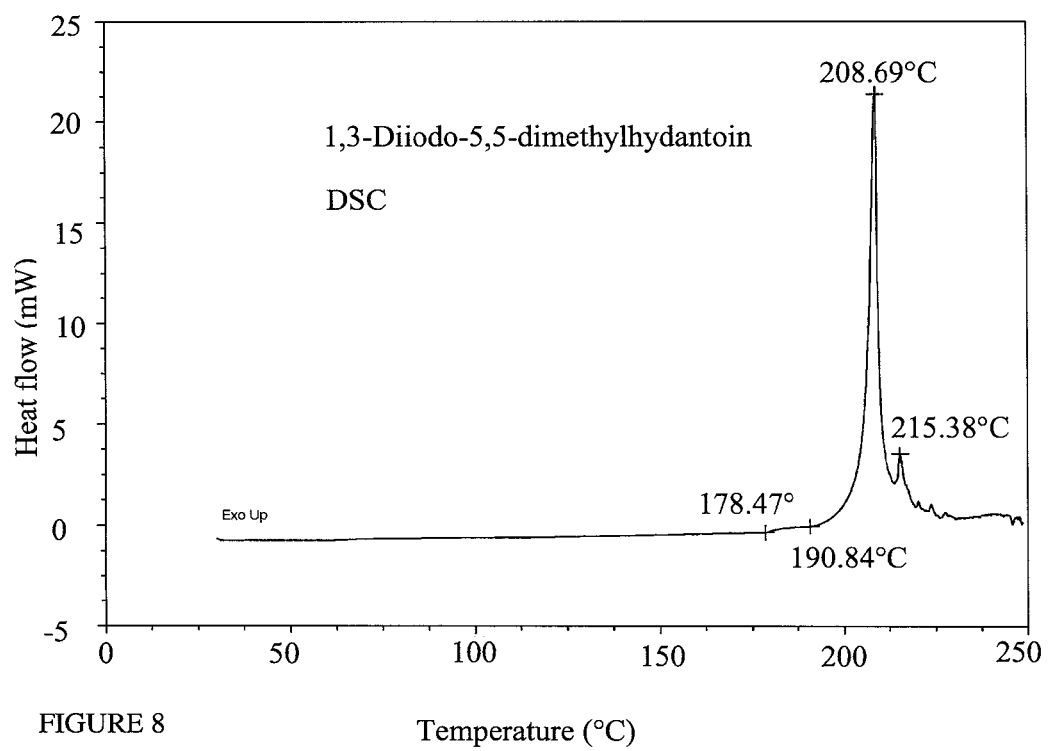
FIG. 8 depicts differential scanning calorimetry (DSC) curve of 1,3-diiodo-5,5-dimethylhydantoin. Heat flow 5°/min.

FIG. 4 presents differential scanning calorimetry (DSC) curve of the crystalline 1-iodo-3,5,5-trimethylhydantoin. For comparison see differential scanning calorimetry curve of 1,3-diiodo-5,5-trimethylhydantoin (FIG. 8).

Preparation of 1-iodo-3,5,5-trimethylhydantoin in CCl$_4$

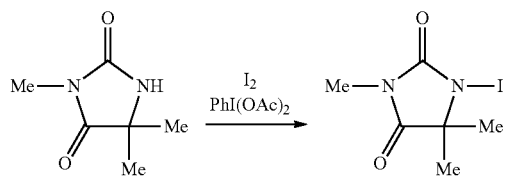 [SMILES: CN1C(=O)NC(C)(C)C1=O ; CN1C(=O)N(I)C(C)(C)C1=O]

A mixture of 3,5,5-trimethylhydantoin (1.00 g, 7.0 mmol), PhI(OAc)$_2$ (1.36 g, 4.2 mmol), I$_2$ (1.16 g, 4.57 mmol) and CCl$_4$ (12 mL) was stirred for 6 h at rt and 1 h at 0 to 5° C. The precipitated solid was filtered, washed on the filter with cold CCl$_4$ and dried in vacuo to give 1.43 g (70%) of crystalline 1-iodo-3,5,5-trimethylhydantoin.

Preparation of 1-iodo-3,5,5-trimethylhydantoin in Benzene

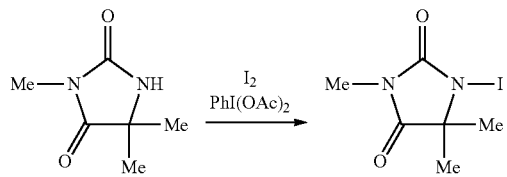 [SMILES: CN1C(=O)NC(C)(C)C1=O ; CN1C(=O)N(I)C(C)(C)C1=O]

A mixture of 3,5,5-trimethylhydantoin (1.0 g, 7 mmol), PhI(OAc)$_2$ (1.36 g, 4.22 mmol), I$_2$ (1.17 g, 4.57 mmol), and benzene (20 mL) was stirred at rt and 1 h at 0 to 5° C. The precipitated solid was filtered, washed on the filter with cold benzene and dried in vacuo to give 1.56 g (83%) of crystalline 1-iodo-3,5,5-trimethylhydantoin.

Preparation of 1-iodo-3,5,5-trimethylhydantoin in Toluene

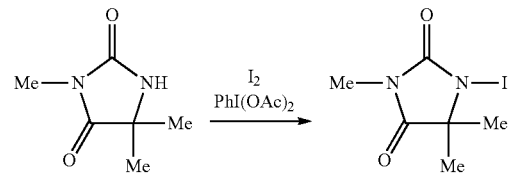 [SMILES: CN1C(=O)NC(C)(C)C1=O ; CN1C(=O)N(I)C(C)(C)C1=O]

A mixture of 3,5,5-trimethylhydantoin (1.0 g, 7 mmol), PhI(OAc)$_2$ (1.36 g, 4.22 mmol), I$_2$ (1.17 g, 4.57 mmol), and toluene (20 mL) was stirred at rt for 15 h and 1 h at 0 to 5° C. The precipitated solid was filtered, washed on the filter with cold toluene and dried in vacuo to give 1.21 g (65%) of crystalline 1-iodo-3,5,5-trimethylhydantoin.

Preparation of 1-iodo-3,5,5-trimethylhydantoin in Cyclohexane

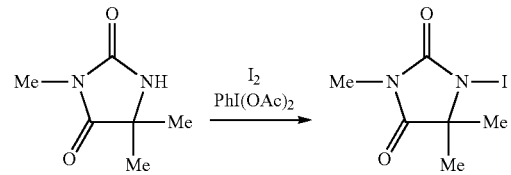 [SMILES: CN1C(=O)NC(C)(C)C1=O ; CN1C(=O)N(I)C(C)(C)C1=O]

A mixture of 3,5,5-trimethylhydantoin (1.0 g, 7 mmol), PhI(OAc)$_2$ (1.36 g, 4.22 mmol), I$_2$ (1.17 g, 4.57 mmol), and cyclohexane (20 mL) was stirred at rt for 40 h and 1 h at 0 to 5° C. The precipitated solid was filtered, washed on the filter with cold cyclohexane and dried in vacuo to give 1.64 g (88%) of crystalline 1-iodo-3,5,5-trimethylhydantoin.

Preparation of 1-iodo-3,5,5-trimethylhydantoin Using bis(trifluoroacetoxy)iodo]benzene

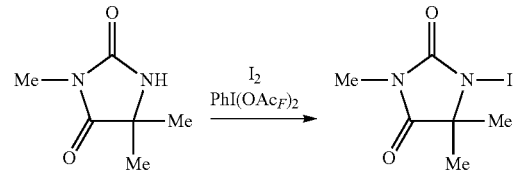 [SMILES: CN1C(=O)NC(C)(C)C1=O ; CN1C(=O)N(I)C(C)(C)C1=O]

A mixture of 3,5,5-trimethylhydantoin (prepared according to Example 1) (1.00 g, 7.0 mmol), [bis(trifluoroacetoxy)iodo]benzene (1.82 g, 4.2 mmol), I$_2$ (1.16 g, 4.6 mmol) and MeCN (10 mL) was stirred for 5 h at rt and concentrated in vacuo. CCl$_4$ (10 mL) was added to the residue and the obtained mixture was stirred for 15 min at rt and 1 h at 0 to 5° C. The precipitated solid was filtered, washed on the filter with cold CCl$_4$ and dried in vacuo to give 1.84 g (98%) of crystalline 1-iodo-3,5,5-trimethylhydantoin as off-white powder.

Preparation of 3-iodo-1,5,5-trimethylhydantoin

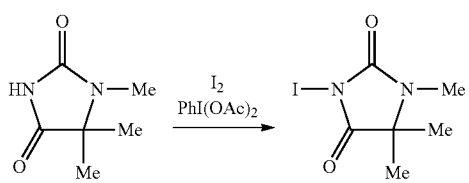 [SMILES: CN1C(=O)NC(=O)C1(C)C ; CN1C(=O)N(I)C(=O)C1(C)C]

A mixture of 1,5,5-trimethylhydantoin (commercial) (1.00 g, 7.0 mmol), PhI(OAc)$_2$ (1.4 g, 4.2 mmol), I$_2$ (1.2 g, 4.6 mmol) and MeCN (10 mL) was stirred at rt for 5 h and then concentrated in vacuo. The mixture was stirred for 5 h at rt and concentrated in vacuo. CCl$_4$ (10 mL) was added to the residue and the obtained mixture was stirred for 15 min at rt and 1 h at 0 to 5° C. The precipitated solid was filtered, washed on the filter with cold CCl$_4$ and dried in vacuo to give 1.84 g (98%) of crystalline 3-iodo-1,5,5-trimethylhydantoin. Mp 213-4° C. (dec); $^1$H NMR: δ 2.95 (s, 3H), 1.39 (s, 6H) ppm; $^{13}$C NMR: δ 178.6, 154.4, 64.2, 26.0, 22.9 ppm; HRMS-ESI: (M+H)$^+$268.9795, C$_6$H$_{10}$N$_2$O$_2$I calc mass 268.9787.

Figure 6:
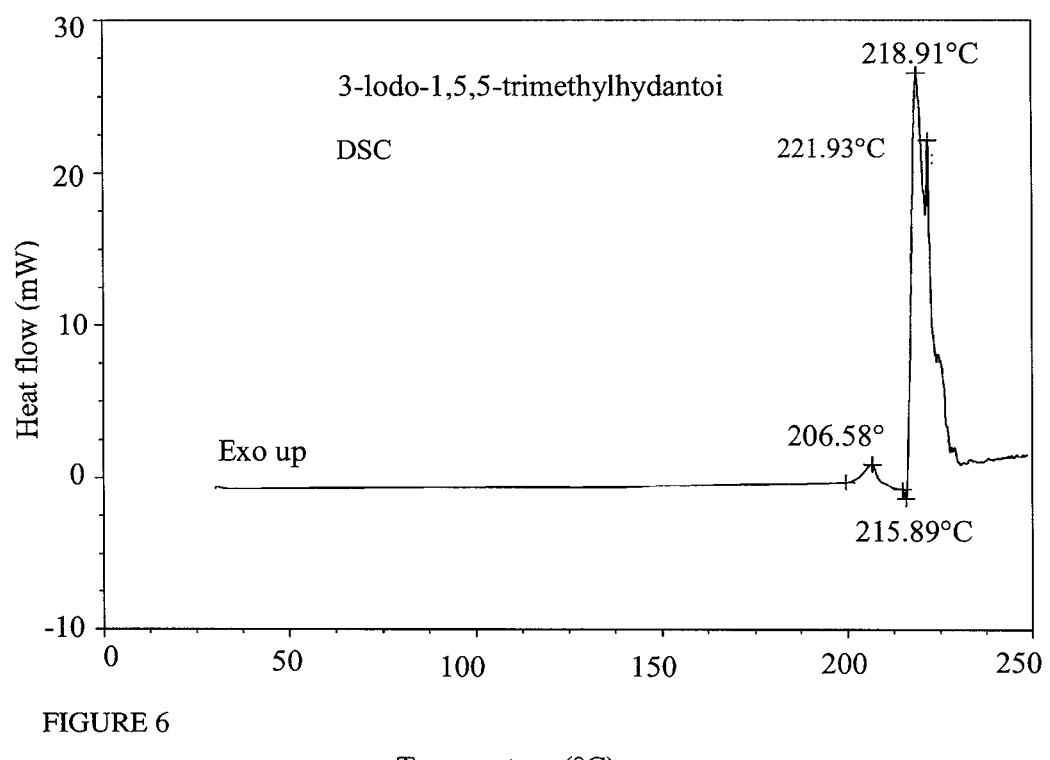
FIG. 6 depicts differential scanning calorimetry (DSC) curve of 3-iodo-1,5,5-trimethylhydantoin. Heat flow 5°/min.

FIG. 6 presents differential scanning calorimetry (DSC) curve of the crystalline 3-iodo-1,5,5-trimethylhydantoin.

Preparation of N-iodosaccharin in CCl$_4$

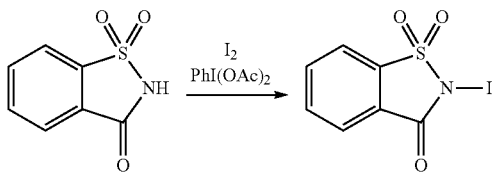 [SMILES: O=C1NS(=O)(=O)c2ccccc21 ; O=C1c2ccccc2S(=O)(=O)N1I]

A mixture of saccharin (1.00 g, 5.46 mmol), PhI(OAc)$_2$ (1.10 g, 3.28 mmol), I$_2$ (0.90 g, 3.55 mmol), and CCl$_4$ (20 mL) was stirred for 6 h at rt and for 1 h at 0 to 5° C. The precipitated solid was filtered, washed on the filter with cold CCl$_4$ and dried in vacuo to give 1.67 g (99%) of N-iodosaccharin as off-white powder. $^1$H NMR (CD$_3$CN) δ: 7.98 (t, J=7.9 Hz, 2H), 7.85 (m, 2H) ppm; $^{13}$C NMR (CD$_3$CN) δ: 162.6, 139.7, 135.8, 135.4, 128.5, 126.2, 122.3 ppm.

Preparation of N-Iodosaccharin in MeCN

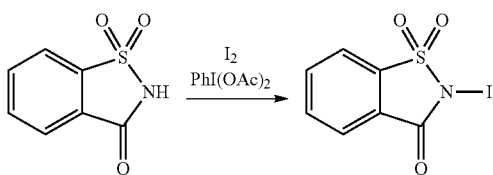 [SMILES: O=C1NS(=O)(=O)c2ccccc21 ; O=C1c2ccccc2S(=O)(=O)N1I]

A mixture of saccharin (0.40 g, 2.18 mmol), PhI(OAc)$_2$ (0.42 g, 1.31 mmol), I$_2$ (0.36 g, 1.42 mmol), and MeCN (10 mL) was stirred at rt for 6 h and then concentrated in vacuo. CCl$_4$ (10 mL) was added to the residue and the obtained mixture was stirred for 15 min at rt and 1 h at 0 to 5° C. The precipitated solid was filtered, washed on the filter with cold CCl$_4$ and dried in vacuo to give 0.67 g (99%) of N-iodosaccharin as off-white powder.

Preparation of N-Iodosaccharin in Benzene

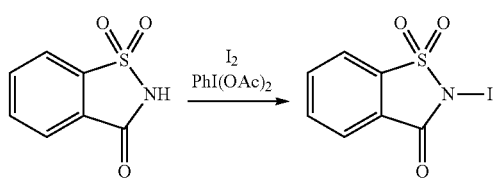 [SMILES: O=C1NS(=O)(=O)c2ccccc21 ; O=C1c2ccccc2S(=O)(=O)N1I]

A mixture of saccharin (1.00 g, 5.46 mmol), PhI(OAc)$_2$ (1.10 g, 3.28 mmol), I$_2$ (0.90 g, 3.55 mmol), and benzene (20 mL) was stirred for 60 h at rt and for 1 h at 0 to 5° C. The precipitated solid was filtered, washed on the filter with cold benzene and dried in vacuo to give 1.08 g (70%) of N-iodosaccharin as off-white powder.

Preparation of N-Iodosuccinimide in CCl$_4$

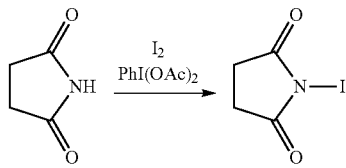 [SMILES: O=C1CCC(=O)N1 ; O=C1CCC(=O)N1I]

A mixture of succinimide (0.30 g, 3.0 mmol), PhI(OAc)$_2$ (0.59 g, 1.8 mmol), I$_2$ (0.5 g, 1.97 mmol) and CCl$_4$ (10 mL) was stirred for 3 h at rt and for 1 h at 0 to 5° C. The precipitated solid was filtered, washed on the filter with cold CCl$_4$ and dried in vacuo to give 0.64 g (93%) of N-iodosuccinimide. $^1$H NMR: δ 3.03 (s) ppm; $^{13}$C NMR: δ 177.6, 29.5 ppm. HRMS-ESI: (M+H)$^+$225.9326, C$_4$H$_5$NO$_2$I calc mass 225.9365.

Preparation of N-Iodosuccinimide in MeCN

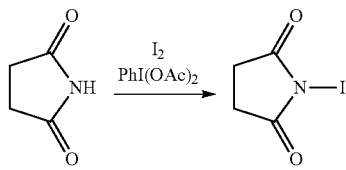 [SMILES: O=C1CCC(=O)N1 ; O=C1CCC(=O)N1I]

A mixture of succinimide (0.20 g, 2.0 mmol), PhI(OAc)$_2$ (0.39 g, 1.2 mmol), I$_2$ (0.33 g, 1.3 mmol) and MeCN (10 mL) was stirred at rt for 6 h and then concentrated in vacuo. CCl$_4$ (10 mL) was added to the residue and the obtained mixture was stirred for 15 min at rt and 1 h at 0 to 5° C. The precipitated solid was filtered, washed on the filter with cold CCl$_4$ and dried in vacuo to give 0.42 g (92%) of N-iodosuccinimide.

Preparation of N-Iodosuccinimide in Benzene

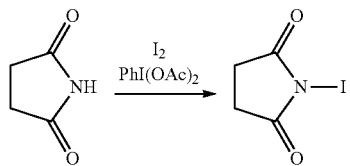

A mixture of succinimide (1.0 g, 10.1 mmol), PhI(OAc)$_2$ (1.95 g, 6.06 mmol), I$_2$ (1.67 g, 6.57 mmol) and benzene (20 mL) was stirred for 15 h at rt and for 1 h at 0 to 5° C. The precipitated solid was filtered, washed on the filter with cold benzene and dried in vacuo to give 2.2 g (99%) of N-iodosuccinimide.

Preparation of N-Iodosuccinimide in Cyclohexane

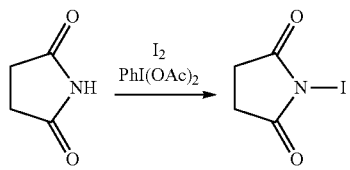 [SMILES: O=C1CCC(=O)N1 ; O=C1CCC(=O)N1I]

A mixture of succinimide (1.0 g, 10.1 mmol), PhI(OAc)$_2$ (1.95 g, 6.06 mmol), I$_2$ (1.67 g, 6.57 mmol) and cyclohexane (20 mL) was stirred for 15 h at rt and for 1 h at 0 to 5° C. The precipitated solid was filtered, washed on the filter with cold cyclohexane and dried in vacuo to give 2.2 g (99%) of N-iodosuccinimide.

Preparation of N-Iodophthalimide

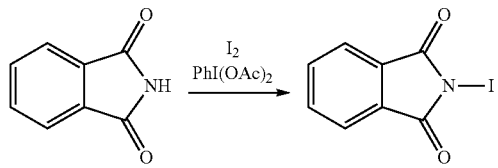 [SMILES: O=C1NC(=O)c2ccccc21 ; O=C1c2ccccc2C(=O)N1I]

A mixture of phthalimide (1.00 g, 6.8 mmol), PhI(OAc)$_2$ (1.31 g, 4.1 mmol), I$_2$ (1.12 g, 4.4 mmol), and MeCN (25 mL) was stirred for 6 h at rt and concentrated in vacuo. CCl$_4$ (25 mL) was added to the residue and the obtained mixture was stirred for 15 min at rt and 1 h at 0 to 5° C. The precipitated solid was filtered, washed on the filter with cold CCl$_4$ and dried in vacuo to give 1.80 g (97%) of N-iodophthalimide as off-white powder. $^1$H NMR (DMSO-d$_6$): δ 7.82-7.72 (m, 4H) ppm; $^{13}$C NMR (DMSO-d$_6$): δ 170.7, 133.8, 132.8, 122.8 ppm.

Preparation of N-Iodo-4-Nitrophthalimide

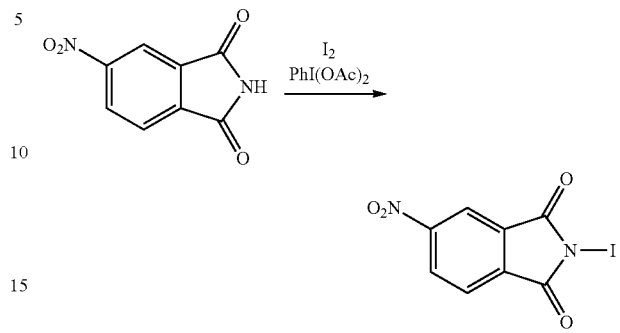

A mixture of 4-nitrophthalimide (0.40 g, 2.08 mmol), PhI(OAc)$_2$ (0.40 g, 1.25 mmol), I$_2$ (0.34 g, 1.35 mmol) and MeCN (10 mL) was stirred for 4 h at rt and concentrated in vacuo. CCl$_4$ (10 mL) was added to the residue and the obtained mixture was stirred for 15 min at rt and 1 h at 0 to 5° C. The precipitated solid was filtered off, washed on the filter with cold CCl$_4$ and dried in vacuo to give 0.63 g (100%) of N-iodo-4-nitrophthalimide. $^1$H NMR (CD$_3$CN): δ 8.51 (d, J=8.8 Hz, 1H), 8.47 (s, 1H) 7.97 (d, J=8.6 Hz, 1H) ppm; $^{13}$C NMR (CD$_3$CN): δ 169.3, 168.9, 152.3, 138.4, 135.1, 130.0, 125.3, 119.0 ppm. HRMS-APCI: (M+H$_2$O)$^+$ 335.92.40, C$_8$H$_3$N$_2$O$_4$I+H$_2$O calc mass 335.9243.

Example 5

Crystal of 3-iodo-4,4-dimethyloxazolidin-2-one of Formula IDMO

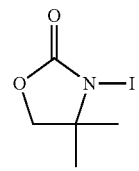

IDMO

3-Iodo-4,4-dimethyloxazolidin-2-one (0.2 g) was dissolved in acetone (2 mL). The solvents were slowly evaporated from the mixture at rt on the air to give 0.66×0.46×0.39 mm crystal of 3-iodo-4,4-dimethyloxazolidin-2-one. The crystalline 3-iodo-4,4-dimethyloxazolidin-2-one is characterized by a single x-ray crystallographic analysis at 200(1) K, which yields crystal parameters (Table 5.1), atomic positions of all atoms relative to the origin of the unit cell (Table 5.2), bond lengths (Table 5.3), and bond angles (Table 5.4) of 3-iodo-4,4-dimethyloxazolidin-2-one molecule.

TABLE 5.1

Crystal parameters of 3-iodo-4,4-dimethyloxazolidin-2-one

| | |
|---|---|
| Formula | C$_5$H$_8$INO$_2$ |
| Formula weight (amu) | 241.02 |
| Crystal system | Monoclinic |
| Space group | P 2$_1$/n |

TABLE 5.1-continued

Crystal parameters of 3-iodo-4,4-dimethyloxazolidin-2-one

| Cell dimensions | |
|---|---|
| a (Å) | 5.7963(3) |
| b (Å) | 10.9989(5) |
| c (Å) | 11.9849(6) |
| $\alpha = \gamma$ (°) | 90 |
| $\beta$ (°) | 98.580(2) |
| V (Å$^3$) | 755.52(6) |
| Z (molecules/units cell) | 4 |
| Density (g/cm$^3$) | 2.119 |

The unit cell dimension is defined by three parameters: length of the sides of the cell, relative angles of sides to each other and the volume of the cell. The lengths of the sides of the unit cell are defined by a, b and c. The relative angles of the cell sides are defined by $\alpha$, $\beta$ and $\gamma$. The volume of the cell is defined as V.

FIG. 1 depicts an ORTEP view of 3-iodo-4,4-dimethyl-oxazolidin-2-one molecule and the atomic numbering of non-hydrogen atoms as derived from single crystal x-ray analysis of the crystalline 3-iodo-4,4-dimethyloxazolidin-2-one.

TABLE 5.2

Atomic coordinates (×10$^4$) and equivalent isotropic displacement parameters (Å$^2$ × 10$^3$) for crystalline 3-iodo-4,4-dimethyloxazolidin-2-one. U(eq) is defined as one third of the trace of the orthogonalizedUij tensor.

| | X | Y | Z | U(eq) |
|---|---|---|---|---|
| I(1) | 2689(1) | 4155(1) | 11713(1) | 23(1) |
| O(1) | 1818(3) | 1294(1) | 12274(1) | 31(1) |
| O(2) | 2496(3) | 561(1) | 10603(1) | 26(1) |
| N(1) | 2446(3) | 2564(1) | 10816(1) | 22(1) |
| C(1) | 6092(4) | 2502(2) | 9971(2) | 32(1) |
| C(2) | 3440(3) | 2402(2) | 9752(2) | 22(1) |
| C(3) | 2220(3) | 1485(2) | 11317(2) | 22(1) |
| C(4) | 2626(4) | 1094(2) | 9503(2) | 26(1) |
| C(5) | 2361(4) | 3274(2) | 8843(2) | 32(1) |

TABLE 5.3

Bond lengths (Å) for 3-iodo-4,4-dimethyloxazolidin-2-one molecule

| I(1)—N(1) | 2.0472(15) | O(1)—C(3) | 1.222(2) |
|---|---|---|---|
| O(2)—C(3) | 1.353(2) | O(2)—C(4) | 1.455(2) |
| N(1)—C(3) | 1.346(2) | N(1)—C(2) | 1.487(2) |
| C(1)—C(2) | 1.524(3) | C(2)—C(5) | 1.514(3) |
| C(2)—C(4) | 1.530(3) | | |

TABLE 5.4

Angles (°) for 3-iodo-4,4-dimethyloxazolidin-2-one molecule

| C(3)—O(2)—C(4) | 107.35(15) | C(3)—N(1)—C(2) | 110.66(15) |
|---|---|---|---|
| C(3)—N(1)—I(1) | 121.56(13) | C(2)—N(1)—I(1) | 123.23(12) |
| N(1)—C(2)—C(5) | 111.68(16) | N(1)—C(2)—C(1) | 110.71(16) |
| C(5)—C(2)—C(1) | 112.08(17) | N(1)—C(2)—C(4) | 97.60(14) |
| C(5)—C(2)—C(4) | 111.89(17) | C(1)—C(2)—C(4) | 112.07(17) |
| O(1)—C(3)—N(1) | 127.97(18) | O(1)—C(3)—O(2) | 121.45(17) |
| N(1)—C(3)—O(2) | 110.58(16) | O(2)—C(4)—C(2) | 104.95(15) |

Example 6

Crystal of 3-iodo-1,5,5-trimethylhydantoin of Formula (3-ITMH)

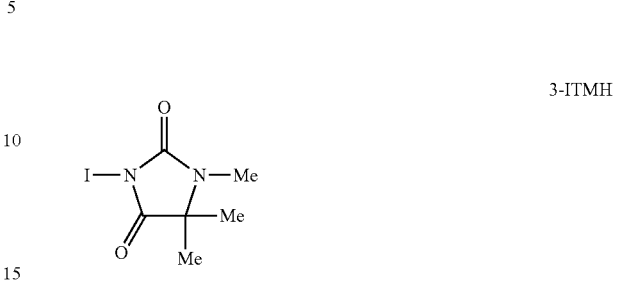

3-ITMH

3-Iodo-1,5,5-trimethylhydantoin (0.2 g) was dissolved in acetone (2 mL). The solvents were slowly evaporated from the mixture at rt to give 0.63×0.37×0.22 mm crystal of 3-iodo-1,5,5-trimethylhydantoin. The crystalline 3-iodo-1,5,5-trimethylhydantoin is characterized by a single x-ray crystallographic analysis at 293(2) K, which yields crystal parameters (Table 6.1), atomic positions of all atoms relative to the origin of the unit cell (Table 6.2), bond lengths (Table 6.3), and bond angles (Table 6.4) of 3-iodo-1,5,5-trimethylhydantoin molecule.

TABLE 6.1

Crystal parameters of 3-iodo-1,5,5-trimethylhydantoin

| Formula | $C_6H_9IN_2O_2$ |
|---|---|
| Formula weight (amu) | 268.05 |
| Crystal system | Orthohombic |
| Space group | Pnma |
| Cell dimensions | |
| a (Å) | 11.217(3) |
| b (Å) | 7.423(2) |
| c (Å) | 10.454(2) |
| $\alpha = \beta = \gamma$ (°) | 90 |
| V (Å$^3$) | 870.4(4) |
| Z (molecules/units cell) | 4 |
| Density (g/cm$^3$) | 2.045 |

The unit cell dimension is defined by three parameters: length of the sides of the cell, relative angles of sides to each other and the volume of the cell. The lengths of the sides of the unit cell are defined by a, b and c. The relative angles of the cell sides are defined by $\alpha$, $\beta$ and $\gamma$. The volume of the cell is defined as V.

Figure 5:
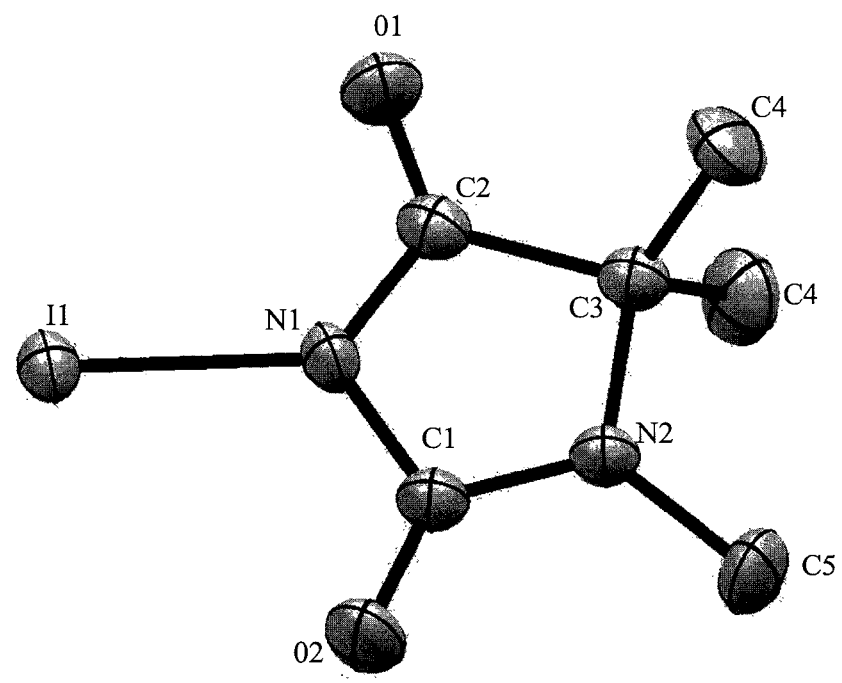
FIG. 5 depicts an Oak Ridge Thermal-Ellipsoid Plot Program (ORTEP) view of 3-iodo-1,5,5-trimethylhydantoin molecule and the atomic numbering of non-hydrogen atoms as derived from single crystal x-ray analysis of the crystalline 3-iodo-1,5,5-trimethylhydantoin.

FIG. 5 presents an ORTEP view of 3-iodo-1,5,5-trimethylhydantoin molecule and the atomic numbering of non-hydrogen atoms as derived from single crystal x-ray analysis of the crystalline 3-iodo-1,5,5-trimethylhydantoin.

TABLE 6.2

Atomic coordinates (×10$^4$) and equivalent isotropic displacement parameters (Å$^2$ × 10$^3$) for the crystalline 3-iodo-1,5,5-trimethylhydantoin. U(eq) is defined as one third of the trace of the orthogonalized Uij tensor.

| | X | Y | Z | U(eq) |
|---|---|---|---|---|
| I(1) | 5567(1) | 2500 | −1784(1) | 30(1) |
| N(1) | 4170(5) | 2500 | −501(5) | 30(1) |
| N(2) | 3335(5) | 2500 | 1381(5) | 29(1) |
| O(1) | 2592(5) | 2500 | −1857(4) | 42(1) |
| O(2) | 5378(4) | 2500 | 1326(6) | 45(1) |
| C(1) | 4378(5) | 2500 | 833(7) | 29(1) |
| C(2) | 3027(5) | 2500 | −783(6) | 29(1) |

TABLE 6.2-continued

Atomic coordinates (×10^4) and equivalent isotropic displacement parameters (Å^2 × 10^3) for the crystalline 3-iodo-1,5,5-trimethylhydantoin. U(eq) is defined as one third of the trace of the orthogonalized Uij tensor.

|      | X       | Y    | Z       | U(eq) |
|------|---------|------|---------|-------|
| C(3) | 2325(5) | 2500 | 471(5)  | 29(1) |
| C(4) | 1558(4) | 797(8) | 594(5) | 46(1) |
| C(5) | 3193(6) | 2500 | 2774(7) | 46(2) |

TABLE 6.3

Bond lengths (Å) for 3-iodo-1,5,5-trimethylhydantoin molecule

| I(1)—N(1)    | 2.063(5) |
| N(1)—C(2)    | 1.315(8) |
| N(1)—C(1)    | 1.414(9) |
| N(2)—C(1)    | 1.303(8) |
| N(2)—C(5)    | 1.466(7) |
| N(2)—C(3)    | 1.478(7) |
| O(1)—C(2)    | 1.224(7) |
| O(2)—C(1)    | 1.234(7) |
| C(2)—C(3)    | 1.530(8) |
| C(3)—C(4)    | 1.535(6) |
| C(3)—C(4)#1  | 1.535(6) |

TABLE 6.4

Angles (°) for 3-iodo-1,5,5-trimethylhydantoin molecule

| C(2)—N(1)—C(1)     | 112.5(5) |
| C(2)—N(1)—I(1)     | 126.5(4) |
| C(1)—N(1)—I(1)     | 121.1(4) |
| C(1)—N(2)—C(5)     | 122.3(5) |
| C(1)—N(2)—C(3)     | 113.9(5) |
| C(5)—N(2)—C(3)     | 123.8(5) |
| O(2)—C(1)—N(2)     | 129.2(7) |
| O(2)—C(1)—N(1)     | 124.2(6) |
| N(2)—C(1)—N(1)     | 106.6(5) |
| O(1)—C(2)—N(1)     | 126.5(6) |
| O(1)—C(2)—C(3)     | 125.5(6) |
| N(1)—C(2)—C(3)     | 108.0(5) |
| N(2)—C(3)—C(2)     | 99.0(4)  |
| N(2)—C(3)—C(4)     | 112.1(3) |
| C(2)—C(3)—C(4)     | 111.1(3) |
| N(2)—C(3)—C(4)#1   | 112.1(3) |
| C(2)—C(3)—C(4)#1   | 111.1(3) |
| C(4)—C(3)—C(4)#1   | 110.9(5) |

Example 7

Iododecarboxylation of Alkanoic Acids

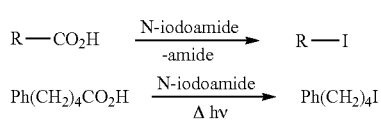

Solvent Effect

A mixture of Ph(CH$_2$)$_4$CO$_2$H (0.25 mmol), N-iodoamide (0.25 mmol), and solvent (1 mL) was refluxed (Δ) under irradiation with 250 W tungsten lamp (hv) for 1 h. Conversion degree was determined by $^1$H NMR spectra of the reaction mixture. The solvent effect is presented in Table 7.1:

TABLE 7.1

Solvent effect of iododecarboxylation of organic carboxylic acids.

| entry | reaction conditions | conversion, % |
|-------|---------------------|---------------|
| 1     | IDMO/DCE            | 82            |
| 2     | IDMO/CCl$_4$        | 61            |
| 3     | IDMO/CHCl$_3$       | 79            |
| 4     | IDMO/DCM            | 88            |
| 5     | IDMO/PhH            | 85            |
| 6     | IDMO/PhCF$_3$       | 82            |
| 7     | IDMO/C$_6$H$_{12}$  | 76            |
| 8     | IDMO/MeOAc          | 65            |
| 9     | IDMO/EtOAc          | 80            |
| 10    | IDMO/MeCN           | 69            |
| 11    | 1-ITMH/DCE          | 88            |
| 12    | 1-ITMH/CCl$_4$      | 85            |
| 13    | 1-ITMH/CHCl$_3$     | 82            |
| 14    | 1-ITMH/DCM          | 78            |
| 15    | 1-ITMH/PhH          | 70            |
| 16    | 1-ITMH/PhCF$_3$     | 79            |
| 17    | 1-ITMH/C$_6$H$_{12}$| 70            |
| 18    | 1-ITMH/MeOAc        | 58            |
| 19    | 1-ITMH/EtOAc        | 72            |
| 20    | 1-ITMH/MeCN         | 71            |
| 21    | NIS/DCE             | 38            |
| 22    | NIS/C$_6$H$_{12}$   | 1             |
| 23    | NIS/EtOAc           | 18            |
| 24    | NIS/MeCN            | 44            |
| 25    | DIH/DCE             | 83            |
| 26    | DIH/CCl$_4$         | 40            |
| 27    | DIH/CHCl$_3$        | 20            |
| 28    | DIH/DCM             | 14            |
| 29    | DIH/PhH             | 22            |
| 30    | DIH/C$_6$H$_{12}$   | 45            |
| 31    | DIH/EtOAc           | 62            |
| 32    | DIH/MeCN            | 59            |
| 33    | 3-ITMH/DCE          | 45            |
| 34    | 3-ITMH/CCl$_4$      | 22            |
| 35    | 3-ITMH/CHCl$_3$     | 42            |
| 36    | 3-ITMH/DCM          | 25            |
| 37    | 3-ITMH/PhH          | 51            |
| 37    | 3-ITMH/EtOAc        | 40            |
| 38    | 3-ITMH/C$_6$H$_{12}$| 36            |
| 39    | 3-ITMH/MeCN         | 44            |

Solvent and Radiation Effects

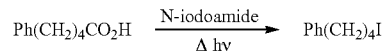

A mixture of Ph(CH$_2$)$_4$CO$_2$H (1 mmol), N-iodoamide, and solvent (4 mL) was refluxed (Δ) or under irradiation with 250 W tungsten lamp (TL) or under fluorescent room lighting (FL). Conversion degree was determined by $^1$H NMR spectra of the reaction mixture. The N-iodoamide, solvent and radiation effects are presented in Table 7.2.

TABLE 7.2

Solvent and radiation effect of iododecarboxylation of organic carboxylic acids

| | | conversion, % | | | |
|---|---|---|---|---|---|
| entry | reaction conditions | 1 h | 2 h | 4 h | 8 h |
| 1 | NIS 1 mmol/DCE, TL    | 38 | 42 | 61 | 63  |
| 2 | NIS 1.5 mmol/DCE, TL  | 62 | 75 | 91 | 100 |
| 3 | DIH 0.75 mmol/PhCl, FL| 70 | 73 | 73 | 73  |
| 4 | DIH 0.75 mmol/PhCl, TL| 74 | 81 | 92 | 95  |
| 5 | DIH 0.5 mmol/DCE, TL  | 11 | 22 | 48 | 60  |
| 6 | DIH 1 mmol/DCE, FL    | 4  | 8  | 16 | 32  |
| 7 | DIH 1 mmol/DCE, TL    | 47 | 67 | 98 | 100 |

TABLE 7.2-continued

Solvent and radiation effect of iododecarboxylation of organic carboxylic acids

| entry | reaction conditions | conversion, % | | | |
|---|---|---|---|---|---|
| | | 1 h | 2 h | 4 h | 8 h |
| 8 | 3-ITMH 1 mmol/DCE, TL | 41 | 43 | 44 | 46 |
| 9 | 3-ITMH 1.5 mmol/DCE, TL | 67 | 68 | 69 | 71 |
| 10 | 1-ITMH 1.5 mmol/PhCl, FL | 98 | 100 | | |
| 11 | 1-ITMH 1 mmol/DCE, TL | 88 | 88 | 88 | 88 |
| 12 | 1-ITMH 1.5 mmol/DCE, FL | 68 | 75 | 83 | 89 |
| 13 | 1-ITMH 1.5 mmol/DCE, TL | 100 | | | |
| 14 | 1-ITMH 1.5 mmol/CCl$_4$, FL | 55 | 73 | 83 | 88 |
| 15 | 1-ITMH 1.5 mmol/CCl$_4$, TL | 100 | | | |
| 16 | 1-ITMH 1.5 mmol/C$_6$H$_{12}$, TL | 61 | 95 | 100 | |
| 17 | IDMO 1.5 mmol/PhCl, FL | 96 | 100 | | |
| 18 | IDMO 1 mmol/DCE, TL | 82 | 82 | 82 | 82 |
| 19 | IDMO 1.5 mmol/DCE, FL | 78 | 84 | 89 | 93 |
| 20 | IDMO 1.5 mmol/DCE, TL | 100 | | | |
| 21 | IDMO 1.5 mmol/CCl$_4$, TL | 100 | | | |
| 22 | IDMO 1.5 mmol/C$_6$H$_{12}$, TL | 27 | 70 | 85 | 85 |
| 23 | IPT 1 mmol/DCE, FL | 60 | 70 | 71 | 71 |

Solvent and Radiation Effects

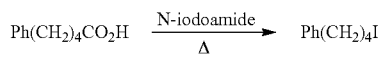

A mixture of 5-phenylvaleric acid (1 mmol), N-iodoamide, and solvent (5 mL) was refluxed (Δ) in the dark (NL), or under irradiation with 250 W tungsten lamp (TL) or under fluorescent room lighting (FL). The reaction mixture was concentrated in vacuo. The residue was dissolved in hexane (5 mL), washed with 1 M aq Na$_2$SO$_3$ (2×5 mL), dried over Na$_2$SO$_4$, filtered through short neutral alumina pad and concentrated in vacuo to obtain (4-iodobutyl)benzene.

The N-iodoamide, solvent and radiation effects are presented in Table 7.3.

TABLE 7.3

Solvent and radiation effect of iododecarboxylation of organic carboxylic acids

| entry | reaction conditions | yield % |
|---|---|---|
| 1 | NIS 1.5 mmol/DCE, NL 15 h | 32 |
| 2 | DIH 1.5 mmol/DCE, NL 15 h | 43 |
| 3 | IDMO 1.5 mmol/DCE, NL 15 h | 65 |
| 4 | IDMO 1.5 mmol/DCE, FL 24 h | 82 |
| 5 | IDMO 1.25 mmol/DCM, TL 3 h | 92 |
| 6 | IDMO 1.5 mmol/CCl$_4$, TL 24 h | 85 |
| 7 | IDMO 1.5 mmol/c-C$_6$H$_{12}$, TL 24 h | 75 |
| 8 | 1-ITMH 1.5 mmol/DCE, NL 15 h | 62 |
| 9 | 1-ITMH 1.5 mmol/DCE, FL 24 h | 85 |
| 10 | 1-ITMH 1.25 mmol/CHCl$_3$, TL 3 h | 90 |
| 11 | 1-ITMH 1.25 mmol/DCM, TL 3 h | 90 |
| 12 | 1-ITMH 1.5 mmol/CCl$_4$, FL 24 h | 90 |
| 13 | 1-ITMH 1.5 mmol/CCl$_4$, TL 24 h | 90 |
| 14 | 1-ITMH 1.25 mmol/c-C$_6$H$_{12}$, TL 3 h | 86 |
| 15 | 1-ITMH 1.5 mmol/c-C$_6$H$_{12}$, TL 24 h | 88 |
| 16 | 1-ITMH 1.5 mmol/EtOAc, TL 3 h | 91 |

Example 8

Iododecarboxylation with 3-iodo-4,4-dimethyloxazolidin-2-one (IDMO) and Recovery of 4,4-dimethyloxazolidin-2-one (DMO)

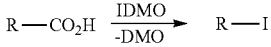

Preparation of (4-iodobutyl)benzene with IDMO in DCM and Recovery of DMO

A mixture of 5-phenylvaleric acid (0.50 g, 2.8 mmol), 3-iodo-4,4-dimethyloxazolidin-2-one (0.85 g, 3.5 mmol), and DCM (10 mL) was refluxed under irradiation with tungsten lamp for 3 h and concentrated in vacuo. The residue was treated with hexane (10 mL) and 1 M aq Na$_2$SO$_3$ (5 mL), extracted with hexane (2×10 mL) and then with DCM (3×20 mL). The combine DCM extracts were dried over Na$_2$SO$_4$, filtered and concentrated in vacuo to give 0.35 g, (87%) of 4,4-dimethyl-2-oxazolidinone. The combined hexane extracts were washed with 1 M aq Na$_2$SO$_3$ (5 mL), dried over Na$_2$SO$_4$, filtered through short alumina pad and concentrated in vacuo to give 0.67 g (92%) of (4-iodobutyl)benzene. $^1$H NMR: δ 7.31 (m, 2H), 7.21 (m, 3H), 3.22 (t, J=6.9 Hz, 2H, CH$_2$I), 2.66 (t, J=7.5 Hz, 2H), 1.87 (m, 2H), 1.77 (m, 2H); $^{13}$C NMR: δ 141.9, 128.5, 126.0, 34.9, 33.0, 32.3, 6.9 (C—I).

Preparation of 3-Chloroiodobenzene with IDMO and Recovery of DMO

A mixture of 3-chlorobenzoic acid (0.31 g, 2.0 mmol), 3-iodo-4,4-dimethyloxazolidin-2-one (0.72 g, 3.0 mmol), and CCl$_4$ (10 mL) was refluxed under irradiation with tungsten lamp for 24 h. The cold reaction mixture was washed with 1 M aq Na$_2$SO$_3$ (2×5 mL), dried over Na$_2$SO$_4$, filtered through short neutral alumina pad and concentrated in vacuo to give 0.24 g (50%) of 3-chloroiodobenzene. The combine aq sodium sulfite washings were extracted with DCM (3×10 mL), carefully acidified with conc. hydrochloric acid to pH 2 and stirred at 0-5° C. for 2 h. The precipitated solid was filtered off, washed on the filter with cold water and dried in vacuo to recover 0.13 g (42%) of 3-chlorobenzoic acid. The combine DCM extracts were dried over Na$_2$SO$_4$, filtered and concentrated in vacuo to obtain 0.24 g (69%) of 4,4-dimethyloxazolidin-2-one.

Preparation of (4-Iodobutyl)Benzene with IDMO in Cyclohexane

A mixture of 5-phenylvaleric acid (0.18 g, 1.0 mmol), 3-iodo-4,4-dimethyloxazolidin-2-one (0.36 g, 1.5 mmol), and cyclohexane (4 mL) was refluxed under irradiation with tungsten lamp for 24 h. The cold reaction mixture was washed with 1 M aq $Na_2SO_3$ (2×5 mL), dried over $Na_2SO_4$, filtered through short alumina pad and concentrated in vacuo to give 0.20 g (75%) of (4-iodobutyl)benzene.

Preparation of (4-iodobutyl)benzene with IDMO in Benzene

A mixture of 5-phenylvaleric acid (0.18 g, 1.0 mmol), 3-iodo-4,4-dimethyloxazolidin-2-one (0.36 g, 1.5 mmol), and PhH (4 mL) was refluxed under irradiation with tungsten lamp for 4 h. The cold reaction mixture was washed with 1 M aq $Na_2SO_3$ (2×5 mL), dried over $Na_2SO_4$, filtered through short alumina pad and concentrated in vacuo to give 0.22 g (85%) of (4-iodobutyl)benzene.

Preparation of (4-iodobutyl)benzene with IDMO in $CCl_4$

A mixture of 5-phenylvaleric acid (0.18 g, 1.0 mmol), 3-iodo-4,4-dimethyloxazolidin-2-one (0.36 g, 1.5 mmol), and $CCl_4$ (4 mL) was refluxed under irradiation with tungsten lamp for 4 h. The cold reaction mixture was washed with 1 M aq $Na_2SO_3$ (2×5 mL), dried over $Na_2SO_4$, filtered through short alumina pad and concentrated in vacuo to give 0.22 g (85%) of (4-iodobutyl)benzene.

Preparation of 1-(2-iodoethyl)-4-methoxybenzene with IDMO

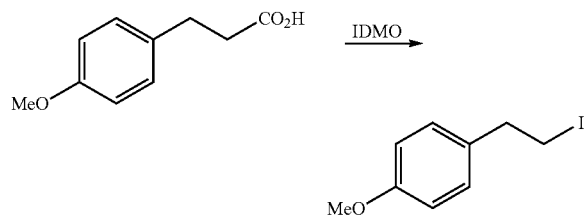

A mixture of 3-(4-methoxyphenyl)propanoic acid (0.18 g, 1.00 mmol), 3-iodo-4,4-dimethyloxazolidin-2-one (0.30 g, 1.25 mmol), and DCM (5 mL) was refluxed under irradiation with tungsten lamp for 1 h and concentrated in vacuo. The residue was treated with 1 M aq $Na_2SO_3$ (5 mL) and extracted with hexane (2×5 mL). The combined organic extracts were washed with 1 M aq $Na_2SO_3$ (5 mL), dried over $Na_2SO_4$, filtered through short neutral alumina pad and concentrated in vacuo to give 0.18 g (70%) of 1-(2-iodo-ethyl)-4-methoxybenzene. $^1$H NMR: δ 7.12 (d, J=8.4 Hz, 2H), 6.86 (d, J=8.4 Hz, 2H), 3.80 (s, 3H), 3.32 (t, J=7.8 Hz, 2H), 3.12 (t, J=7.8 Hz, 2H) ppm; $^{13}$C NMR: δ 158.7, 132.9, 129.4, 114.1, 55.3, 39.6, 6.5 ppm.

Example 9

Iododecarboxylation with 1-iodo-3,5,5-trimethylhydantoin (1-ITMH) and Recovery of 3,5,5-trimethylhydantoin (3,5,5-TMH)

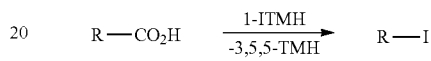

Preparation of (4-iodobutyl)benzene with 1-ITMH in DCM and Recovery of 3,5,5-TMH

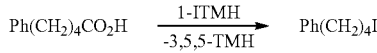

A mixture of 5-phenylvaleric acid (0.30 g, 1.7 mmol), 1-iodo-3,5,5-trimethylhydantoin (0.57 g, 2.1 mmol), and DCM (10 mL) was refluxed under irradiation with tungsten lamp for 3 h and then concentrated in vacuo. The residue was treated with hexane (5 mL) and 1 M aq $Na_2SO_3$ (5 mL), extracted with hexane (2×5 mL) and then with DCM (3×10 mL). The combined DCM extracts were dried over $Na_2SO_4$, filtered and concentrated in vacuo to give 0.27 g (90%) of 3,5,5-trimethylhydantoin. The combined hexane extracts were washed with 1 M aq $Na_2SO_3$ (5 mL), dried over $Na_2SO_4$, filtered through short neutral alumina pad and concentrated in vacuo to give 0.39 g (90%) of (4-iodobutyl)benzene.

Preparation of (4-iodobutyl)benzene with 1-ITMH in Cyclohexane and Recovery of 3,5,5-TMH

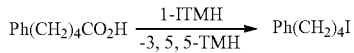

A mixture of 5-phenylvaleric acid (0.30 g, 1.7 mmol), 1-iodo-3,5,5-trimethylhydantoin (0.57 g, 2.1 mmol), and cyclohexane (10 mL) was refluxed under irradiation with tungsten lamp for 3 h. The cold reaction mixture was treated with 1 M aq $Na_2SO_3$ (5 mL), extracted with cyclohexane (2×10 mL) and then with DCM (3×10 mL). The combine DCM extracts were dried over $Na_2SO_4$, filtered and concentrated in vacuo to give 0.26 g, (86%) of 3,5,5-trimethylhydantoin. The combine cyclohexane extracts were washed with 1 M aq $Na_2SO_3$ (10 mL), dried over $Na_2SO_4$, filtered through short neutral alumina pad and concentrated in vacuo to give 0.40 g (92%) of (4-iodobutyl)benzene.

Preparation of 3-bromoiodobenzene with 1-ITMH in CCl₄ and Recovery of 3,5,5-TMH

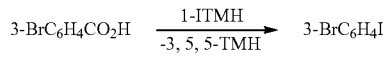

A mixture of 3-bromobenzoic acid (0.40 g, 2.0 mmol), 1-iodo-3,5,5-trimethylhydantoin (0.80 g, 3.0 mmol), and CCl₄ (10 mL) was refluxed under irradiation with tungsten lamp for 15 h. The cold reaction mixture was washed with 1 M aq Na₂SO₃ (2×5 mL), dried over Na₂SO₄, filtered through short neutral alumina pad and concentrated in vacuo to give 0.35 g (61%) of 3-bromoiodobenzene. The combine aq sodium sulfite washings were extracted with DCM (3×10 mL), carefully acidified with conc. hydrochloric acid to pH 2 and stirred at 0-5° C. for 2 h. The precipitated solid was filtered off, washed on the filter with cold water and dried in vacuo to recover 0.12 g (30%) of 3-bromobenzoic acid. The combine DCM extracts were dried over Na₂SO₄, filtered and concentrated in vacuo to obtain 0.21 g (75%) of 3,5,5-trimethylhydantoin.

Preparation of (4-iodobutyl)benzene with 1-ITMH in Benzene

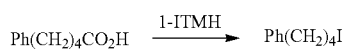

A mixture of 5-phenylvaleric acid (0.18 g, 1.0 mmol), 1-iodo-3,5,5-trimethylhydantoin 1-ITMH (0.40 g, 1.5 mmol), and PhH (5 mL) was refluxed under irradiation with tungsten lamp for 4 h. The cold reaction mixture was washed with 1 M aq Na₂SO₃ (2×5 mL), dried over Na₂SO₄, filtered through short alumina pad and concentrated in vacuo to give 0.24 g (90%) of (4-iodobutyl)benzene.

Preparation of (4-iodobutyl)benzene with 1-ITMH in CCl₄

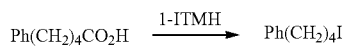

A mixture of 5-phenylvaleric acid (0.18 g, 1.0 mmol), 1-iodo-3,5,5-trimethylhydantoin (0.40 g, 1.5 mmol), and CCl₄ (5 mL) was refluxed under fluorescent room lighting for 24 h. The cold reaction mixture was washed with 1 M aq Na₂SO₃ (2×5 mL), dried over Na₂SO₄, filtered through short alumina pad and concentrated in vacuo to give 0.24 g (90%) of (4-iodobutyl)benzene.

Preparation of (4-iodobutyl)benzene with 1-ITMH in EtOAc

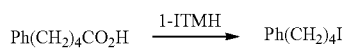

A mixture of 5-phenylvaleric acid (0.09 g, 0.5 mmol), 1-iodo-3,5,5-trimethylhydantoin (0.2 g, 0.75 mmol), and EtOAc (2 mL) was refluxed under irradiation with tungsten lamp for 3 h and then concentrated in vacuo. The residue was treated with hexane (5 mL) and 1 M aq Na₂SO₃ (5 mL), extracted with hexane (2×5 mL). The combined hexane extracts were washed with 1 M aq Na₂SO₃ (5 mL), dried over Na₂SO₄, filtered through short neutral alumina pad and concentrated in vacuo to give 0.12 g (90%) of (4-iodobutyl)benzene.

Preparation of (4-iodobutyl)benzene with 1-ITMH in CHCl₃

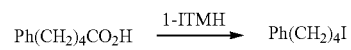

A mixture of 5-phenylvaleric acid (0.09 g, 0.5 mmol), 1-iodo-3,5,5-trimethylhydantoin (0.2 g, 0.75 mmol), and CHCl₃ (2 mL) was refluxed under irradiation with tungsten lamp for 3 h and then concentrated in vacuo. The residue was treated with hexane (5 mL) and 1 M aq Na₂SO₃ (5 mL), extracted with hexane (2×5 mL). The combined hexane extracts were washed with 1 M aq Na₂SO₃ (5 mL), dried over Na₂SO₄, filtered through short neutral alumina pad and concentrated in vacuo to give 0.13 g (90%) of (4-iodobutyl)benzene.

Preparation of (4-iodobutyl)benzene with 1-ITMH in DCE Under Fluorescent Room Lighting

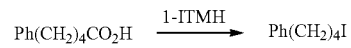

A mixture of 5-phenylvaleric acid (0.18 g, 1.0 mmol), 1-iodo-3,5,5-trimethylhydantoin (0.4 g, 1.5 mmol), and DCE (4 mL) was refluxed under fluorescent room lighting for 24 h and then concentrated in vacuo. The residue was treated with hexane (5 mL) and 1 M aq Na₂SO₃ (5 mL), extracted with hexane (2×5 mL). The combined hexane extracts were washed with 1 M aq Na₂SO₃ (5 mL), dried over Na₂SO₄, filtered through short neutral alumina pad and concentrated in vacuo to give 0.22 g (85%) of (4-iodobutyl)benzene.

Preparation of (4-iodobutyl)benzene with 1-ITMH in the Dark

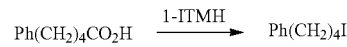

A mixture of 5-phenylvaleric acid (0.18 g, 1.0 mmol), 1-iodo-3,5,5-trimethylhydantoin 1-ITMH (0.4 g, 1.5 mmol), and DCE (4 mL) was refluxed in dark for 15 h and then concentrated in vacuo. The residue was treated with hexane (5 mL) and 1 M aq Na₂SO₃ (5 mL), extracted with hexane (2×5 mL). The combined hexane extracts were washed with 1 M aq Na₂SO₃ (5 mL), dried over Na₂SO₄, filtered through short neutral alumina pad and concentrated in vacuo to give 0.16 g (62%) of (4-iodobutyl)benzene.

Preparation of 1-(2-iodoethyl)-4-methoxybenzene with 1-ITMH

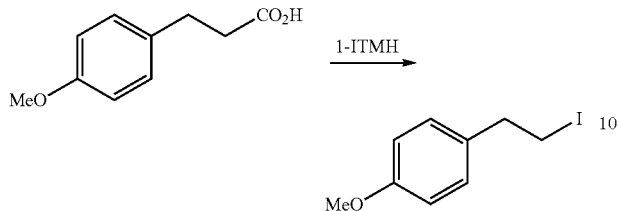

A mixture of 3-(4-methoxyphenyl)propanoic acid (0.18 g, 1.00 mmol), 1-iodo-3,5,5-trimethylhydantoin (0.34 g, 1.25 mmol), and DCM (5 mL) was refluxed under irradiation with tungsten lamp for 3 h and then concentrated in vacuo. The residue was treated with 1 M aq $Na_2SO_3$ (5 mL), and extracted with hexane (3×5 mL). The combined hexane extracts were washed with 1 M aq $Na_2SO_3$ (5 mL), dried over $Na_2SO_4$, filtered through short neutral alumina pad and concentrated in vacuo to give 0.17 g (63%) of 1-(2-iodoethyl)-4-methoxybenzene.

Preparation of 1-Acetyl-4-iodopiperidine with 1-ITMH

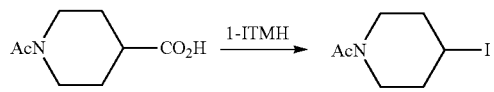

A mixture of 1-acetylpiperidine-4-carboxylic acid (0.17 g, 1.0 mmol), 1-iodo-3,5,5-trimethylhydantoin (0.34 g, 1.25 mmol), and DCM (5 mL) was refluxed under irradiation with tungsten lamp for 2 h and then concentrated in vacuo. The residue was treated with 1 M aq $Na_2SO_3$ (5 mL), and extracted with $CCl_4$ (2×5 mL). The combined organic extracts were washed with 1 M aq $Na_2SO_3$ (5 mL), dried over $Na_2SO_4$, filtered through short neutral alumina pad and concentrated in vacuo to give 0.12 g (46%) of 1-acetyl-4-iodopiperidine. $^1$H NMR: δ 7.94 (d, J=9.0 Hz, 2H), 7.91 (d, J=9.0 Hz, 2H) ppm; $^{13}$C NMR: δ 147.9, 138.8, 124.9, 102.8 ppm.

Preparation of 1-Iodo-4,7,7-trimethyl-2-oxabicyclo[2.2.1]heptan-3-one with 1-ITMH

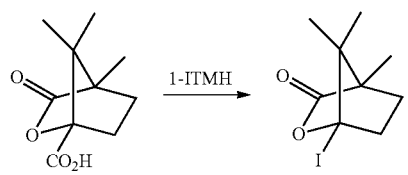

A mixture of camphanic acid (0.20 g, 1.0 mmol), 1-iodo-3,5,5-trimethylhydantoin (0.34 g, 1.25 mmol), and DCM (5 mL) was refluxed under irradiation with tungsten lamp for 2 h and then concentrated in vacuo. The residue was treated with 1 M aq $Na_2SO_3$ (5 mL) and extracted with hexane (2×5 mL). The combined organic extracts were washed with 1 M aq $Na_2SO_3$ (5 mL), dried over $Na_2SO_4$, filtered through short neutral alumina pad and concentrated in vacuo to give 0.17 g (60%) of 1-iodo-4,7,7-trimethyl-2-oxabicyclo[2.2.1]heptan-3-one. $^1$H NMR: δ 7.31 (m, 2H), 7.21 (m, 3H), 3.22 (t, J=6.9 Hz, 2H, $CH_2$—I), 2.66 (t, J=7.5 Hz, 2H), 1.87 (m, 2H), 1.77 (m, 2H); $^{13}$C NMR: δ 141.9, 128.5, 126.0, 34.9, 33.0, 32.3, 6.9 (C—I).

Example 10

Iododecarboxylation of Arylcarboxylic Acids

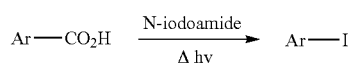

A mixture of $ArCO_2H$ (1 mmol), N-iodoamide, and solvent (5 mL) was refluxed (A) under irradiation with 250 W tungsten lamp (hv). The cold reaction mixture was washed with 1 M aq $Na_2SO_3$ (2×5 mL), dried over $Na_2SO_4$, filtered and concentrated in vacuo to obtain crude iodoarene Ar—I. The crude product was purified by chromatography on silica gel (eluent hexane/DCM 100:0 to 0:100). The results are presented in Table 17.

TABLE 10.1

Iododecarboxylation of arylcarboxylic acids using different iodoamides

| entry | reaction conditions | Ar—I, yield |
|---|---|---|
| 1 | DIH 1.5 mol/DCE, 15 h | 3-ClC$_6$H$_4$—I, 33% |
| 2 | 1-ITMH 2 mol/CCl$_4$, 24 h | 3-ClC$_6$H$_4$—I, 63% |
| 3 | IDMO 3 mol/DCE, 24 h | 3-ClC$_6$H$_4$—I, 27% |
| 4 | DIH 1.5 mol/DCE, 15 h | 4-ClC$_6$H$_4$—I, 13% |
| 5 | 1-ITMH 3 mol/DCE, 24 h | 4-ClC$_6$H$_4$—I, 68% |
| 6 | 1-ITMH 1.5 mol/DCE, 24 h | 4-ClC$_6$H$_4$—I, 35% |
| 7 | 1-ITMH 2 mol/CCl$_4$, 24 h | 4-ClC$_6$H$_4$—I, 35% |
| 8 | IDMO 3 mol/DCE, 24 h | 4-ClC$_6$H$_4$—I, 85% |
| 9 | IDMO 1.5 mol/DCE, 24 h | 4-ClC$_6$H$_4$—I, 24% |
| 10 | DIH 1.5 mol/DCE, 15 h | 3-BrC$_6$H$_4$—I, 41% |
| 11 | 1-ITMH 1.5 mol/CCl$_4$, 15 h | 3-BrC$_6$H$_4$—I, 61% |
| 12 | I-DMO 3 mol/DCE, 24 h | 3-BrC$_6$H$_4$—I, 33% |
| 13 | DIH 1 mol/DCE, 15 h | 4-BrC$_6$H$_4$—I, 12% |
| 14 | 1-ITMH 1.5 mol/DCE, 24 h | 4-BrC$_6$H$_4$—I, 37% |
| 15 | 1-ITMH 2 mol/CCl$_4$, 24 h | 4-BrC$_6$H$_4$—I, 37% |
| 16 | IDMO 3 mol/DCE, 24 h | 4-BrC$_6$H$_4$—I, 51% |
| 17 | DIH 1.5 mol/PhCl, 24 h | 2-O$_2$NC$_6$H$_4$—I, 72% |
| 18 | 1-ITMH 2 mol/CCl$_4$, 24 h | 2-O$_2$NC$_6$H$_4$—I, 93% |
| 19 | DIH 1.5 mol/PhCl, 24 h | 3-O$_2$NC$_6$H$_4$—I, 48% |
| 20 | 1-ITMH 2 mol/CCl$_4$, 24 h | 3-O$_2$NC$_6$H$_4$—I, 85% |
| 21 | 1-ITMH 3 mol/DCE, 48 h | 3-O$_2$NC$_6$H$_4$—I, 61% |
| 22 | IDMO 3 mol/DCE, 24 h | 3-O$_2$NC$_6$H$_4$—I, 66% |
| 23 | DIH 1.5 mol/PhCl, 24 h | 4-O$_2$NC$_6$H$_4$—I, 70% |
| 24 | 1-ITMH 3 mol/DCE, 48 h | 4-O$_2$NC$_6$H$_4$—I, 71% |
| 25 | 1-ITMH 2 mol/CCl$_4$, 24 h | 4-O$_2$NC$_6$H$_4$—I, 50% |
| 26 | IDMO 3 mol/DCE, 48 h | 4-O$_2$NC$_6$H$_4$—I, 56% |

Entries 1-3: 3-Chloroiodobenzene: $^1$H NMR: δ 7.72 (s, 1H), 7.59 (d, J=8.0, 1H), 7.32 (d, J=8.0, 1H), 7.03 (t, J=8.0, 1H) ppm; $^{13}$C NMR: δ 137.3, 135.8, 135.2, 131.1, 128.1, 94.2 ppm.

Entries 4-9: 4-Chloroiodobenzene: $^1$H NMR: δ 7.61 (d, J=8.5, 2H), 7.09 (d, J=8.5, 2H) ppm; $^{13}$C NMR: δ 138.8, 134.3, 130.6, 91.2 ppm.

Entries 10-12: 3-Bromoiodobenzene: $^1$H NMR: δ 7.87 (t, J=1.7 Hz, 1H), 7.63 (d, J=8.0 Hz, 1H), 7.46 (d, J=8.0 Hz, 1H), 6.97 (t, J=8.0, 1H) ppm; $^{13}$C NMR: δ 139.8, 136.2, 131.4, 130.9, 123.2, 94.6 ppm.

Entries 13-16: 4-Bromoiodobenzene: $^1$H NMR: δ 7.54 (d, J=8.5 Hz, 2H), 7.23 (d, J=8.5 Hz, 2H) ppm; $^{13}$C NMR: δ 139.2, 133.6, 122.3, 92.1 ppm.

Entries 17-18: 2-Nitroiodobenzene: $^1$H NMR: δ 8.05 (dd, J=8, 1 Hz, IH), 7.86 (dd, J=8, 1 Hz, 1H), 7.49 (m, 1H), 7.27 (m, 1H); $^{13}$C NMR: δ 153.2, 142.1, 133.5, 129.2, 125.4, 86.3 (C—I).

Entries 19-22: 3-Nitroiodobenzene: $^1$H NMR: δ 8.56 (s, 1H), 8.20 (d, J=8.3 Hz, 1H), 8.02 (d, J=8.3 Hz, 1H), 7.29 (t, J=8.3 Hz, 1H) ppm; $^{13}$C NMR: δ 148.6, 143.5, 132.5, 130.8, 122.8, 93.5 ppm.

Entries 23-26: 4-Nitroiodobenzene: $^1$H NMR: δ 7.94 (d, J=9.0 Hz, 2H), 7.91 (d, J=9.0 Hz, 2H) ppm; $^{13}$C NMR: δ 147.9, 138.8, 124.9, 102.8 ppm.

Example 11

Iododecarboxylation of o-Toluic Acid

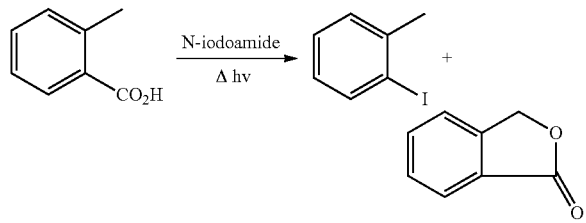

A mixture of o-toluic acid (1 mmol), N-iodoamide, and solvent (5 mL) was refluxed (Δ) under irradiation with 250 W tungsten lamp (hv) and concentrated in vacuo. The residue was treated with 1 M aq $Na_2SO_3$ (5 mL) and extracted with $CCl_4$ (2×10 mL). The combined organic extracts were washed with 1 M aq $Na_2SO_3$ (5 mL), dried over $Na_2SO_4$, filtered and concentrated in vacuo to obtain mixture of 2-iodotoluene and phthalide. The products ratio in the mixture was determined by $^1$H NMR. The results are presented in Table 18.

TABLE 11.1

Iododecarboxylation of o-toluic acid using different iodoamides

| entry | reaction conditions | 2-MeC$_6$H$_4$I/phthalide |
|---|---|---|
| 1 | DIH 1.2 mmol/DCE, 15 h | 0.8 |
| 2 | IDMO 1.5 mmol/DCE, 24 h | 0.8 |
| 3 | 1-ITMH 1.5 mmol/DCE, 24 h | 0.8 |
| 4 | 1-ITMH 1.5 mmol/DCM, 24 h | 0.5 |
| 5 | 1-ITMH 1.5 mmol/CCl$_4$, 24 h | 2.6 |

Example 12

Iododecarboxylation of Acrylic Acid Derivatives

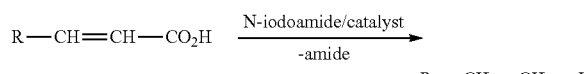

Note: All the reactions were provided in the dark

Preparation of (E)-1-(2-iodovinyl)-4-methoxybenzene Using DIH p-MeOC$_6$H$_4$CH=CHCO$_2$H $\xrightarrow{\text{DIH/Et}_3\text{N}}$ p-MeOC$_6$H$_4$CH=CH—I 1,3-Diiodo-5,5-dimethylhydantoin (0.23 g, 0.6 mmol) was added at rt to a stirred mixture of 4-methoxycinnamic acid (0.18 g, 1.0 mmol), Et$_3$N (7 mg, 0.07 mmol) and DCM (5 mL). The obtained mixture was stirred at rt for 2 h, washed with 1 M aq Na$_2$SO$_3$ (2×5 mL), dried over Na$_2$SO$_4$, filtered through short alumina pad and concentrated in vacuo to give 0.16 g (62%) of (E)-1-(2-iodovinyl)-4-methoxybenzene. $^1$H NMR: δ 7.35 (d, J=14.8 Hz, 1H), 7.23 (d, J=8.8 Hz, 2H), 6.84 (d, J=8.8 Hz, 2H), 6.62 (d, J=14.8 Hz, 1H), 3.80 (s, 3H) ppm; $^{13}$C NMR: δ 159.9, 144.4, 130.8, 127.4, 114.2, 73.7, 55.4 ppm.

Preparation of (E)-1-(2-iodovinyl)-4-methoxybenzene Using IDMO p-MeOC$_6$H$_4$CH=CHCO$_2$H $\xrightarrow{\text{IDMO/Et}_3\text{N}}$ p-MeOC$_6$H$_4$CH=CH—I 3-Iodo-4,4-dimethyloxazolidin-2-one (0.29 g, 1.2 mmol) was added at rt to a stirred mixture of 4-methoxycinnamic acid (0.18 g, 1.0 mmol), Et$_3$N (7 mg, 0.07 mmol), and DCM (5 mL). The obtained mixture was stirred at rt for 2 h and concentrated in vacuo. A solution of the residue in hexane (10 mL) was washed with 1 M aq Na$_2$SO$_3$ (2×10 mL), dried over Na$_2$SO$_4$, filtered through short alumina pad and concentrated in vacuo to give 0.14 g (62%) of (E)-1-(2-iodovinyl)-4-methoxybenzene.

Preparation of (E)-1-(2-iodovinyl)-4-methoxybenzene Using 1-ITMH p-MeOC$_6$H$_4$CH=CHCO$_2$H $\xrightarrow{\text{1-ITMH/Et}_3\text{N}}$ p-MeOC$_6$H$_4$CH=CH—I 1-Iodo-3,5,5-trimethylhydantoin (0.32 g, 1.2 mmol) was added at rt to a stirred mixture of 4-methoxycinnamic acid (0.18 g, 1.0 mmol), Et$_3$N (7 mg, 0.07 mmol) and DCM (5 mL). The obtained mixture was stirred at rt for 2 h and concentrated in vacuo. A solution of the residue in hexane (10 mL) was washed with 1 M aq Na$_2$SO$_3$ (2×10 mL), dried over Na$_2$SO$_4$, filtered through short alumina pad and concentrated in vacuo to give 0.19 g (75%) of (E)-1-(2-iodovinyl)-4-methoxybenzene.

Example 13

Iododecarboxylation of Propiolic Acid Derivatives

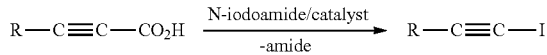

Note: All the reactions were provided in the dark

Preparation of (Iodoethynyl)Benzene Using DIH

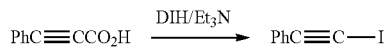

1,3-Diiodo-5,5-dimethylhydantoin (0.23 g, 0.6 mmol) was added to a stirred solution of phenylpropiolic acid (0.15 g, 1.0 mmol), Et₃N (7 mg, 0.07 mmol) and DCM (5 mL). The obtained mixture was stirred at rt for 5 min, washed with 1 M aq Na₂SO₃ (2×5 mL), dried over Na₂SO₄, filtered through short alumina pad and concentrated in vacuo to give 0.21 g (92%) of (iodoethynyl)benzene. $^1$H NMR: δ 7.46-7.42 (m, 2H), 7.33-7.30 (m, 3H) ppm; $^{13}$C NMR: δ 132.4, 128.9, 128.3, 123.5, 94.3, 6.2 ppm.

Preparation of (Iodoethynyl)Benzene Using IDMO

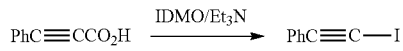

3-Iodo-4,4-dimethyloxazolidin-2-one (0.29 g, 1.2 mmol) was added at rt to a stirred mixture of phenylpropiolic acid (0.15 g, 1.0 mmol), Et₃N (7 mg, 0.07 mmol) and DCM (5 mL). The obtained mixture was stirred at rt for 5 min and concentrated in vacuo. A solution of the residue in hexane (10 mL) was washed with 1 M aq Na₂SO₃ (2×10 mL), dried over Na₂SO₄, filtered through short alumina pad and concentrated in vacuo to give 0.22 g (96%) of (iodoethynyl)benzene.

Preparation of (Iodoethynyl)Benzene Using 1-ITMH

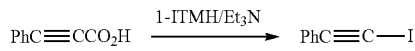

1-Iodo-3,5,5-trimethylhydantoin (0.32 g, 1.2 mmol) was added at rt to a stirred mixture of phenylpropiolic acid (0.15 g, 1.0 mmol), Et₃N (7 mg, 0.07 mmol) and DCM (5 mL). The obtained mixture was stirred at rt for 5 min and concentrated in vacuo. A solution of the residue in hexane (10 mL) and washed with 1 M aq Na₂SO₃ (2×10 mL), dried over Na₂SO₄, filtered through short alumina pad and concentrated in vacuo to give 0.22 g (97%) of (iodoethynyl) benzene.

Example 14

Iodination of alkenes with 3-iodo-4,4-dimethyloxazolidin-2-one (IDMO) and Recovery of 4,4-dimethyloxazolidin-2-one (DMO)

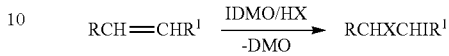

Preparation of 2-trans-iodocyclohexanol with IDMO and Recovery of 4,4-dimethyloxazolidin-2-one

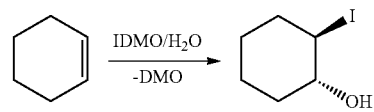 [SMILES: C1=CCCCC1 ; O[C@@H]1CCCC[C@H]1I]

3-Iodo-4,4-dimethyloxazolidin-2-one (0.48 g, 2.0 mmol) was added to a stirred solution of cyclohexene (0.16 g, 2.0 mmol) and water (2.5 mL) in acetone (12.5 mL) at 0-5° C. The mixture was stirred for 2 h at rt and concentrated in vacuo. A mixture of the residue with 1 M aq Na₂SO₃ (2.5 mL) was extracted with hexane (3×10 mL) and then with DCM (3×10 mL). The combined DCM extracts were dried over Na₂SO₄, filtered and concentrated in vacuo to give 0.16 g (70%) of 4,4-dimethyl-2-oxazolidinone. The combined hexane extracts were washed with 1 M aq Na₂SO₃ (10 mL), dried over Na₂SO₄, filtered and concentrated in vacuo to give 0.39 g (87%) of 2-trans-iodocyclohexanol. $^1$H NMR: δ 4.06-3.98 (m, 1H), 3.68-3.59 (m, 1H), 2.4-2.39 (m, 2H), 2.14-1.96 (m, 2H), 1.87-1.78 (m, 1H), 1.55-1.47 (m, 1H), 1.45-1.18 (m, 3H) ppm; $^{13}$C NMR: δ 77.0, 43.4, 38.7, 33.7, 28.0, 24.5 ppm.

Preparation of trans-1-Iodo-2-methoxycyclohexane

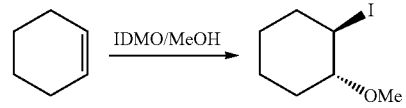 [SMILES: C1=CCCCC1 ; CO[C@@H]1CCCC[C@H]1I]

3-Iodo-4,4-dimethyloxazolidin-2-one (0.48 g, 2.0 mmol) was added to a stirred solution of the cyclohexene (0.14 g, 2.0 mmol) in MeOH (5 mL) at 0-5° C. The mixture was stirred for 2 h at rt and concentrated in vacuo. The residue was treated with 1 M aq Na₂SO₃ (5 mL) and extracted with hexane (3×5 mL). The combine organic phase was washed with 1 M aq Na₂SO₃ (5 mL), dried over Na₂SO₄, filtered and concentrated in vacuo to give 0.36 g (75%) of trans-1-iodo-2-methoxycyclohexane. $^1$H NMR: δ 4.09-4.00 (m, 1H), 3.38 (s, 3H), 3.26-3.18 (m, 1H), 2.41-2.38 (m, 1H), 2.21-2.13 (m, 1H), 2.01-1.90 (m, 1H), 1.84-1.76 (m, 1H), 1.56-1.47 (m, 1H), 1.38-1.20 (m, 3H) ppm; $^{13}$C NMR: δ 83.9, 56.9, 37.8, 35.4, 30.3, 27.2, 23.6 ppm.

Preparation of trans-2-iodocyclohexyl acetate

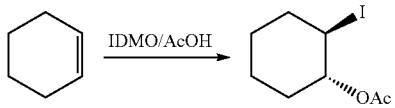 [SMILES: C1=CCCCC1 ; CC(=O)O[C@@H]1CCCC[C@H]1I]

3-Iodo-4,4-dimethyloxazolidin-2-one (0.48 g, 2.0 mmol) was added to a stirred solution of the cyclohexene (0.14 g, 2.0 mmol) in AcOH (5 mL). The mixture was stirred for 2 h at rt, diluted with water (10 mL) and extracted with hexane (3×10 mL). The combine hexane extracts were washed with 1 M aq Na$_2$SO$_3$ (10 mL), dried over Na$_2$SO$_4$, filtered and concentrated in vacuo to give 0.44 g (83%) trans-2-iodocyclohexyl acetate. $^1$H NMR: δ 4.92-4.84 (m, 1H), 4.08-4.00 (m, 1H), 2.47-2.39 (m, 1H), 2.07 (s, 3H), 2.05-1.95 (m, 2H), 1.84-1.76 (m, 1H), 1.60-1.52 (m, 1H), 1.48-1.23 (m, 3H) ppm; $^{13}$C NMR: δ 170.0, 76.7, 37.9, 31.9, 31.7, 27.1, 23.6, 21.3 ppm.

Preparation of 2-iodo-1-phenylethanol

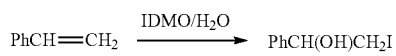

3-Iodo-4,4-dimethyloxazolidin-2-one (0.48 g, 2.0 mmol) was added to a stirred solution of the styrene (0.21 g, 2.0 mmol) and water (2.5 mL) in acetone (12.5 mL) at 0-5° C. The mixture was stirred at rt for 3 h and concentrated in vacuo. The residue was treated with 1 M aq Na$_2$SO$_3$ (5 mL) and extracted with hexane (3×5 mL). The combined organic extracts were washed with 1 M aq Na$_2$SO$_3$ (5 mL), dried over Na$_2$SO$_4$, filtered and concentrated in vacuo to give 0.44 g (90%) of 2-iodo-1-phenylethanol. $^1$H NMR: δ 7.39-7.30 (m, 5H), 4.85-4.80 (m, 1H), 3.49 (dd, J=3.5 Hz, J=10.3 Hz, 1H), 3.40 (t, J=9.8 Hz, 1H), 2.57 (d, J=3.5 Hz, 1H) ppm; $^{13}$C NMR: δ 141.2, 128.8, 128.4, 125.8, 74.14, 15.4 ppm.

Preparation of (2-Iodo-1-methoxyethyl)benzene

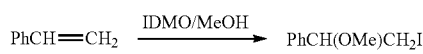

3-Iodo-4,4-dimethyloxazolidin-2-one (0.48 g, 2.0 mmol) was added to a stirred solution of styrene (0.21 g, 2.0 mmol) in MeOH (5 mL) at 0-5° C. The mixture was stirred for 3 h at rt and concentrated in vacuo. The residue was treated with 1 M aq Na$_2$SO$_3$ (5 mL) and extracted with hexane (3×5 mL). The combined organic extracts were washed with 1 M aq Na$_2$SO$_3$ (5 mL), dried over Na$_2$SO$_4$, filtered and concentrated in vacuo to give 0.47 g (90%) of (2-iodo-1-methoxyethyl)benzene. $^1$H NMR: δ 7.41-7.29 (m, 5H), 4.33-4.27 (m, 1H), 3.37-3.32 (m, 2H), 3.31 (s, 3H) ppm; $^{13}$C NMR: δ 139.8, 128.8, 128.5, 126.6, 83.6, 57.4, 10.5 ppm.

Preparation of 2-Iodo-1-phenyl acetate

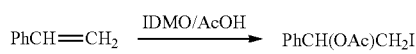

3-Iodo-4,4-dimethyloxazolidin-2-one (0.48 g, 2.0 mmol) was added to a stirred solution of styrene (0.21 g, 2.0 mmol) in AcOH (5 mL). The mixture was stirred for 2 h at rt, treated with water (10 mL) and extracted with hexane (3×10 mL). The combined hexane extracts were washed with 1 M aq Na$_2$SO$_3$ (2×10 mL), dried over Na$_2$SO$_4$, filtered and concentrated in vacuo to give 0.55 g (94%) of 2-iodo-1-phenylethyl acetate. $^1$H NMR: δ 7.41-7.32 (m, 5H), 5.91-5.85 (m, 1H), 3.50-3.44 (m, 2H), 2.13 (s, 3H) ppm; $^{13}$C NMR: δ 169.9, 138.5, 128.8, 126.5, 125.8, 75.2, 21.1, 7.9 ppm.

Example 15

Iodination of Alkene with 1-ITMH

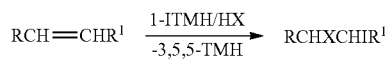

Preparation of 2-iodo-1-phenylethanol with 1-ITMH and Recovery of 3,5,5-trimethylhydantoin

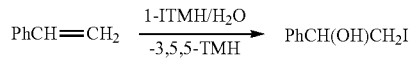

1-Iodo-3,5,5-trimethylhydantoin (0.56 g, 2.1 mmol) was added to a stirred solution of styrene (0.22 g, 2.1 mmol) and water (2.5 mL) in acetone (12.5 mL) at 0-5° C. The mixture was stirred for 3 h at rt and concentrated in vacuo. The residue was treated with 1 M aq Na$_2$SO$_3$ (5 mL), extracted with hexane (3×10 mL) and then with DCM (3×10 mL). The combined DCM extracts were dried over Na$_2$SO$_4$, filtered and concentrated in vacuo to give 0.22 g (75%) of 3,5,5-trimethylhydantoin. The combined hexane extracts were washed with 1 M aq Na$_2$SO$_3$ (10 mL), dried over Na$_2$SO$_4$, filtered and concentrated in vacuo to give 0.42 g (82%) of 2-iodo-1-phenylethanol.

Example 16

Iodination of Alkene with N-Iodosaccharin (NISac)

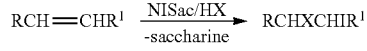

Preparation of 2-iodo-1-phenylethanol with NISac and Recovery of Saccharin

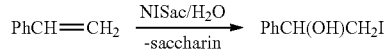

N-Iodosaccharin (0.62 g, 2.0 mmol) was added to a stirred solution of styrene (0.21 g, 2.0 mmol) and water (2.5 mL) in acetone (12.5 mL) at 0-5° C. The mixture was stirred at rt for 1 h and concentrated in vacuo. The residue was treated with 1 M aq Na$_2$SO$_3$ (5 mL) and extracted with DCM (2×10 mL). The aqueous layer was acidified with conc HCl to pH 1 and stirred for 1 h at rt and 2 h at 0-5° C. Precipitated solid was filtered off, washed on the filter with cold water (2 mL), and dried in vacuo to give 0.26 g (70%) of saccharin. The combined DCM extracts were washed with 1 M aq Na$_2$SO$_3$ (5 mL), dried over Na$_2$SO$_4$, filtered and concentrated in vacuo to give 0.42 g (82%) of 2-iodo-1-phenylethanol.

Example 17

Aromatic Hydrocarbons. Nuclear Iodination

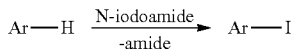

Note: The reactions were provided in the dark

Preparation of 4-iodo-1,2-dimethoxybenzene with IDMO and Recovery of DMO

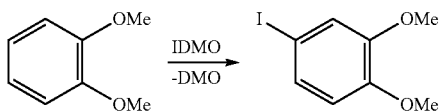

A mixture of veratrole (0.22 g, 1.63 mmol), 3-iodo-4,4-dimethyloxazolidin-2-one (0.6 g, 2.44 mmol) and MeCN (10 mL) was stirred under reflux conditions for 15 h and concentrated in vacuo. The residue was treated with 1 M aq Na$_2$SO$_3$ (5 mL), extracted with hexane (3×10 mL) and then with DCM (3×10 mL). The combined DCM extracts were dried over Na$_2$SO$_4$, filtered and concentrated in vacuo to give 0.27 g (95%) of 4,4-dimethyl-2-oxazolidinone. The combined hexane extracts were washed with 1 M aq Na$_2$SO$_3$ (10 mL), dried over Na$_2$SO$_4$, filtered and concentrated in vacuo. The residue was purified by chromatography on silica gel (eluent hexane/DCM 100:0 to 0:100 v/v) to give 0.36 g (85%) of 4-iodo-1,2-dimethoxybenzene. $^1$H NMR: δ 7.19 (dd, J=1.5 Hz, J=8.5 Hz, 1H), 7.09 (d, J=1.5 Hz, 1H), 6.59 (d, J=8.5 Hz, 1H), 3.83 (s, 3H), 3.82 (s, 3H) ppm; $^{13}$C NMR: δ 149.8, 149.1, 129.7, 120.3, 113.2, 82.3, 56.1, 55.9 ppm.

Preparation of 4-iodo-1,2-dimethoxybenzene with 1-ITMH and Recovery of 3,5,5 TMH

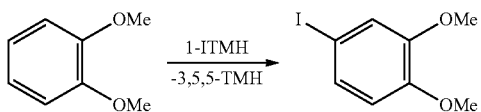 [SMILES: COc1ccccc1OC ; "1-ITMH" ; COc1ccc(I)cc1OC]

A mixture of veratrole (0.22 g, 1.63 mmol), 1-iodo-3,5,5-trimethylhydantoin (0.53 g, 1.97 mmol) and MeCN (10 mL) was stirred for 48 h at rt and concentrated in vacuo. The residue was treated with 1 M aq Na$_2$SO$_3$ (5 mL), extracted with hexane (3×10 mL) and then with DCM (3×10 mL). The combined DCM extracts were dried over Na$_2$SO$_4$, filtered and concentrated in vacuo to give 0.25 g (90%) of 3,5,5-trimethylhydantoin (3,5,5-TMH). The combined hexane extracts were washed with 1 M aq Na$_2$SO$_3$ (10 mL), dried over Na$_2$SO$_4$, filtered and concentrated in vacuo. The residue was purified by chromatography on silica gel (eluent hexane/DCM 100:0 to 0:100 v/v) to give 0.31 g (61%) of 4-iodo-1,2-dimethoxybenzene.

Preparation of 1,2-diiodo-4,5-dimethoxybenzene with 1-ITMH

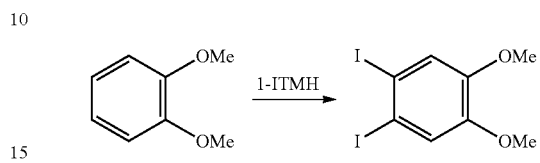

A mixture of veratrole (0.21 g, 1.52 mmol), 1-iodo-3,5,5-trimethylhydantoin (1.10 g, 2.50 mmol) and MeCN (10 mL) was stirred for 24 h under reflux conditions and concentrated in vacuo. A mixture of the residue with 1 M aq Na$_2$SO$_3$ (5 mL) and hexane (5 mL) was stirred for 0.5 h at rt and for 2 h at 0-5° C. Precipitated solid was filtered off, washed on the filter with water and cold hexane, and dried in vacuo to obtain 0.42 g (75%) of 1,2-diiodo-4,5-dimethoxybenzene. $^1$H NMR: δ 7.19 (dd, J=1.5 Hz, J=8.5 Hz, 1H), 7.09 (d, J=1.5 Hz, 1H), 6.59 (d, J=8.5 Hz, 1H), 3.83 (s, 3H), 3.82 (s, 3H) ppm; $^{13}$C NMR: δ 149.8, 149.1, 129.7, 120.3, 113.2, 82.3, 56.1, 55.9 ppm.

Example 18

Methyl Arenes. Side-Chain Versus Nuclear Iodination

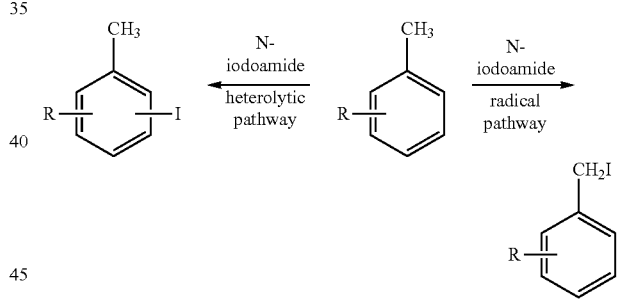

Iodination of Toluene Under Fluorescence Light Irradiation

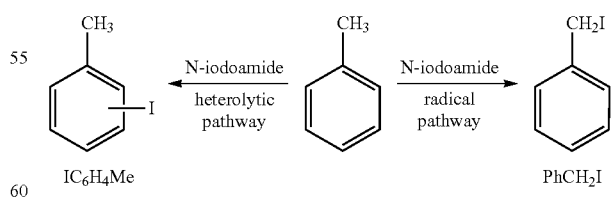

A mixture of N-iodoamide (51 mg, 0.19 mmol), toluene (1 mL) and CCl$_4$ (4 mL) was stirred under reflux conditions (A) and fluorescence light irradiation (hv) for 48 h. The reaction mixture was analyzed by GC. The experimental results of iodination toluene by different N-iodoamides are presented in Table 18.1.

TABLE 18.1

Iodination of toluene under fluorescence light irradiation

| N-Iodoamide | Yield, %[a] | |
|---|---|---|
| | PhCH$_2$I | IC$_6$H$_4$Me |
| NIS | 14 | 0 |
| DIH | 13 | 0 |
| IPT | 3 | 0 |
| INPT | 1 | 0 |
| NISac | 0 | 8 |
| IDMO | 48 | 0 |
| 3-ITMH | 3 | 0 |
| 1-ITMH | 59 | 0 |

[a]GC yield

Wohl-Ziegler Iodination of Methyl Arenes with 1-ITMH

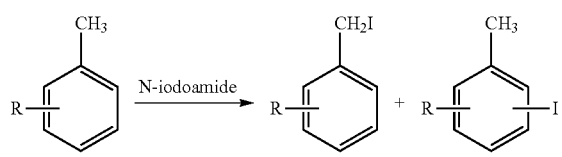

A mixture of 1-iodo-3,5,5-trimethylhydantoin (1-ITMH) (51 mg, 0.19 mmol), ArMe (1 mL) and solvent (4 mL) was stirred under reflux conditions (Δ) and fluorescence light irradiation (FL) or in the dark (NL). The reaction mixture was analyzed by GC. The experimental results of side-chain and nuclear iodination of methyl arenes are presented in Table 18.2.

TABLE 18.2

Side-chain and nuclear iodination of methyl arenes

| entry | ArMe | Solvent, time, illumination | ArCH$_2$I, yield[a] | | Nuclear iodination, yield[a] |
|---|---|---|---|---|---|
| 1 | PhMe | CCl$_4$, 48 h, FL | PhCH$_2$I, | 59% | 0% |
| 2 | PhMe | CCl$_4$, 48 h, NL | PhCH$_2$I, | 9% | 10% |
| 3 | o-C$_6$H$_4$Me$_2$ | CCl$_4$, 48 h, FL | 2-MeC$_6$H$_4$CH$_2$I, | 67% | |
| 4 | m-C$_6$H$_4$Me$_2$ | CCl$_4$, 48 h, FL | 3-MeC$_6$H$_4$CH$_2$I, | 76% | |
| 6 | p-C$_6$H$_4$Me$_2$ | CCl$_4$, 48 h, FL | 4-MeC$_6$H$_4$CH$_2$I, | 64% | |
| 7 | 1,3,5-C$_6$H$_3$Me$_3$ | CCl$_4$, 48 h, FL | 3,5-Me$_2$C$_6$H$_3$CH$_2$I, | 62% | 9% |
| 8 | 1,3,5-C$_6$H$_3$Me$_3$ | CCl$_4$, 48 h, NL | 3,5-Me$_2$C$_6$H$_3$CH$_2$I, | 15% | 48% |
| 9 | 1,3,5-C$_6$H$_3$Me$_3$ | MeCN, 48 h, NL | 3,5-Me$_2$C$_6$H$_3$CH$_2$I, | 0% | 89% |
| 10 | 4-FC$_6$H$_4$Me | CCl$_4$, 48 h, FL | 4-FC$_6$H$_4$CH$_2$I, | 59% | 0% |
| 11 | 4-ClC$_6$H$_4$Me | CCl$_4$, 48 h, FL | 4-ClC$_6$H$_4$CH$_2$I, | 71% | 0% |
| 12 | 3-O$_2$NC$_6$H$_4$Me | CCl$_4$, 48 h, FL | 3-O$_2$NC$_6$H$_4$CH$_2$I, | 40% | 0% |

[a]GC yield

Wohl-Ziegler Iodination of Toluene with 1-ITMH and Recovery of 3,5,5-TMH

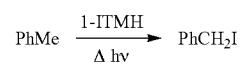

A mixture of 1-iodo-3,5,5-trimethylhydantoin (0.51 g, 1.9 mmol), toluene (10 mL), and CCl$_4$ (40 mL) was stirred under reflux conditions (Δ) and fluorescence light irradiation (hv) for 48 h. The cold reaction mixture was washed with 1 M aq Na$_2$SO$_3$ (2×50 mL), dried over Na$_2$SO$_4$, filtered and concentrated in vacuo. The residue was purified by chromatography on silica gel (eluent-pentane) to give 0.14 g (33%) of benzyl iodide. $^1$H NMR: δ 7.24 (d, J=7.2 Hz, 2H), 7.10-7.17 (m, 3H), 4.30 (s, 2H) ppm; $^{13}$C NMR: δ 139.3, 128.82, 128.77, 127.9, 6.0 ppm.

The combine aq sodium sulfite washings were extracted with DCM (3×50 mL).

The combine DCM extracts were dried over Na$_2$SO$_4$, filtered and concentrated in vacuo to obtain 0.23 g (85%) of 3,5,5-trimethylhydantoin.

Nuclear Iodination of m-Xylene in the Dark

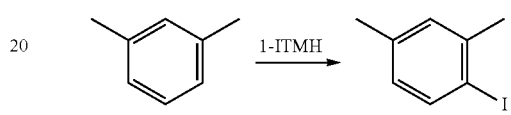

A mixture of m-xylene (0.20 g, 1.88 mmol), 1-iodo-3,5,5-trimethylhydantoin (0.63 g, 2.35 mmol) and MeCN (10 mL) was stirred for 48 h in the dark under reflux conditions and concentrated in vacuo. The residue was treated with 1 M aq Na$_2$SO$_3$ (10 mL) and extracted with hexane (3×10 mL). The combined organic extracts were washed with 1 M aq Na$_2$SO$_3$ (10 mL), dried over Na$_2$SO$_4$, filtered and concentrated in vacuo. The residue was purified by chromatography on silica gel (eluent hexane) to give 0.30 g (68%) of 1-iodo-2,4-dimethylbenzene. $^1$H NMR: δ 7.19 (dd, J=1.5 Hz, J=8.5 Hz, 1H), 7.09 (d, J=1.5 Hz, 1H), 6.59 (d, J=8.5 Hz, 1H), 3.83 (s, 3H), 3.82 (s, 3H) ppm; $^{13}$C NMR: δ 149.8, 149.1, 129.7, 120.3, 113.2, 82.3, 56.1, 55.9 ppm.

Example 19

Iodination of Aliphatic Hydrocarbons with N-Iodoamides

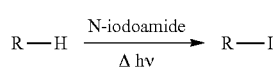

Iodination of Cyclohexane by Different N-Iodoamides

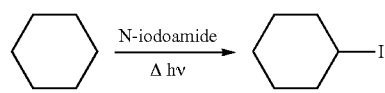 [SMILES: C1CCCCC1 ; IC1CCCCC1]

A mixture of N-iodoamide (0.19 mmol) and cyclohexane (5 mL) was stirred under reflux conditions (Δ) and irradiation with 250 W tungsten lamp (hv) for 2 h. The reaction mixture was analyzed by GC. The experimental results of iodination cyclohexane by different N-iodoamides are presented in Table 19.1.

TABLE 19.1

Iodination of cyclohexane by N-iodoamides

| N-Iodoamide | Yield, %[a] |
|---|---|
| NIS | 4 |
| DIH | 10 |
| IPT | 4 |
| INPT | 0 |
| NISac | 11 |
| IDMO | 56 |
| 3-ITMH | 1 |
| 1-ITMH | 82 |
| 1-ITMH | 8[b] |

[a]GC yield;
[b]reflux 2 h in the dark

Iodination of Alkanes with 1-iodo-3,5,5-trimethylhydantoin

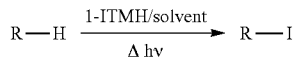

A mixture of 1-iodo-3,5,5-trimethylhydantoin (1-ITMH) (1.9 mmol), alkane R—H (10 mL) and solvent (40 mL) was stirred under reflux conditions (Δ) and irradiation with 250 W tungsten lamp (hv). The reaction mixture was analyzed by GC. For product isolation the reaction mixture was washed with aq $Na_2SO_3$ and dried over $Na_2SO_4$. The solvent was removed by distillation, and the residue was purified by chromatography on silica gel (eluent-pentane). The experimental results of alkanes iodination with 1-iodo-3,5,5-trimethylhydantoin are presented in Table 19.2.

TABLE 19.2

Iodination of alkanes by 1-ITMH

| entry | R—H | solv. | time | R—I | yield, %[a] |
|---|---|---|---|---|---|
| 1 | $c$-$C_5H_{10}$ | $CCl_4$ | 1 h | $c$-$C_5H_9I$ | 70 |
| 2 | $c$-$C_6H_{12}$ | $c$-$C_6H_{12}$ | 2 h | $c$-$C_6H_{11}I$ | 82 (62) |
| 3 | $c$-$C_7H_{14}$ | $CCl_4$ | 1 h | $c$-$C_7H_{13}I$ | 66 |
| 4 | $c$-$C_8H_{16}$ | $CCl_4$ | 0.5 h | $c$-$C_8H_{15}I$ | 90 (69) |
| 5 | $c$-$C_6H_{14}$ | $CCl_4$ | 2 h | PrCHIEt(35%) BuCHIMe(58%) H($CH_2$)$_6$I(7%) | 58 |
| 6 | BuCl | BuCl | 4 h | PrCHICl (34%) EtCHICH$_2$Cl (17%) MeCHI(CH$_2$)$_2$Cl (42%) Cl(CH$_2$)$_4$I (7%) | 42 |
| 7 | (ClCH$_2$)$_2$ | (ClCH$_2$)$_2$ | 24 h | ClCH$_2$CHICl | 59 (51) |
| 8 | t-BuPh | $CCl_4$ | 6 h | PhCMe$_2$CH$_2$I | 14 |
| 9 | 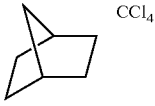 | $CCl_4$ | 2 h |  31% 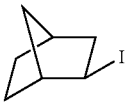 69% | 59[b] |

[a]GC yield of R—I, in parentheses- isolated yield, ratio of isomers was determined by GC; [b]ratio of isomers was determined by $^1$H NMR.

Entry 1: Iodocyclohexane $^1$H NMR: δ 4.35 (m, 1H), 2.13 (m, 2H), 1.93-1.99 (m, 2H), 1.60-1.70 (m, 3H), 1.30-1.40 (m, 3H) ppm; $^{13}$C NMR: δ 36.7, 32.8, 27.4, 25.3 ppm; HRMS-APSI: (M)$^+$209.9900, $C_6H_{11}I$ calc. mass 209.9906.

Entry 4: Iodocyclooctane: $^1$H NMR: δ 4.57 (m, 1H), 2.2-2.23 (m, 4H), 1.4-1.7 (m. 10H) ppm; $^{13}$C NMR: δ 38.2, 37.0, 27.5, 26.7, 25.2 ppm; HRMS-ESI: (M+H)$^+$239.0267, $C_8H_{16}I$ calc. mass 239.0297.

Entry 7: 1,2-Dichloro-1-iodoethane: $^1$H NMR: δ 5.71 (dd, J=8.3, 4.8 Hz, 1H), 4.16 (dd, J=12.0, 4.8 Hz, 1H), 4.03 (dd, J=12.0, 8.3 Hz, 1H) ppm; $^{13}$C NMR: δ 53.0, 25.7 ppm; HRMS-ESI: (M)$^+$223.8650, $C_2H_3Cl_2I$ calc. mass 223.8650.

Iodination of Cyclohexane with 1-ITMH and Recovery of 3,5,5-TMH

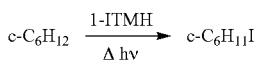

A mixture of 1-iodo-3,5,5-trimethylhydantoin (0.51 g, 1.9 mmol) and cyclohexane (50 mL) was stirred under reflux conditions (Δ) and irradiation with 250 W tungsten lamp (hv) for 48 h. The cold reaction mixture was washed with 1 M aq $Na_2SO_3$ (2×50 mL), dried over $Na_2SO_4$, and filtered. Cyclohexane was removed by distillation. The residue was purified by chromatography on silica gel (eluent-pentane) to give 0.25 g (62%) of iodocyclohexane.

The combine aq sodium sulfite washings were extracted with DCM (3×50 mL). The combine DCM extracts were dried over $Na_2SO_4$, filtered and concentrated in vacuo to obtain 0.19 g (71%) of 3,5,5-trimethylhydantoin.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A process for the preparation of organic iodide comprising the steps of:
   (a) reacting an amide with iodine and [bis(acyloxy)iodo]arene in an aprotic solvent to yield N-iodoamide and iodoarene as co-product;
   (b) reacting an organic compound with said N-iodoamide of step (a) to yield desired organic iodide and amide as co-product; and
   (c) recovering said amide co-product from the reaction mixture of step (b);
   wherein said amide is 4,4-dimethyloxazolidin-2-one, saccharin or 3,5,5-trimethylhydantoin and said N-iodoamide is 3-iodo-4,4-dimethyloxazolidin-2-one (IDMO), N-iodosaccharin (NISac) or 1-iodo-3,5,5-trimethylhydantoin (1-ITMH), respectively.

2. The process of claim 1, wherein said organic compound is a carboxylic acid, an alkene, an alkyne, an alkane, a cycloalkane, methylarene, ketone, aromatic compound or combination thereof.

3. The process of claim 2, wherein said carboxylic acid is a compound of formula R—CO$_2$H and said N-iodoamide is 1-iodo-3,5,5-trimethylhydantoin (1-ITMH) or 3-iodo-4,4-dimethyl-2-oxazolidinone (IDMO); wherein R is saturated, linear or branched, substituted or unsubstituted alkyl; substituted or unsubstituted aryl; substituted or unsubstituted Ph(CH$_2$)$_p$— wherein p is an integer between 1 and 6, saturated substituted or unsubstituted cycloalkyl, heterocycloalkyl or combination thereof and wherein said organic iodide is R—I;
   wherein said reaction of step (b) is radical iododecarboxylation represented by scheme (1):

R—CO$_2$H+N-iodoamide→R—I+amide    (1)

wherein said reaction is provided under visual light irradiation of the reaction mixture.

4. The process of claim 2, wherein said carboxylic acid is acrylic acid derivative of formula R—CH=CH—CO$_2$H; said N-iodoamide is 1-iodo-3,5,5-trimethylhydantoin (1-ITMH), 3-iodo-4,4-dimethyl-2-oxazolidinone (IDMO), or N-iodosaccharin (NISac); wherein R is saturated, linear or branched, substituted or unsubstituted alkyl; substituted or unsubstituted aryl; substituted or unsubstituted Ph(CH$_2$)$_p$— wherein p is an integer between 1 and 6; saturated or unsaturated, substituted or unsubstituted cycloalkyl or heterocycloalkyl or combination thereof; and wherein said organic iodide is R—CH=CH—I;
   wherein said reaction of step (b) is electrophylic iododecarboxylation of acrylic acid derivative represented by scheme (2):

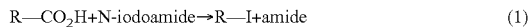
   R—CH=CH—CO$_2$H+N-iodoamide→R—CH=CH—I+amide    (2)

wherein said reaction is provided under heterolytic reaction conditions; wherein said reaction further comprises a catalyst, wherein said catalyst is an organic base, LiOAc, Bu$_4$N$^+$, or CF$_3$CO$_2^-$.

5. The process of claim 2, wherein said carboxylic acid is propiolic acid derivative of formula R—C≡C—CO$_2$H; wherein said N-iodoamide is 1-iodo-3,5,5-trimethylhydantoin (1-ITMH), 3-iodo-4,4-dimethyl-2-oxazolidinone (IDMO), or N-iodosaccharin (NISac); wherein R is saturated, linear or branched, substituted or unsubstituted alkyl; substituted or unsubstituted Ph(CH$_2$)$_p$— wherein p is an integer between 1 and 6; substituted or unsubstituted aryl; saturated or unsaturated, substituted or unsubstituted cycloalkyl or heterocycloalkyl ring or combination thereof; and wherein said organic iodide is R—C≡C—I;

wherein said reaction of step (b) is electrophylic iododecarboxylation of propiolic acid derivative represented by scheme (3):

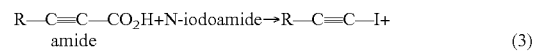
   R—C≡C—CO$_2$H+N-iodoamide→R—C≡C—I+amide    (3)

wherein said reaction is provided under heterolytic reaction conditions; said reaction further comprises a catalyst, wherein said catalyst is an organic base, LiOAc, Bu$_4$N$^+$, or CF$_3$CO$_2^-$.

6. The process of claim 2, wherein said aromatic compound is a compound of formula Ar—H, said N-iodoamide is 1-iodo-3,5,5-trimethylhydantoin (1-ITMH), 3-iodo-4,4-dimethyl-2-oxazolidinone (IDMO), or N-iodosaccharin (NISac); wherein said Ar is substituted or unsubstituted aryl group; and wherein said organic iodide is Ar—I;
   wherein said reaction of step (b) is electrophilic aromatic iodination represented by scheme (4):

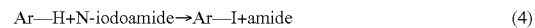
   Ar—H+N-iodoamide→Ar—I+amide    (4)

wherein said reaction is provided under heterolytic reaction conditions.

7. The process of claim 2, wherein said methylarene is compound of formula ArCH$_3$; said N-iodoamide is 1-iodo-3,5,5-trimethylhydantoin (1-ITMH) or 3-iodo-4,4-dimethyl-2-oxazolidinone (IDMO); wherein said Ar is substituted or unsubstituted aryl group; and wherein said organic iodide is ArCH$_2$I;
   wherein said reaction of step (b) is a radical iodination of methyl group of methylarene represented by scheme (5):

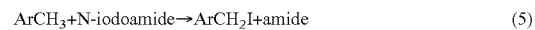
   ArCH$_3$+N-iodoamide→ArCH$_2$I+amide    (5)

wherein said reaction is provided under visual light irradiation of the reaction mixture.

8. The process of claim 2 wherein said alkane or cycloalkane is compound of formula R$^3$—H; said N-iodoamide is 1-iodo-3,5,5-trimethylhydantoin (1-ITMH) or 3-iodo-4,4-dimethyl-2-oxazolidinone (IDMO), wherein R$^3$ is linear or branched, substituted or unsubstituted alkyl or cycloalkyl; and wherein said organic iodide is R$^3$—I;
   wherein said reaction of step (b) is a radical iodination of alkane or cycloalkane represented by scheme (6):

   R$^3$—H+N-iodoamide→R$^3$—I+amide    (6)

wherein said reaction is provided under visual light irradiation of the reaction mixture.

9. The process of claim 2, wherein said alkene is compound of formula RCH=CHR$^1$, wherein said N-iodoamide is 1-iodo-3,5,5-trimethylhydantoin (1-ITMH), 3-iodo-4,4-dimethyl-2-oxazolidinone (IDMO), or N-iodosaccharin (NISac); wherein R is saturated, linear or branched, substituted or unsubstituted alkyl; substituted or unsubstituted Ph(CH$_2$)$_p$— wherein said p is an integer between 1 and 6; substituted or unsubstituted aryl; saturated or unsaturated, substituted or unsubstituted cycloalkyl or heterocycloalkyl; R$^1$ is hydrogen, saturated, linear or branched, substituted or unsubstituted alkyl; substituted or unsubstituted aryl; substituted or unsubstituted Ph(CH$_2$)$_t$— wherein t is an integer between 1 and 6; saturated or unsaturated, substituted or unsubstituted cycloalkyl or heterocycloalkyl; and R and R$^1$ optionally form a ring;
   wherein said reaction of step (b) is electrophilic iodination of alkene represented by scheme (7):

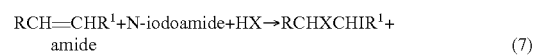
   RCH=CHR$^1$+N-iodoamide+HX→RCHXCHIR$^1$+amide    (7)

wherein said reaction is provided under heterolytic reaction conditions;
wherein X is OH, halogen, alkoxy or acyloxy group; and
wherein said organic iodide is RCHXCHIR¹.

10. The process of claim 2, wherein said alkyne is a compound of formula RC≡CR¹, said N-iodoamide is 1-iodo-3,5,5-trimethylhydantoin (1-ITMH), 3-iodo-4,4-dimethyl-2-oxazolidinone (IDMO), or N-iodosaccharin (NISac); wherein R is saturated, linear or branched, substituted or unsubstituted alkyl; substituted or unsubstituted Ph(CH₂)$_p$— wherein said p is an integer between 1 to and 6; substituted or unsubstituted aryl; saturated or unsaturated, substituted or unsubstituted cycloalkyl or heterocycloalkyl; R¹ is hydrogen, saturated, linear or branched, substituted or unsubstituted alkyl; substituted or unsubstituted aryl; substituted or unsubstituted Ph(CH₂)$_t$— wherein said t is an integer between 1 and 6; saturated or unsaturated, substituted or unsubstituted cycloalkyl or heterocycloalkyl;
wherein said reaction of step (b) is electrophilic iodination of alkyne represented by scheme (8):

RC≡CR¹+N-iodoamide+HX→RCX=CIR¹+amide    (8)

wherein said reaction is provided under heterolytic reaction conditions;
wherein X is OH, halogen, alkoxy, or acyloxy group; and wherein said organic iodide is RCX=CIR¹ or its tautomer, if X is OH.

11. The process of claim 2, wherein said ketone is a compound of formula RCOCH₂R¹, said N-iodoamide is 1-iodo-3,5,5-trimethylhydantoin (1-ITMH), 3-iodo-4,4-dimethyl-2-oxazolidinone (IDMO), or N-iodosaccharin (NISac); wherein R is saturated, linear or branched, substituted or unsubstituted alkyl; substituted or unsubstituted Ph(CH₂)$_o$— wherein said o is an integer between 1 and 6; substituted or unsubstituted aryl; saturated or unsaturated, substituted or unsubstituted cycloalkyl or heterocycloalkyl; R¹ is hydrogen, saturated, linear or branched, substituted or unsubstituted alkyl; substituted or unsubstituted aryl; substituted or unsubstituted Ph(CH₂)$_t$— wherein t is an integer between 1 and 6; saturated or unsaturated, substituted or unsubstituted cycloalkyl or heterocycloalkyl; and wherein said organic iodide is RCOCHIR¹;
wherein said reaction of step (b) is electrophilic iodination of ketone represented by scheme (9):

RCOCH₂R¹+N-iodoamide→RCOCHIR¹+amide    (9)

wherein said reaction is provided under heterolytic reaction conditions.

12. The process of claim 1, wherein said recovered amide of step (c) is further used for the preparation of N-iodoamide in step (a).

13. A process for the preparation of N-iodoamide comprising reacting a primary or a secondary amide with iodine and [bis(acyloxy)iodo]arene in an aprotic solvent to yield desired N-iodoamide and iodoarene as co-product, wherein said N-iodoamide is represented by formula (1B):

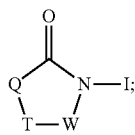

(1B)

wherein W is C=O, SO₂, or C(CH₃)₂; T is CH₂, C=O, C(CH₃)₂;

Q is O, NCH₃, CH₂; or T and Q are carbons and are fused together with a substituted or unsubstituted benzene; wherein said substituents are NO₂, CN, CF₃, halogen, or combination thereof.

14. The process of claim 13 wherein said N-iodoamide is 3-iodo-4,4-dimethyloxazolidin-2-one (IDMO), 1-iodo-3,5,5-trimethylhydantoin (1-ITMH), 3-iodo-1,5,5-trimethylhydantoin (3-ITMH), N-iodosaccharin (NISac), N-iodosuccinimide (NIS), N-iodophthalimide (IPT), or N-iodo-4-nitrophthalimide (INPT).

15. The process of claim 1, wherein said iodoarene co-product is further isolated from the reaction mixture and optionally oxidized to yield [bis(acyloxy)iodo]arene.

16. The process of claim 1, wherein said arene of said [bis(acyloxy)iodo]arene is substituted or unsubstituted benzene, or said acyl group of said [bis(acyloxy)iodo]arene is substituted or unsubstituted acetyl or benzoyl group.

17. The process of claim 1, wherein said aprotic solvent is aromatic or aliphatic hydrocarbon, a halogenated aromatic or a halogenated aliphatic hydrocarbon, nitrile, nitro compounds, ester, ether, substituted amide, or mixture thereof.

18. A crystalline form of 3-iodo-4,4-dimethyloxazolidin-2-one (IDMO) represented by the following structure:

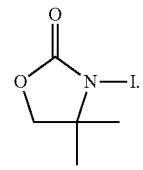

IDMO

19. The crystalline form of claim 18 characterized by molecular packing arrangement defined by space group P 21/n and unit cell dimensions a=5.7963(3) Å, b=10.9989(5) Å, c=11.9849(6) Å, α=γ=90°, β=98.580(2°) at 200(1) K.

20. A compound, wherein said compound is 1-iodo-3,5,5-trimethylhydantoin (1-ITMH) represented by the following structure:

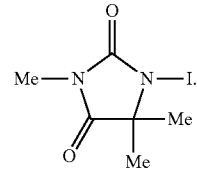

1-ITMH

21. A crystalline form of 1-iodo-3,5,5-trimethylhydantoin.

22. The crystalline form of claim 21, characterized by an x-ray powder diffraction pattern having characteristic peaks, expressed in degrees 2θ at about 13.0±0.2, 17.0±0.2, 22.6±0.2, 22.9±0.2, 25.2±0.2, 26.4±0.2, 28.3±0.2, 29.5±0.2, and 34.7±0.2 at 293(2) K.

23. The process of claim 13, wherein said iodoarene co-product is further isolated from the reaction mixture and optionally oxidized to yield [bis(acyloxy)iodo]arene.

24. The process of claim 13, wherein said arene of said [bis(acyloxy)iodo]arene is substituted or unsubstituted benzene or said acyl group of said [bis(acyloxy)iodo]arene is substituted or unsubstituted acetyl or benzoyl group.

* * * * *